(12) United States Patent
Wixey

(10) Patent No.: US 12,359,696 B2
(45) Date of Patent: Jul. 15, 2025

(54) STAPLER WITH COMPOSITE CARDAN AND SCREW DRIVE

(71) Applicant: Intuitive Surgical Operations, Inc., Sunnyvale, CA (US)

(72) Inventor: Matthew A. Wixey, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 769 days.

(21) Appl. No.: 17/176,986

(22) Filed: Feb. 16, 2021

(65) Prior Publication Data

US 2021/0161529 A1    Jun. 3, 2021

Related U.S. Application Data

(62) Division of application No. 15/772,527, filed as application No. PCT/US2016/059527 on Oct. 28, 2016, now Pat. No. 10,973,517.

(60) Provisional application No. 62/255,123, filed on Nov. 13, 2015.

(51) Int. Cl.
　　*F16D 3/32*　　　(2006.01)
　　*A61B 17/00*　　　(2006.01)
　　*A61B 17/072*　　　(2006.01)

(52) U.S. Cl.
　　CPC ........ *F16D 3/32* (2013.01); *A61B 2017/0069* (2013.01)

(58) Field of Classification Search
　　CPC ..... A61B 2017/0069; F16D 3/32; F16D 3/33; F16D 3/34; F16D 3/40; F16D 3/41; F16D 3/44

USPC .......................................... 464/109, 117, 159
See application file for complete search history.

(56) References Cited

U.S. PATENT DOCUMENTS

| | | | |
|---|---|---|---|
| 75,364 A * | 3/1868 | Case | F16D 3/34 464/109 |
| 3,792,597 A * | 2/1974 | Orain | F16D 3/33 464/118 |
| 4,305,539 A | 12/1981 | Korolkov et al. | |
| 4,319,576 A | 3/1982 | Rothfuss | |

(Continued)

FOREIGN PATENT DOCUMENTS

| CN | 103889344 A | 6/2014 |
|---|---|---|
| CN | 104042275 A | 9/2014 |

(Continued)

OTHER PUBLICATIONS

International Search Report and Written Opinion for Application No. PCT/US2016/059527, mailed on Feb. 16, 2017, 13 pages.

(Continued)

*Primary Examiner* — Josh Skroupa
(74) *Attorney, Agent, or Firm* — Farber LLC

(57) ABSTRACT

A universal double joint is provided comprising: a drive rotatable bearing having a first spherical surface formed of a plastic material; a proximal metal cross pin configured to receive an imparted drive force and to impart the imparted drive force to the first rotatable bearing; a driven rotatable bearing having a second spherical surface formed of a plastic material; and a distal metal cross pin configured to receive the imparted drive force and to impart the imparted drive force to the second rotatable bearing.

18 Claims, 32 Drawing Sheets

(56) References Cited

U.S. PATENT DOCUMENTS

| | | | |
|---|---|---|---|
| 4,352,276 A * | 10/1982 | Smith | F16D 3/32 464/109 |
| 4,403,892 A | 9/1983 | Kane | |
| 4,407,286 A | 10/1983 | Noiles et al. | |
| 4,429,695 A | 2/1984 | Green | |
| 4,509,518 A | 4/1985 | McGarry et al. | |
| 4,509,932 A | 4/1985 | Weible | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,633,874 A | 1/1987 | Chow et al. | |
| 4,767,044 A | 8/1988 | Green | |
| 4,809,695 A | 3/1989 | Gwathmey et al. | |
| 4,848,637 A | 7/1989 | Pruitt | |
| 4,892,244 A | 1/1990 | Fox et al. | |
| 4,930,503 A | 6/1990 | Pruitt | |
| 4,978,049 A | 12/1990 | Green | |
| 5,007,300 A | 4/1991 | Siva | |
| 5,027,834 A | 7/1991 | Pruitt | |
| 5,040,715 A | 8/1991 | Green et al. | |
| 5,133,735 A | 7/1992 | Slater et al. | |
| 5,133,736 A | 7/1992 | Bales, Jr. et al. | |
| 5,142,931 A | 9/1992 | Menahem | |
| 5,147,357 A | 9/1992 | Rose et al. | |
| 5,180,092 A | 1/1993 | Crainich | |
| 5,275,323 A | 1/1994 | Schulze et al. | |
| 5,307,976 A | 5/1994 | Olson et al. | |
| 5,312,023 A | 5/1994 | Green et al. | |
| 5,316,435 A | 5/1994 | Mozingo | |
| 5,334,183 A | 8/1994 | Wuchinich | |
| 5,342,395 A | 8/1994 | Jarrett et al. | |
| 5,342,396 A | 8/1994 | Cook | |
| 5,366,133 A | 11/1994 | Geiste | |
| 5,452,836 A | 9/1995 | Huitema et al. | |
| 5,452,837 A | 9/1995 | Williamson, IV et al. | |
| 5,465,895 A | 11/1995 | Knodel et al. | |
| 5,480,089 A | 1/1996 | Blewett | |
| 5,484,095 A | 1/1996 | Green et al. | |
| 5,484,451 A | 1/1996 | Akopov et al. | |
| 5,487,500 A | 1/1996 | Knodel et al. | |
| 5,497,931 A | 3/1996 | Nakamura | |
| 5,533,521 A | 7/1996 | Granger | |
| 5,540,375 A | 7/1996 | Bolanos et al. | |
| 5,554,164 A | 9/1996 | Wilson et al. | |
| 5,560,530 A | 10/1996 | Bolanos et al. | |
| 5,562,239 A | 10/1996 | Boiarski et al. | |
| 5,564,615 A | 10/1996 | Bishop et al. | |
| 5,571,116 A | 11/1996 | Bolanos et al. | |
| 5,571,285 A | 11/1996 | Chow et al. | |
| 5,573,534 A | 11/1996 | Stone | |
| 5,607,449 A | 3/1997 | Tontarra | |
| 5,615,820 A | 4/1997 | Viola | |
| 5,624,452 A | 4/1997 | Yates | |
| 5,628,446 A | 5/1997 | Geiste et al. | |
| 5,632,432 A | 5/1997 | Schulze et al. | |
| 5,651,491 A | 7/1997 | Heaton et al. | |
| 5,652,849 A | 7/1997 | Conway et al. | |
| 5,667,626 A | 9/1997 | Cayford et al. | |
| 5,673,840 A | 10/1997 | Schulze et al. | |
| 5,673,842 A | 10/1997 | Bittner et al. | |
| 5,676,674 A | 10/1997 | Bolanos et al. | |
| 5,688,269 A | 11/1997 | Newton et al. | |
| 5,690,269 A | 11/1997 | Bolanos et al. | |
| 5,693,042 A | 12/1997 | Boiarski et al. | |
| 5,697,542 A | 12/1997 | Knodel et al. | |
| 5,700,270 A | 12/1997 | Peyser et al. | |
| 5,700,276 A | 12/1997 | Benecke | |
| 5,704,534 A | 1/1998 | Huitema et al. | |
| 5,709,680 A | 1/1998 | Yates et al. | |
| 5,738,474 A | 4/1998 | Blewett | |
| 5,752,644 A | 5/1998 | Bolanos et al. | |
| 5,752,973 A | 5/1998 | Kieturakis et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,782,396 A | 7/1998 | Mastri et al. | |
| 5,792,135 A | 8/1998 | Madhani et al. | |
| 5,820,009 A | 10/1998 | Melling et al. | |
| 5,826,776 A | 10/1998 | Schulze et al. | |
| 5,833,695 A | 11/1998 | Yoon | |
| 5,865,361 A | 2/1999 | Milliman et al. | |
| 5,871,135 A | 2/1999 | Williamson, IV et al. | |
| 5,911,353 A | 6/1999 | Bolanos et al. | |
| 5,915,616 A | 6/1999 | Viola et al. | |
| 5,919,198 A | 7/1999 | Graves, Jr. et al. | |
| 5,941,442 A | 8/1999 | Geiste et al. | |
| 5,954,259 A | 9/1999 | Viola et al. | |
| 5,959,892 A | 9/1999 | Lin et al. | |
| 6,032,849 A | 3/2000 | Mastri et al. | |
| 6,050,996 A | 4/2000 | Schmaltz et al. | |
| 6,079,606 A | 6/2000 | Milliman et al. | |
| 6,113,598 A | 9/2000 | Baker | |
| 6,126,666 A | 10/2000 | Trapp et al. | |
| 6,174,309 B1 | 1/2001 | Wrublewski et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,312,426 B1 | 11/2001 | Goldberg et al. | |
| 6,330,956 B1 | 12/2001 | Willinger | |
| 6,330,965 B1 | 12/2001 | Milliman et al. | |
| 6,488,196 B1 | 12/2002 | Fenton, Jr. | |
| 6,503,259 B2 | 1/2003 | Huxel et al. | |
| 6,582,451 B1 | 6/2003 | Marucci et al. | |
| 6,585,735 B1 | 7/2003 | Frazier et al. | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,692,363 B1 * | 2/2004 | Heutschi | F16D 3/32 464/118 |
| 6,770,072 B1 | 8/2004 | Truckai et al. | |
| 6,786,382 B1 | 9/2004 | Hoffman | |
| 6,817,974 B2 | 11/2004 | Cooper et al. | |
| 6,840,938 B1 | 1/2005 | Morley et al. | |
| 6,877,647 B2 | 4/2005 | Green et al. | |
| 6,905,057 B2 | 6/2005 | Swayze et al. | |
| 6,953,139 B2 | 10/2005 | Milliman et al. | |
| 6,955,608 B1 * | 10/2005 | Lutz | F16D 3/33 464/118 |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,985,133 B1 | 1/2006 | Rodomista et al. | |
| 6,986,451 B1 | 1/2006 | Mastri et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,044,353 B2 | 5/2006 | Mastri et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,114,642 B2 | 10/2006 | Whitman | |
| 7,128,253 B2 | 10/2006 | Mastri et al. | |
| 7,140,527 B2 | 11/2006 | Ehrenfels et al. | |
| 7,140,528 B2 | 11/2006 | Shelton, IV et al. | |
| 7,258,262 B2 | 8/2007 | Mastri et al. | |
| 7,296,722 B2 | 11/2007 | Ivanko | |
| 7,308,998 B2 | 12/2007 | Mastri et al. | |
| 7,328,828 B2 | 2/2008 | Ortiz et al. | |
| 7,380,695 B2 | 6/2008 | Doll et al. | |
| 7,380,696 B2 | 6/2008 | Shelton, IV et al. | |
| 7,398,908 B2 | 7/2008 | Holsten et al. | |
| 7,401,721 B2 | 7/2008 | Holsten et al. | |
| 7,407,075 B2 | 8/2008 | Holsten et al. | |
| 7,455,676 B2 | 11/2008 | Holsten et al. | |
| 7,472,814 B2 | 1/2009 | Mastri et al. | |
| 7,481,349 B2 | 1/2009 | Holsten et al. | |
| 7,491,202 B2 | 2/2009 | Odom et al. | |
| 7,494,039 B2 | 2/2009 | Racenet et al. | |
| 7,561,141 B2 | 7/2009 | Shahoian et al. | |
| 7,565,993 B2 | 7/2009 | Milliman et al. | |
| 7,588,174 B2 | 9/2009 | Holsten et al. | |
| 7,654,431 B2 | 2/2010 | Hueil et al. | |

(56) References Cited

U.S. PATENT DOCUMENTS

| | | |
|---|---|---|
| 7,658,312 B2 | 2/2010 | Vidal et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,780,577 B2 | 8/2010 | Arnold |
| 7,794,475 B2 | 9/2010 | Hess et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,439,246 B1 | 5/2013 | Knodel |
| 8,490,851 B2 | 7/2013 | Blier et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,206 B2 | 3/2014 | Aranyi et al. |
| 8,672,939 B2 | 3/2014 | Garrison |
| 8,701,960 B1 | 4/2014 | Manoux et al. |
| 8,783,541 B2 | 7/2014 | Shelton, IV et al. |
| 8,800,841 B2 | 8/2014 | Ellerhorst et al. |
| 8,834,518 B2 | 9/2014 | Faller et al. |
| 8,851,355 B2 | 10/2014 | Aranyi et al. |
| 8,852,174 B2 | 10/2014 | Burbank |
| 8,858,547 B2 | 10/2014 | Brogna |
| 8,864,010 B2 | 10/2014 | Williams |
| 8,876,857 B2 | 11/2014 | Burbank |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,016,545 B2 | 4/2015 | Aranyi et al. |
| 9,055,961 B2 | 6/2015 | Manzo et al. |
| 9,161,807 B2 | 10/2015 | Garrison |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,307,986 B2 | 4/2016 | Hall et al. |
| 9,316,267 B2 * | 4/2016 | Lenz ................ F16D 3/32 |
| 9,345,479 B2 | 5/2016 | Racenet et al. |
| 9,498,215 B2 | 11/2016 | Duque et al. |
| 9,717,497 B2 | 8/2017 | Zerkle et al. |
| 9,717,498 B2 | 8/2017 | Aranyi et al. |
| 9,777,459 B2 | 10/2017 | Zuritis |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,231,733 B2 | 3/2019 | Ehrenfels et al. |
| 10,285,693 B2 | 5/2019 | Kimsey et al. |
| 10,335,147 B2 | 7/2019 | Rector et al. |
| 10,363,037 B2 | 7/2019 | Aronhalt et al. |
| 10,646,219 B2 | 5/2020 | Racenet et al. |
| 10,722,233 B2 | 7/2020 | Wellman |
| 10,828,027 B2 | 11/2020 | Racenet et al. |
| 10,863,988 B2 | 12/2020 | Patel et al. |
| 10,912,556 B2 | 2/2021 | Burbank |
| 10,973,517 B2 | 4/2021 | Wixey |
| 11,020,138 B2 | 6/2021 | Ragosta |
| 11,166,773 B2 | 11/2021 | Ragosta et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,607,219 B2 | 3/2023 | Shelton, IV et al. |
| 11,642,129 B2 | 5/2023 | Burbank |
| 11,696,758 B2 | 7/2023 | Murphy et al. |
| 11,723,661 B2 | 8/2023 | Wixey et al. |
| 11,759,202 B2 | 9/2023 | Morgan et al. |
| 11,786,325 B2 | 10/2023 | Mustufa et al. |
| 11,806,015 B2 | 11/2023 | Wixey et al. |
| 11,857,188 B2 | 1/2024 | Hites |
| 11,864,762 B2 | 1/2024 | Wixey |
| 11,896,224 B2 | 2/2024 | Wellman |
| 11,903,583 B2 | 2/2024 | Burbank et al. |
| 11,944,301 B2 | 4/2024 | Wixey et al. |
| 11,944,302 B2 | 4/2024 | Wixey et al. |
| 11,986,184 B2 | 5/2024 | Patel et al. |
| 12,000,280 B2 | 6/2024 | King |
| 12,011,168 B2 | 6/2024 | Wixey |
| 12,029,426 B2 | 7/2024 | Millman et al. |
| 12,029,473 B2 | 7/2024 | Whitlock et al. |
| 12,089,844 B2 | 9/2024 | Patel et al. |
| 12,137,903 B2 | 11/2024 | Patel et al. |
| 12,156,654 B2 | 12/2024 | Wellman |
| 2002/0165562 A1 | 11/2002 | Grant et al. |
| 2002/0177843 A1 | 11/2002 | Anderson et al. |
| 2002/0188293 A1 | 12/2002 | Manzo |
| 2002/0188294 A1 | 12/2002 | Couture et al. |
| 2003/0036748 A1 | 2/2003 | Cooper et al. |
| 2003/0078577 A1 | 4/2003 | Truckai et al. |
| 2003/0135204 A1 | 7/2003 | Lee et al. |
| 2003/0144652 A1 | 7/2003 | Baker et al. |
| 2003/0171747 A1 | 9/2003 | Kanehira et al. |
| 2003/0181910 A1 | 9/2003 | Dycus et al. |
| 2004/0006340 A1 | 1/2004 | Latterell et al. |
| 2004/0049185 A1 | 3/2004 | Latterell et al. |
| 2004/0143263 A1 | 7/2004 | Schechter et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0021027 A1 | 1/2005 | Shields et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0171533 A1 | 8/2005 | Latterell et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0020287 A1 | 1/2006 | Lee et al. |
| 2006/0022014 A1 | 2/2006 | Shelton, IV et al. |
| 2006/0022015 A1 | 2/2006 | Shelton et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0124689 A1 | 6/2006 | Arad et al. |
| 2006/0161190 A1 | 7/2006 | Gadberry et al. |
| 2006/0190031 A1 | 8/2006 | Wales et al. |
| 2006/0199999 A1 | 9/2006 | Ikeda et al. |
| 2006/0217706 A1 | 9/2006 | Lau et al. |
| 2006/0217709 A1 | 9/2006 | Couture et al. |
| 2006/0271042 A1 | 11/2006 | Latterell et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0029577 A1 | 2/2008 | Shelton et al. |
| 2008/0064572 A1 | 3/2008 | Nardone |

(56) References Cited

U.S. PATENT DOCUMENTS

| | | |
|---|---|---|
| 2008/0065100 A1 | 3/2008 | Larkin |
| 2008/0078804 A1 | 4/2008 | Shelton et al. |
| 2008/0086114 A1 | 4/2008 | Schmitz et al. |
| 2008/0093517 A1 | 4/2008 | Chen |
| 2008/0108446 A1* | 5/2008 | Faude .................. F16D 3/40 464/136 |
| 2008/0161174 A1 | 7/2008 | Lo |
| 2008/0196533 A1 | 8/2008 | Bergamasco et al. |
| 2008/0210738 A1 | 9/2008 | Shelton et al. |
| 2008/0280736 A1 | 11/2008 | D'Eredita |
| 2008/0305934 A1 | 12/2008 | Medina |
| 2008/0308607 A1 | 12/2008 | Timm et al. |
| 2009/0181832 A1 | 7/2009 | Bell |
| 2009/0277947 A1 | 11/2009 | Viola |
| 2010/0006620 A1 | 1/2010 | Sorrentino et al. |
| 2010/0009818 A1 | 1/2010 | Simonson et al. |
| 2010/0057081 A1 | 3/2010 | Hanna |
| 2010/0057085 A1 | 3/2010 | Holcomb et al. |
| 2010/0076461 A1 | 3/2010 | Viola et al. |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0213240 A1 | 8/2010 | Kostrzewski |
| 2010/0331857 A1 | 12/2010 | Doyle et al. |
| 2011/0022078 A1 | 1/2011 | Hinman |
| 2011/0036891 A1 | 2/2011 | Zemlok et al. |
| 2011/0087238 A1 | 4/2011 | Wang et al. |
| 2011/0118707 A1 | 5/2011 | Burbank |
| 2011/0118778 A1 | 5/2011 | Burbank |
| 2011/0121050 A1 | 5/2011 | Nicholas et al. |
| 2011/0152879 A1 | 6/2011 | Williams |
| 2011/0174863 A1 | 7/2011 | Shelton, IV et al. |
| 2011/0186614 A1 | 8/2011 | Kasvikis |
| 2011/0251613 A1 | 10/2011 | Guerra et al. |
| 2011/0282339 A1 | 11/2011 | Weizman et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2011/0319886 A1 | 12/2011 | Chojin et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0205419 A1 | 8/2012 | Weir et al. |
| 2012/0209253 A1 | 8/2012 | Donhowe |
| 2012/0215220 A1 | 8/2012 | Manzo et al. |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2012/0289999 A1 | 11/2012 | Frank |
| 2012/0298719 A1 | 11/2012 | Shelton, IV et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0075448 A1 | 3/2013 | Schmid et al. |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0240604 A1 | 9/2013 | Knodel |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005662 A1 | 1/2014 | Shelton, IV |
| 2014/0021239 A1 | 1/2014 | Kostrzewski |
| 2014/0025071 A1 | 1/2014 | Sims et al. |
| 2014/0027492 A1 | 1/2014 | Williams |
| 2014/0100569 A1 | 4/2014 | Lawes et al. |
| 2014/0100600 A1 | 4/2014 | Kendrick |
| 2014/0103093 A1 | 4/2014 | Koch, Jr. et al. |
| 2014/0110455 A1 | 4/2014 | Ingmanson et al. |
| 2014/0175152 A1 | 6/2014 | Hess et al. |
| 2014/0180286 A1 | 6/2014 | Marczyk et al. |
| 2014/0183244 A1 | 7/2014 | Duque et al. |
| 2014/0200596 A1 | 7/2014 | Weir et al. |
| 2014/0200612 A1 | 7/2014 | Weir et al. |
| 2014/0200851 A1 | 7/2014 | Weir et al. |
| 2014/0214049 A1 | 7/2014 | Jeong et al. |
| 2014/0239036 A1 | 8/2014 | Zerkle et al. |
| 2014/0239044 A1 | 8/2014 | Hoffman |
| 2014/0239046 A1 | 8/2014 | Milliman et al. |
| 2014/0246477 A1 | 9/2014 | Koch, Jr. et al. |
| 2014/0249557 A1 | 9/2014 | Koch, Jr. et al. |
| 2014/0257331 A1 | 9/2014 | Kim et al. |
| 2014/0263546 A1 | 9/2014 | Aranyi |
| 2014/0263552 A1 | 9/2014 | Hall et al. |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0276731 A1 | 9/2014 | Voegele et al. |
| 2014/0276776 A1 | 9/2014 | Parihar et al. |
| 2014/0284372 A1 | 9/2014 | Kostrzewski |
| 2014/0305989 A1 | 10/2014 | Parihar et al. |
| 2014/0309666 A1 | 10/2014 | Shelton, IV et al. |
| 2014/0343550 A1 | 11/2014 | Faller et al. |
| 2014/0343569 A1 | 11/2014 | Turner |
| 2014/0364851 A1 | 12/2014 | Batross et al. |
| 2015/0018856 A1 | 1/2015 | Poo et al. |
| 2015/0073746 A1 | 3/2015 | Gris et al. |
| 2015/0088131 A1 | 3/2015 | Weisshaupt et al. |
| 2015/0141981 A1 | 5/2015 | Price et al. |
| 2015/0141993 A1 | 5/2015 | Schechter et al. |
| 2015/0173756 A1 | 6/2015 | Baxter, III et al. |
| 2015/0173789 A1 | 6/2015 | Baxter, III et al. |
| 2015/0209030 A1 | 7/2015 | Kostrzewski et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0272583 A1 | 10/2015 | Leimbach et al. |
| 2015/0272606 A1 | 10/2015 | Nobis |
| 2015/0297227 A1 | 10/2015 | Huitema et al. |
| 2015/0297230 A1 | 10/2015 | Schellin et al. |
| 2015/0297235 A1 | 10/2015 | Harris et al. |
| 2015/0316431 A1 | 11/2015 | Collins et al. |
| 2015/0369277 A1* | 12/2015 | Fevre .................. F16D 3/32 403/57 |
| 2015/0374396 A1 | 12/2015 | Strobl et al. |
| 2016/0038227 A1 | 2/2016 | Garrison |
| 2016/0058441 A1 | 3/2016 | Morgan et al. |
| 2016/0058450 A1 | 3/2016 | Shelton, IV et al. |
| 2016/0066916 A1 | 3/2016 | Overmyer et al. |
| 2016/0089148 A1 | 3/2016 | Harris et al. |
| 2016/0120544 A1 | 5/2016 | Shelton, IV et al. |
| 2016/0157863 A1 | 6/2016 | Williams et al. |
| 2016/0174973 A1 | 6/2016 | Shelton, IV et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0199124 A1 | 7/2016 | Thomas et al. |
| 2016/0235473 A1 | 8/2016 | Hagland |
| 2016/0235489 A1 | 8/2016 | Gombert et al. |
| 2016/0242782 A1 | 8/2016 | Shelton, IV et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0287316 A1 | 10/2016 | Worrell et al. |
| 2016/0296226 A1 | 10/2016 | Kostrzewski |
| 2016/0317216 A1 | 11/2016 | Hermes et al. |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0056098 A1 | 3/2017 | Crews et al. |

(56) References Cited

U.S. PATENT DOCUMENTS

| | | |
|---|---|---|
| 2017/0065331 A1 | 3/2017 | Mayer et al. |
| 2017/0079710 A1 | 3/2017 | Deville et al. |
| 2017/0097035 A1 | 4/2017 | Zimmerman et al. |
| 2017/0105754 A1 | 4/2017 | Boudreaux et al. |
| 2017/0135746 A1 | 5/2017 | Tetzlaff et al. |
| 2017/0143335 A1 | 5/2017 | Gupta et al. |
| 2017/0156788 A1 | 6/2017 | Johnson et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0078268 A1 | 3/2018 | Messerly et al. |
| 2018/0125570 A1 | 5/2018 | Rioux |
| 2018/0161052 A1 | 6/2018 | Weir et al. |
| 2018/0168581 A1 | 6/2018 | Hunter et al. |
| 2018/0168585 A1 | 6/2018 | Shelton, IV et al. |
| 2018/0168620 A1 | 6/2018 | Huang et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0250085 A1 | 9/2018 | Simi et al. |
| 2018/0296213 A1 | 10/2018 | Strobl |
| 2018/0310935 A1 | 11/2018 | Wixey |
| 2018/0310948 A1 | 11/2018 | Stamm et al. |
| 2018/0317915 A1 | 11/2018 | Mcdonald, II |
| 2019/0000454 A1 | 1/2019 | Swayze et al. |
| 2019/0000525 A1 | 1/2019 | Messerly et al. |
| 2019/0015124 A1 | 1/2019 | Williams et al. |
| 2019/0029746 A1 | 1/2019 | Dudhedia et al. |
| 2019/0059894 A1 | 2/2019 | Kumada et al. |
| 2019/0076143 A1 | 3/2019 | Smith |
| 2019/0083086 A1 | 3/2019 | Klaffenböck et al. |
| 2019/0083819 A1 | 3/2019 | Mitchell et al. |
| 2019/0099181 A1 | 4/2019 | Shelton, IV et al. |
| 2019/0125347 A1 | 5/2019 | Stokes et al. |
| 2019/0133571 A1 | 5/2019 | Racenet et al. |
| 2019/0142531 A1 | 5/2019 | Wentworth et al. |
| 2019/0192137 A1 | 6/2019 | Shelton, IV et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0282233 A1 | 9/2019 | Burbank et al. |
| 2019/0290374 A1 | 9/2019 | Ramadorai |
| 2019/0298346 A1 | 10/2019 | Shelton, IV et al. |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0205811 A1 | 7/2020 | Posey et al. |
| 2021/0153927 A1 | 5/2021 | Ross et al. |
| 2021/0177412 A1 | 6/2021 | Wilson et al. |
| 2021/0177495 A1 | 6/2021 | Ross et al. |
| 2021/0177500 A1 | 6/2021 | Khalaji |
| 2021/0196350 A1 | 7/2021 | Fiebig et al. |
| 2021/0236119 A1 | 8/2021 | Chavan et al. |
| 2021/0267596 A1 | 9/2021 | Fanelli et al. |
| 2021/0386427 A1 | 12/2021 | Millman et al. |
| 2022/0015823 A1 | 1/2022 | Wilson et al. |
| 2022/0031346 A1 | 2/2022 | Parks |
| 2022/0054130 A1 | 2/2022 | Overmyer et al. |
| 2022/0061836 A1 | 3/2022 | Parihar et al. |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0167985 A1 | 6/2022 | George et al. |
| 2022/0183686 A1 | 6/2022 | Wixey et al. |
| 2022/0346790 A1 | 11/2022 | Wellman |
| 2022/0378537 A1 | 12/2022 | Hites et al. |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0101993 A1 | 3/2023 | Baril et al. |
| 2023/0120209 A1 | 4/2023 | Parks et al. |
| 2023/0210527 A1 | 7/2023 | Shelton, IV et al. |
| 2023/0225731 A1 | 7/2023 | Burbank |
| 2023/0329711 A1 | 10/2023 | Wixey et al. |
| 2024/0023961 A1 | 1/2024 | Wixey et al. |
| 2024/0065690 A1 | 2/2024 | Jasemian et al. |
| 2024/0081824 A1 | 3/2024 | Hites |
| 2024/0108343 A1 | 4/2024 | Wixey |
| 2024/0138834 A1 | 5/2024 | Wellman |
| 2024/0252171 A1 | 8/2024 | Wixey et al. |
| 2024/0260959 A1 | 8/2024 | Wixey et al. |
| 2024/0293122 A1 | 9/2024 | Wixey |
| 2024/0315761 A1 | 9/2024 | Whitlock et al. |
| 2024/0335194 A1 | 10/2024 | Patel et al. |
| 2024/0341766 A1 | 10/2024 | Millman et al. |
| 2024/0350143 A1 | 10/2024 | Yee et al. |
| 2024/0407782 A1 | 12/2024 | Patel et al. |

FOREIGN PATENT DOCUMENTS

| | | | |
|---|---|---|---|
| CN | 105007836 A | 10/2015 | |
| CN | 105769331 A | 7/2016 | |
| CN | 106232026 A | 12/2016 | |
| CN | 106491203 A | 3/2017 | |
| CN | 107920819 A | 4/2018 | |
| CN | 108024809 A | 5/2018 | |
| CN | 112165909 A | 1/2021 | |
| DE | 694747 C * | 8/1940 | ............... F16D 3/32 |
| DE | 3724525 C1 * | 5/1988 | ............... F16D 3/30 |
| DE | 102012103503 A1 | 10/2013 | |
| EP | 0277532 B1 | 8/1990 | |
| EP | 0469396 A1 * | 2/1992 | ............... F16D 3/32 |
| EP | 0277529 B1 | 4/1993 | |
| EP | 0641546 A1 | 3/1995 | |
| EP | 0986336 A1 | 3/2000 | |
| EP | 1090592 A1 | 4/2001 | |
| EP | 1479348 A1 | 11/2004 | |
| EP | 1728473 A1 | 12/2006 | |
| EP | 1479346 B1 | 1/2007 | |
| EP | 1621141 B1 | 7/2007 | |
| EP | 2374419 A2 | 10/2011 | |
| EP | 1316290 B1 | 2/2012 | |
| EP | 2517639 A1 | 10/2012 | |
| EP | 2540231 A2 | 1/2013 | |
| EP | 1754445 B1 | 10/2013 | |
| EP | 2777529 A1 | 9/2014 | |
| EP | 2777530 A1 | 9/2014 | |
| EP | 2777532 A2 | 9/2014 | |
| EP | 2779921 A2 | 9/2014 | |
| EP | 2944275 A2 | 11/2015 | |
| EP | 2992834 A1 | 3/2016 | |
| EP | 2992849 A1 | 3/2016 | |
| EP | 3000408 A2 | 3/2016 | |
| EP | 3120780 A2 | 1/2017 | |
| EP | 3135225 A2 | 3/2017 | |
| EP | 3158947 A1 | 4/2017 | |
| EP | 3173029 A1 | 5/2017 | |
| EP | 3205291 A1 | 8/2017 | |
| EP | 3338703 A1 | 6/2018 | |
| FR | 2828952 B1 | 12/2005 | |
| JP | 57094132 A * | 6/1982 | ............... F16D 3/18 |
| JP | 2001170069 A | 6/2001 | |
| JP | 5301166 B2 | 9/2013 | |
| JP | 2014530653 A | 11/2014 | |
| JP | 2016508792 A | 3/2016 | |
| JP | 2016513570 A | 5/2016 | |
| JP | 2017500146 A | 1/2017 | |
| JP | 2017513564 A | 6/2017 | |
| JP | 2017527396 A | 9/2017 | |

(56) References Cited

FOREIGN PATENT DOCUMENTS

| | | |
|---|---|---|
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2004020859 A1 * | 3/2004 ............... F16D 3/30 |
| WO | WO-2009112802 A1 | 9/2009 |
| WO | WO-2012142872 A1 | 10/2012 |
| WO | WO-2014106275 A1 | 7/2014 |
| WO | WO-2016073538 A1 | 5/2016 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |
| WO | WO-2019090047 A1 | 5/2019 |
| WO | WO-2020081960 A1 | 4/2020 |
| WO | WO-2020131685 A1 | 6/2020 |
| WO | WO-2020131692 A1 | 6/2020 |
| WO | WO-2022150215 A1 | 7/2022 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Anonymous: "Slip Joint Pliers—Wikipedia," Sep. 2017, 1 Pages. Retrieved from internet URL:https://en.wikipedia.org/w/index.php?tilte=split_joint_pliers&oldid=801407143.

Extended European Search Report for Application No. EP18823002.3 mailed on Mar. 5, 2021,11 pages.

Extended European Search Report for Application No. EP19757451.0, mailed on May 19, 2022, 16 pages.

Extended European Search Report for Application No. EP19898247.2, mailed on Jan. 10, 2023, 12 pages.

Extended European Search Report for Application No. EP19900059.7, mailed on Dec. 5, 2022, 10 pages.

Extended European Search Report for Application No. EP20790773.4, mailed on Nov. 29, 2022, 09 pages.

Extended European Search Report for Application No. EP20815112.6, mailed on Jan. 5, 2023, 11 pages.

Extended European Search Report for Application No. EP20875978.7, mailed on Jan. 31, 2024, 26 pages.

Extended European Search Report for Application No. EP24155564.8, mailed on Jul. 8, 2024, 12 pages.

International Search Report and Written Opinion for Application No. PCT/US2018/039912, mailed on Oct. 12, 2018, 15 pages.

European Search Report (Corrected version) for Application No. EP19750317.0, mailed on Mar. 28, 2022, 26 pages.

Field Application Note—Journal Bearings, Retrieved from Wayback Machine URL: https://web.archive.org/web/20100110095051/ http://www.reliabilitydirect.com/appnotes/jb.html, on Mar. 12, 2024, 04 pages.

International Search Report and Written Opinion for Application No. PCT/US2020/054568, mailed Jan. 29, 2021, 13 pages.

International Preliminary Report on Patentability for Application No. PCT/US2019/017646, mailed on Aug. 27, 2020, 10 pages.

International Preliminary Report on Patentability for Application No. PCT/US2019/019501, mailed Sep. 3, 2020, 7 pages.

International Search Report and Written Opinion for Application No. PCT/US2020/025655, mailed Jul. 22, 2020, 8 pages.

International Search Report and Written Opinion for Application No. PCT/US19/17646, mailed on Apr. 16, 2019, 11 pages.

International Search Report and Written Opinion for Application No. PCT/US2019/019501, mailed May 9, 2019, 8 pages.

International Search Report and Written Opinion for Application No. PCT/US2019/056979, mailed Dec. 18, 2019, 8 pages.

International Search Report and Written Opinion for Application No. PCT/US2019/062344, mailed Mar. 23, 2020, 17 pages.

International Search Report and Written Opinion for Application No. PCT/US2019/062768, mailed Mar. 9, 2020, 15 pages.

International Search Report and Written Opinion for Application No. PCT/US2019/064861, mailed Mar. 30, 2020, 18 pages.

International Search Report and Written Opinion for Application No. PCT/US2019/066513, mailed Apr. 21, 2020, 8 pages.

International Search Report and Written Opinion for Application No. PCT/US2019/066530, mailed Apr. 21, 2020, 8 pages.

International Search Report and Written Opinion for Application No. PCT/US2021/065544 mailed Jun. 2, 2022, 21 pages.

International Search Report and Written Opinion for Application No. PCT/US2020/020672, mailed Jun. 29, 2020, 10 pages.

International Search Report and Written Opinion for Application No. PCT/US2020/033481, mailed Sep. 3, 2020, 22 pages.

International Search Report and Written Opinion for Application No. PCT/US2021/012284 mailed May 6, 2021, 23 pages.

International Search Report and Written Opinion for Application No. PCT/US2021/065308, mailed Apr. 21, 2022. 13 pages.

Nicholson, C., et al., "Plane Bearings," ESC Report, BSA Educational Services Committee, Oct. 1994, vol. 5(1), 02 pages.

Partial European Search Report for Application No. EP19757451.0, mailed on Feb. 2, 2022, 12 pages.

Supplementary European Search Report for Application No. EP19873128.3, mailed on Jun. 22, 2022, 7 pages.

Burstein M.D., "8 MM Sureform 30 Staplers and Reloads," Sages, Jun. 2022, 1 Page. Retrieved from internet URL: https://www.accessdata.fda.gov/cdrh_docs/pdf21/K211997.pdf.

Jaggi A., "8 mm SureForm 30 Curved-Tip Stapler, 8 mm SureForm 30 Stapler, SureForm 30 Reloads," U.S Food & Drug Administration, Dec. 2021, 11 pages. Retrieved from the internet URL:https://www.sages.org/publications/tavac/8-mm-sureform-30-staplers-and-reloads/.

* cited by examiner

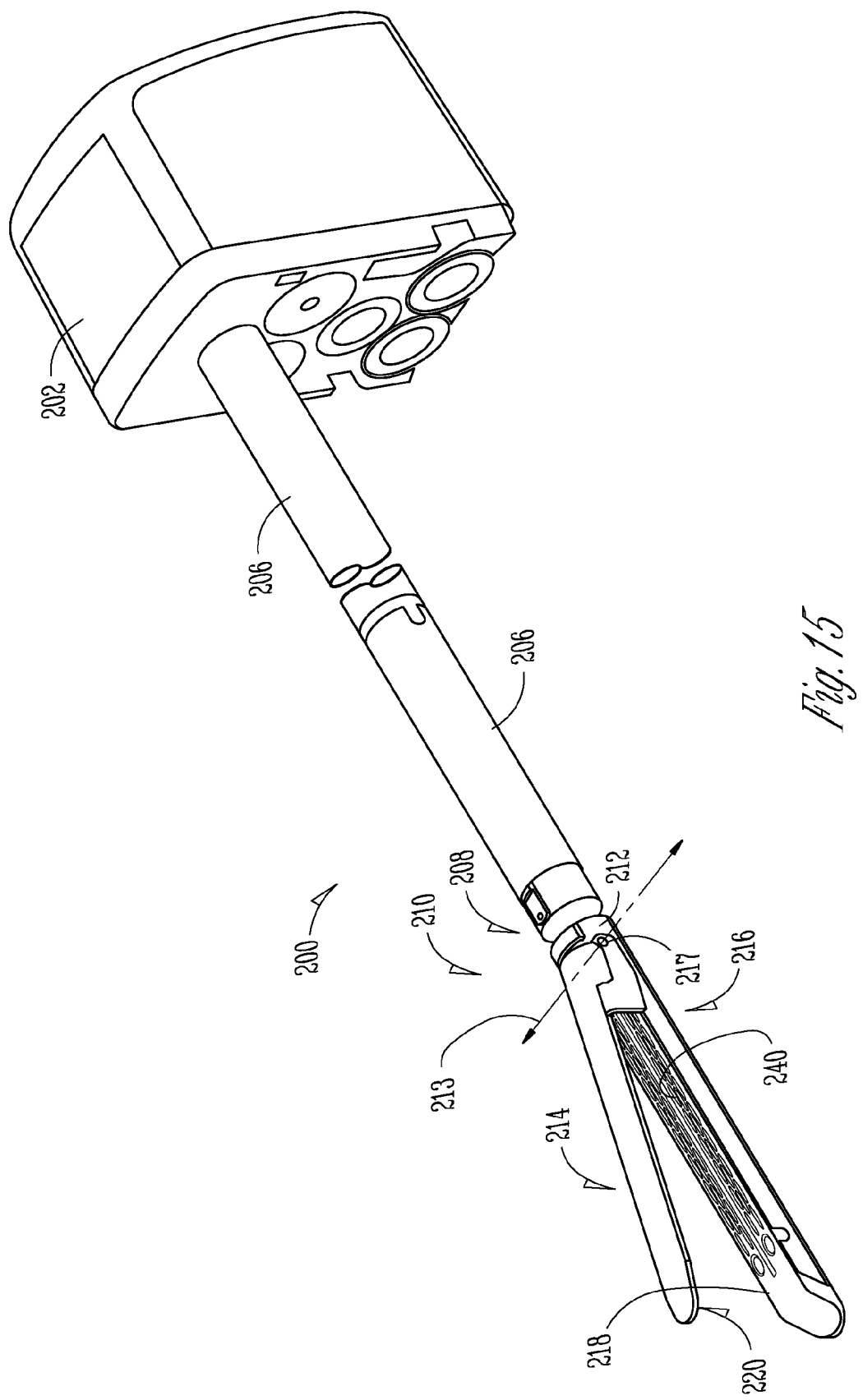

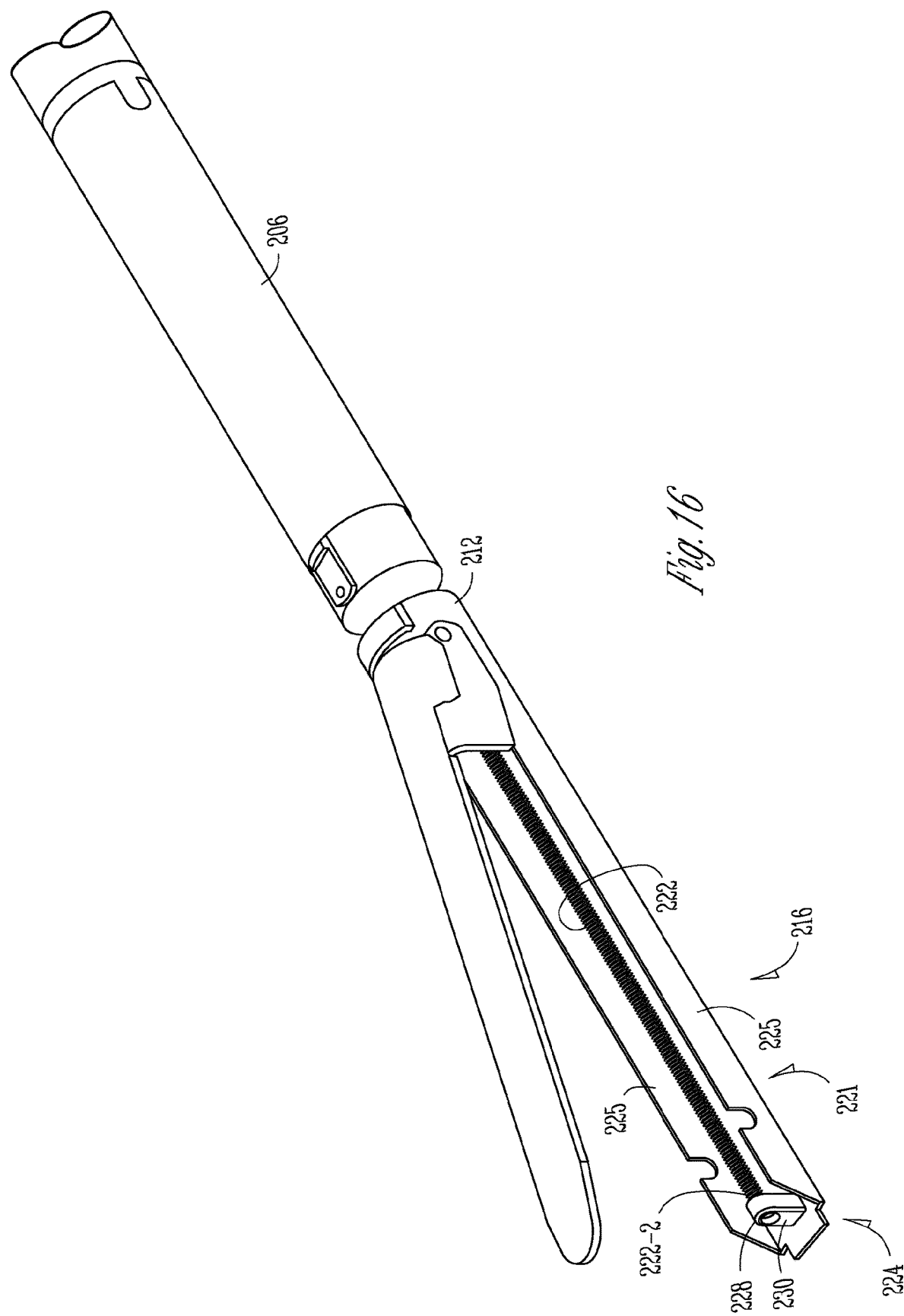

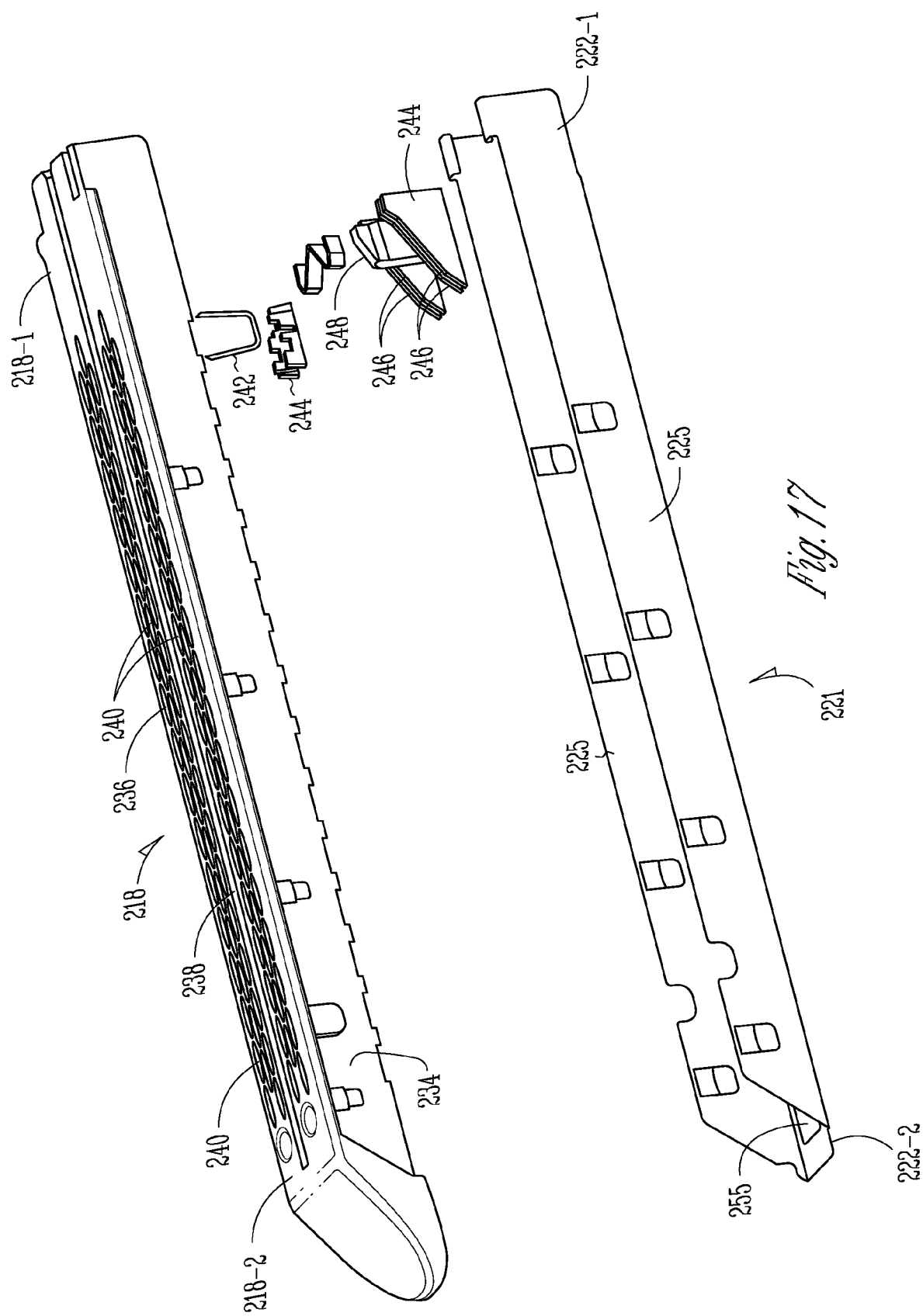

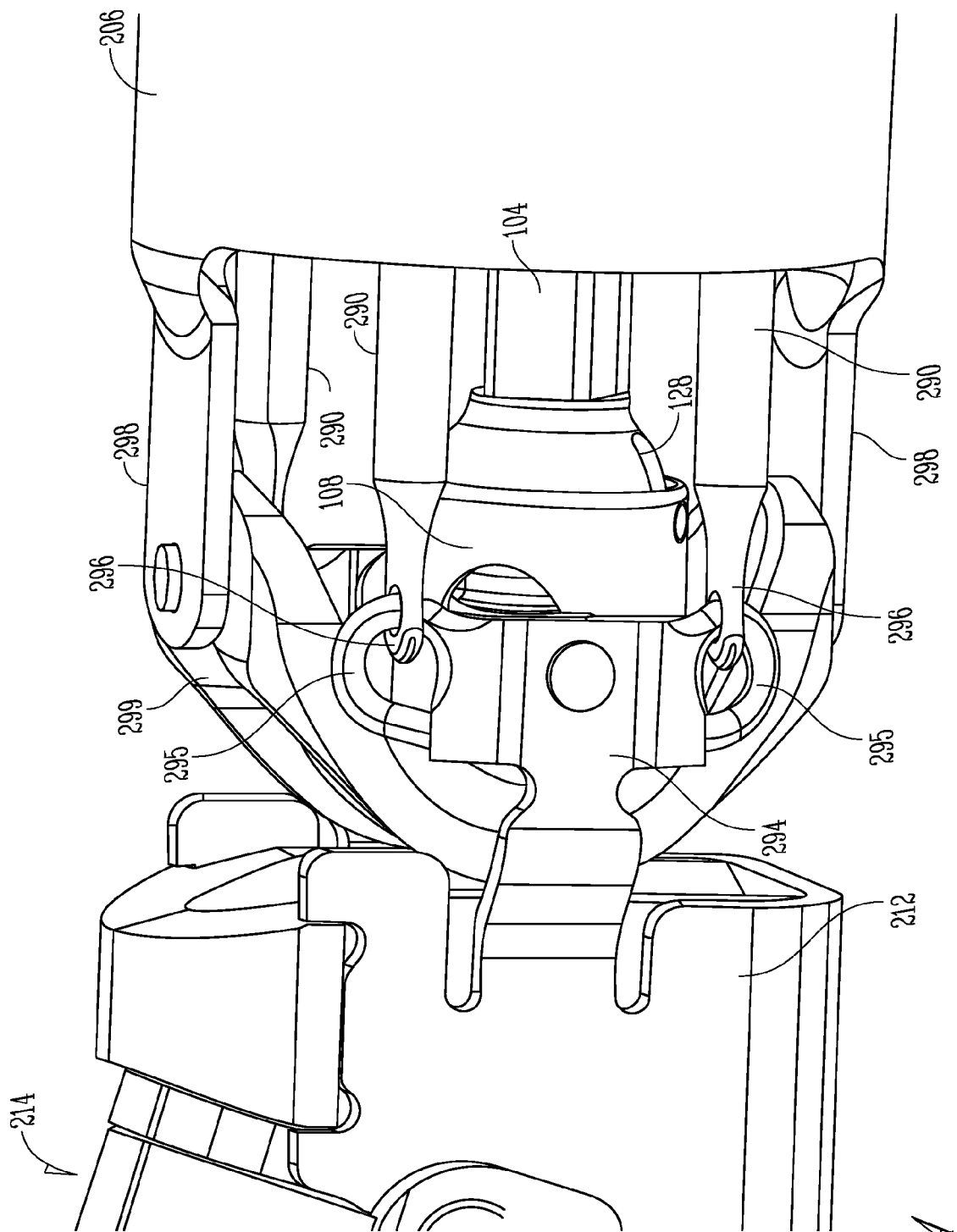

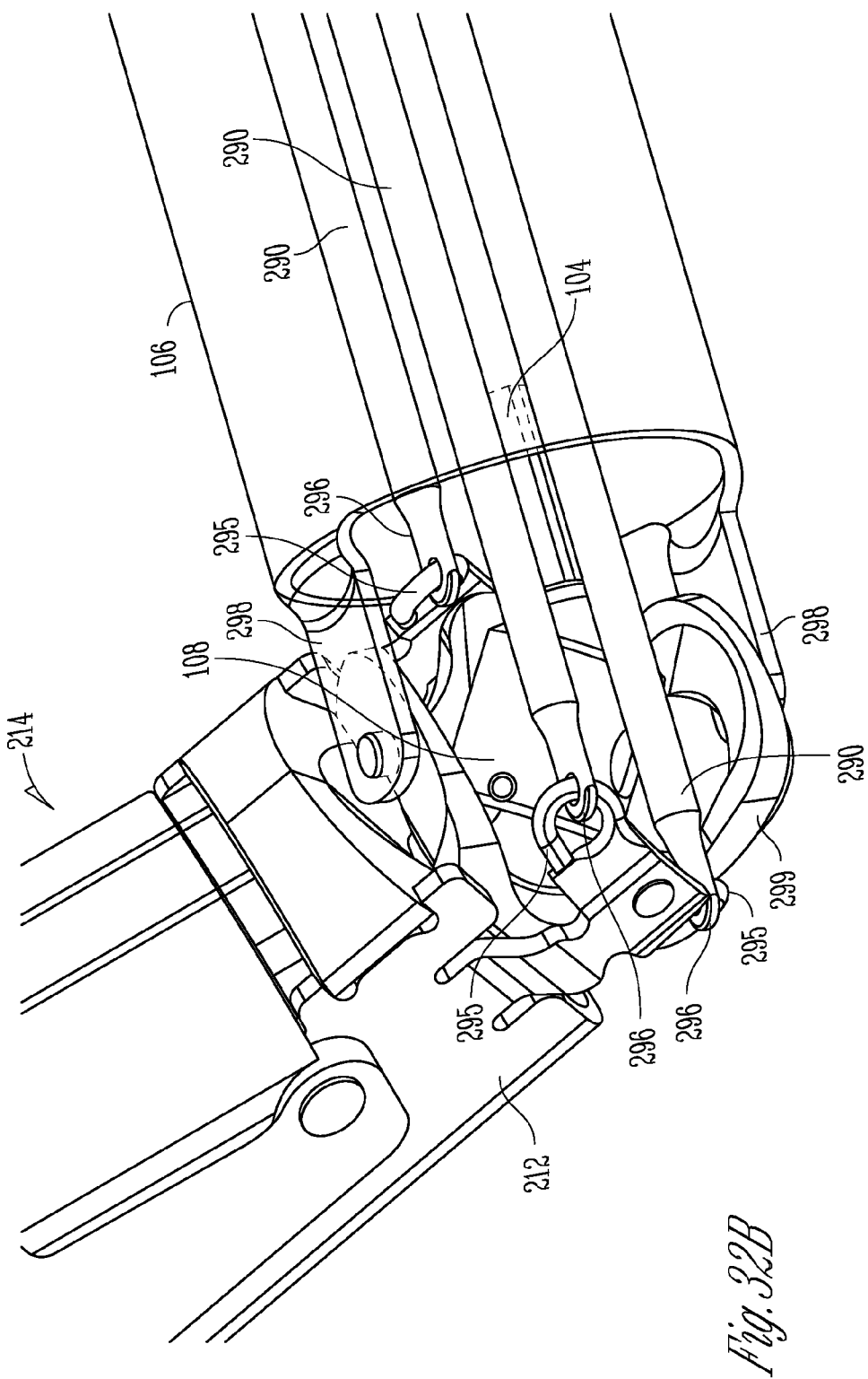

STAPLER WITH COMPOSITE CARDAN AND SCREW DRIVE

RELATED APPLICATIONS

This patent application is a divisional of and claims the benefit of priority under 35 U.S.C. § 120 to U.S. patent application Ser. No. 15/772,527, filed on Apr. 30, 2018, which is a U.S. National Stage Filing under 35 U.S.C. 371 from International Application No. PCT/US2016/059527, filed on Oct. 28, 2016, and published as WO 2017/083125 A1 on May 18, 2017, which claims priority to and the benefit of the filing date of U.S. Provisional Patent Application 62/255,123, entitled "STAPLER WITH COMPOSITE CARDAN AND SCREW DRIVE" filed Nov. 13, 2015, each of which is incorporated by reference herein in its entirety.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

Minimally invasive teleoperated surgical systems have been developed to increase a surgeon's dexterity when working on an internal surgical site, as well as to allow a surgeon to operate on a patient from a remote location (outside the sterile field). In a teleoperated surgical system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the teleoperated surgical system can provide mechanical actuation and control of a variety of surgical instruments or tools having end effectors that perform various functions for the surgeon, for example, holding or driving a needle, grasping a blood vessel, dissecting tissue, stapling tissue, or the like, in response to manipulation of the master input devices.

SUMMARY

In one aspect, a surgical instrument a surgical instrument includes a first jaw having a first jaw axis and that includes a proximal portion pivotally mounted to a base to be pivotable about a pivot axis between an open and a closed positions and including a distal portion. A second jaw has a second jaw axis and includes a proximal portion secured to the base and includes a distal portion. A first cam surface secured to the first jaw that includes a distal cam portion that extends parallel to the first jaw axis and a proximal cam portion that is inclined at an angle relative to the distal cam portion. A second cam surface secured to the second jaw that extends parallel to the second jaw axis. A drive member includes a cross-beam, which is sized to slideably engage the first and second cam surfaces, a first transverse beam portion, and a second transverse beam portion. A lead screw configured to advance the drive member in a distal direction parallel to the second jaw axis. While the first jaw is in the open position, the distal cam portion and the second cam surface are disposed to contact the first and second transverse beam portions, respectively, and the distal cam portion is disposed to impart a rotational force to the first jaw about the pivot axis as the lead screw advances the drive member in the distal direction. While the first jaw is in the closed position, the proximal cam portion and the second cam surface are disposed, to contact the first and second transverse beam portions, respectively, and to impart a clamp force to the first and second jaws as the lead screw advances the drive member in the distal direction.

In another aspect, a universal double joint includes a first rotatable bearing has a first spherical surface formed of a plastic material. At least one first metal pin is configured to receive the imparted drive force and to impart the imparted drive force to the first rotatable bearing. A second rotatable bearing has a second spherical surface formed of a plastic material. At least one second metal pin configured to receive the imparted drive force and to impart the imparted drive force to the second rotatable bearing.

BRIEF DESCRIPTION OF DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 15 is an illustrative perspective drawing, with a partial cutaway, of a surgical tool assembly in accordance with some embodiments.

FIG. 16 is an illustrative perspective view, with a partial cutaway, of the end effector of FIG. 9 with an empty second jaw from which the stapler cartridge is removed in accordance with some embodiments.

FIG. 17 is an illustrative exploded view of a detachable stationary second jaw in accordance with some embodiments.

FIGS. 32A-32B are illustrative drawings showing details of a two degree of freedom wrist of the end effector with the torque transmitting mechanism in an inline position (FIG. 32A) and in a articulated position (FIG. 32B) in accordance with some embodiments.

DESCRIPTION OF EMBODIMENTS

Figure 1:
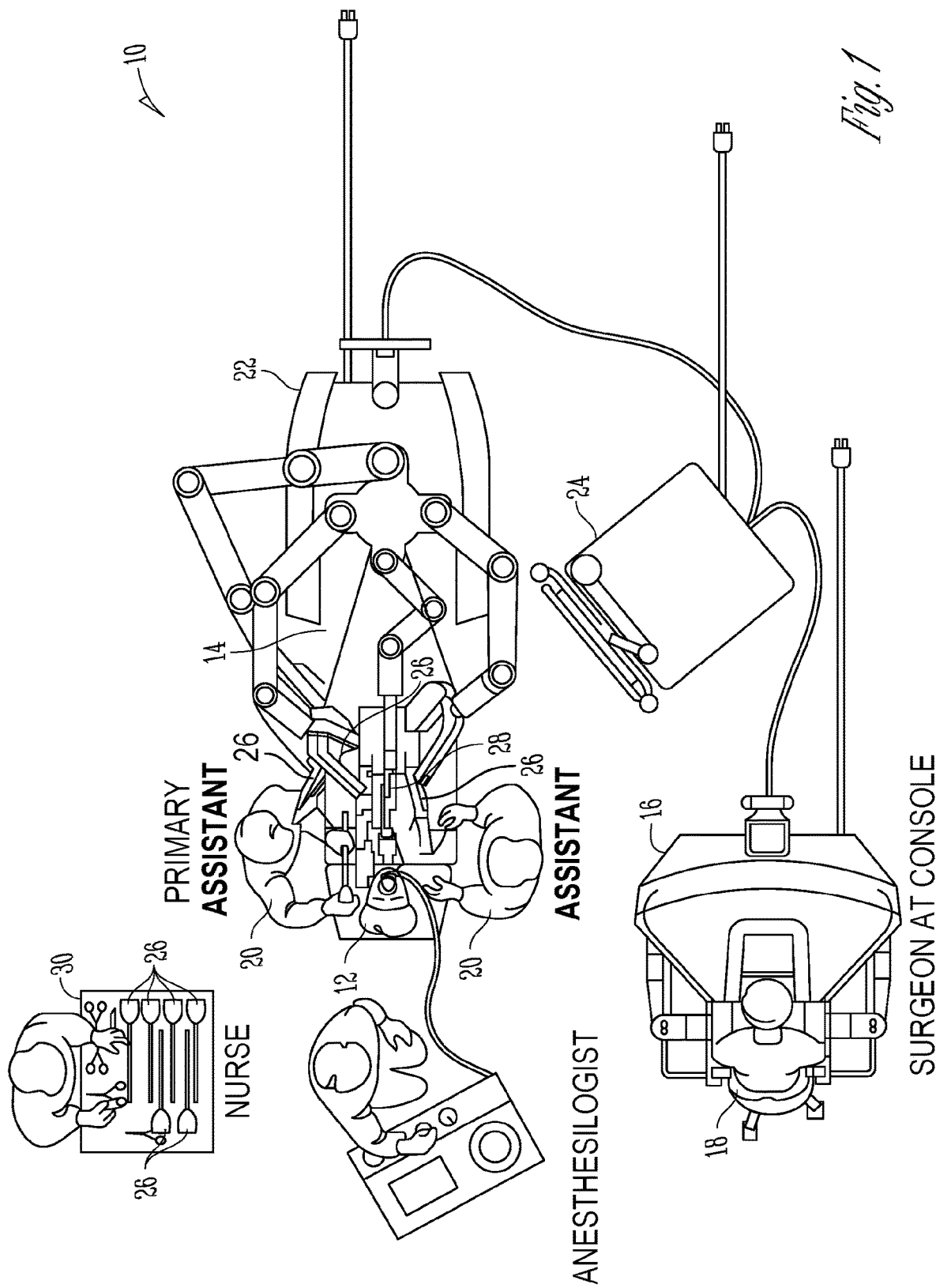
FIG. 1 is an illustrative plan view illustration of a teleoperated surgical system in accordance with some embodiments.

The following description is presented to enable any person skilled in the art to create and use a stapler with composite cardan and lead screw drive for use in a surgical system. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Referring now to the drawings, in which like reference numerals represent like parts throughout the several views, FIG. 1 is an illustrative plan view of a teleoperated surgical system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The teleoperated surgical system 10 can further include a Patient Side Cart 22 and an Electronics Cart 24. The Patient Side Cart 22 can manipulate at least one removably coupled tool assembly 26 (hereinafter also referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors.

Figure 2:
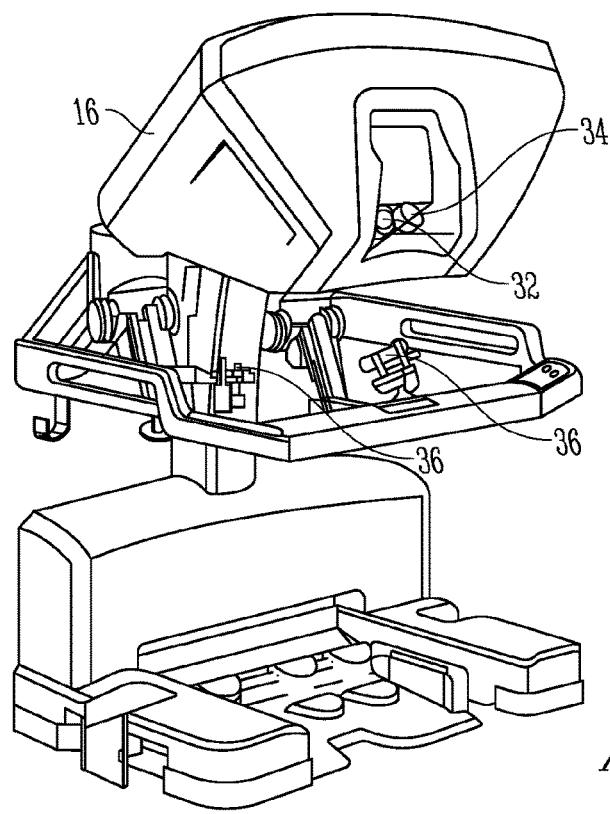
FIG. 2 is an illustrative perspective view of the Surgeon's Console in accordance with some embodiments.

FIG. 2 is an illustrative perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

Figure 3:
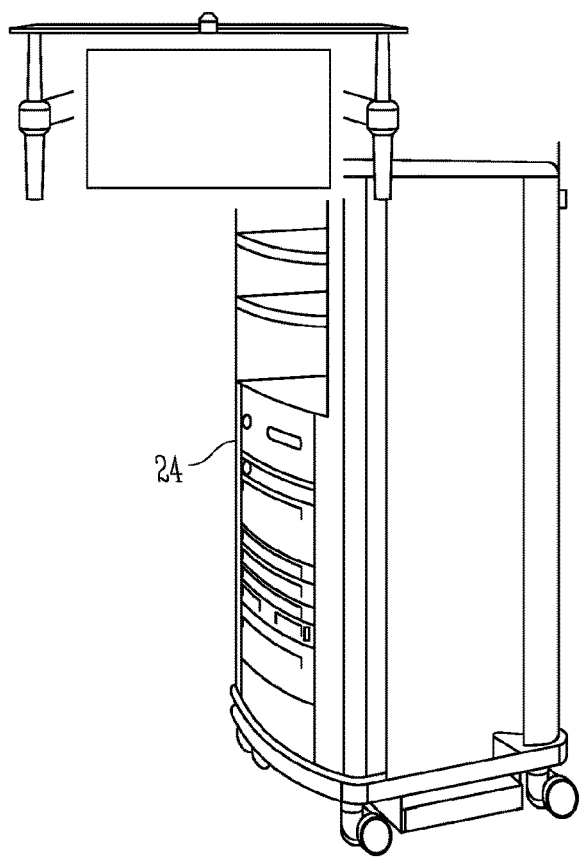
FIG. 3 is an illustrative perspective view of the Electronics Cart in accordance with some embodiments.

FIG. 3 is an illustrative perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope.

Figure 4:
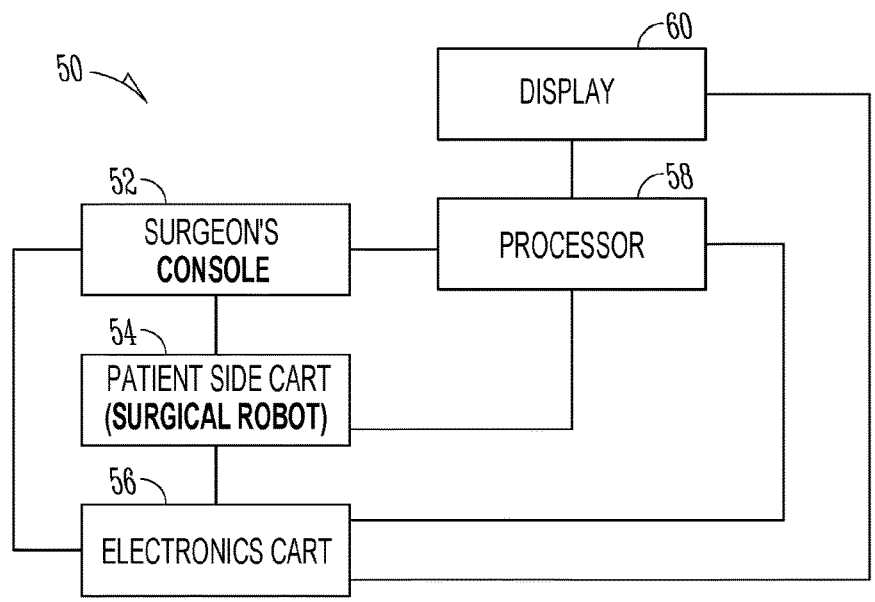
FIG. 4 is an illustrative bock diagram diagrammatically representing functional relationships among components of a teleoperated surgery system in accordance with some embodiments.

FIG. 4 is an illustrative bock diagram diagrammatically representing functional relationships among components of a teleoperated surgery system 50 (such as system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
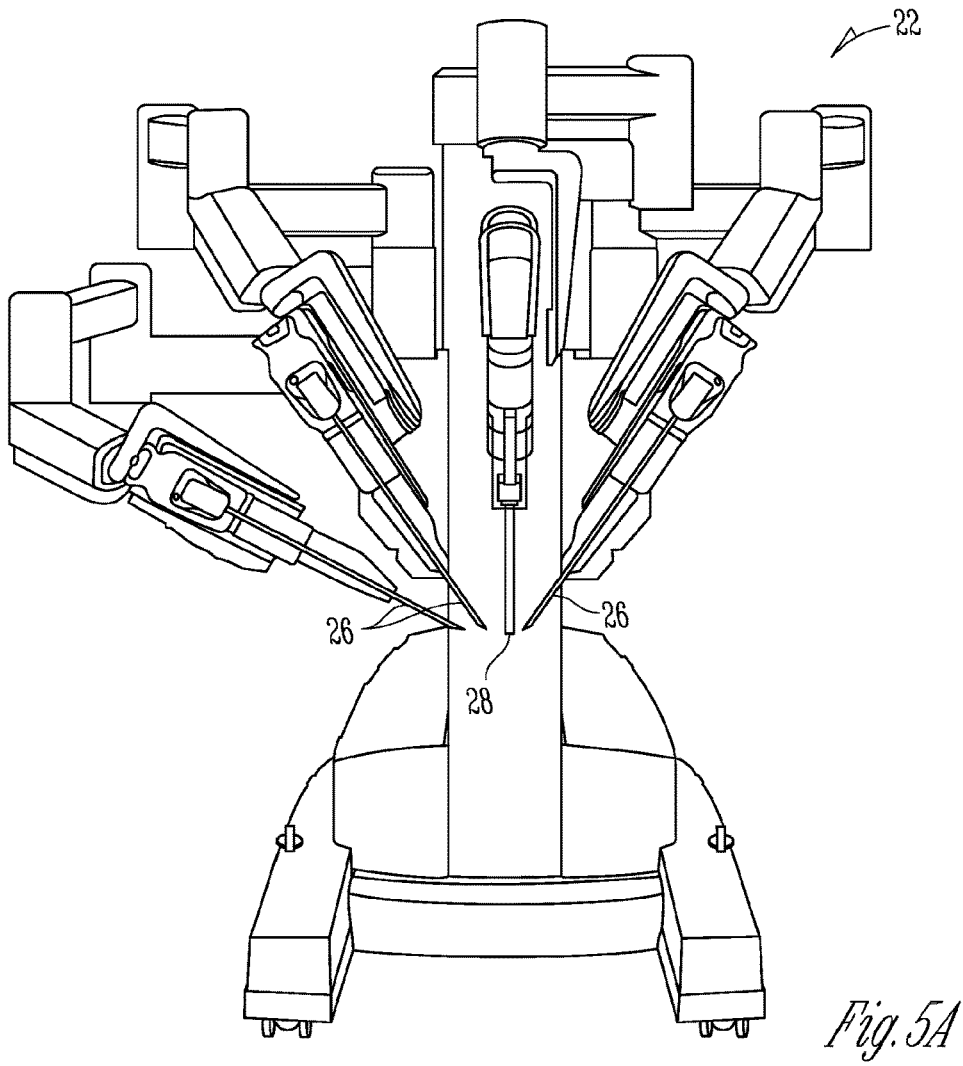
FIGS. 5A-5B are illustrative drawings showing a Patient Side Cart and a surgical tool 62, respectively in accordance with some embodiments.
Figure 5B:
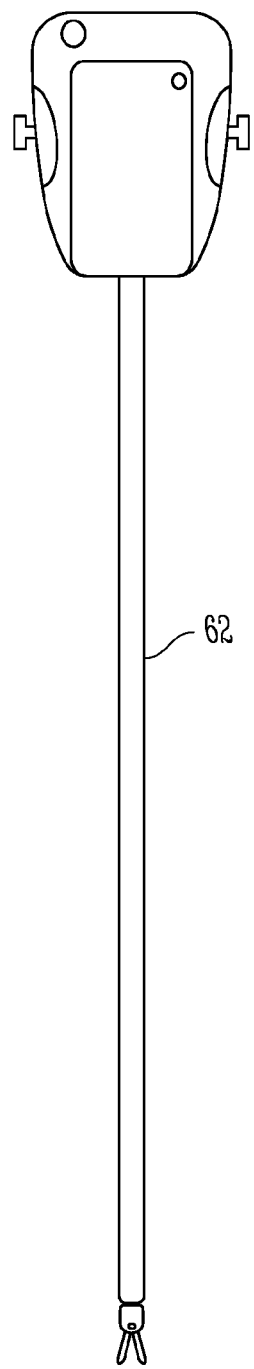

FIGS. 5A-5B are illustrative drawings showing a Patient Side Cart 22 and a surgical tool 62, respectively in accordance with some embodiments. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by teleoperated mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Figure 6:
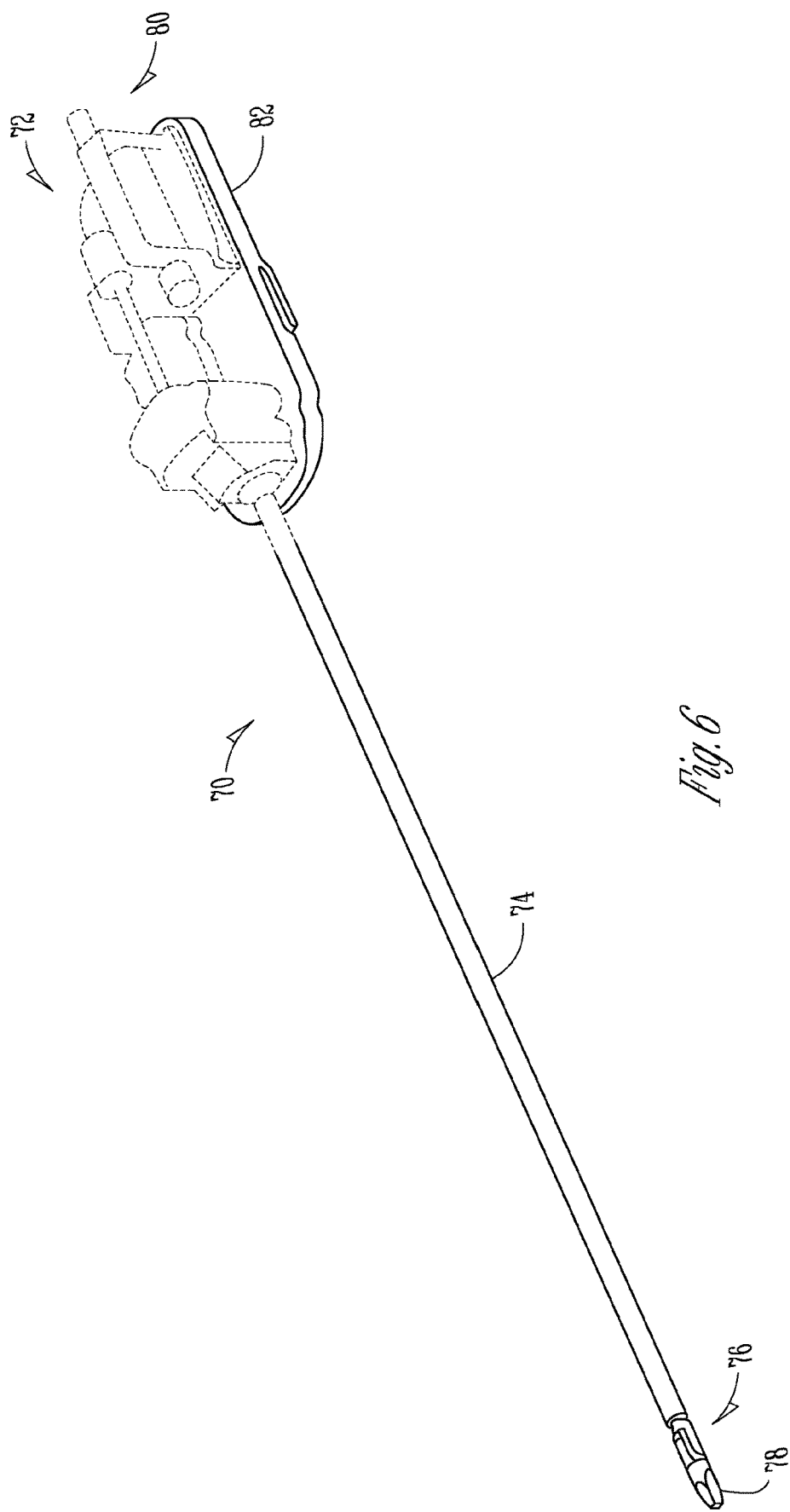
FIG. 6 is an illustrative drawing showing an example surgical tool in accordance with some embodiments.

FIG. 6 is an illustrative drawing showing an example surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Figure 7:
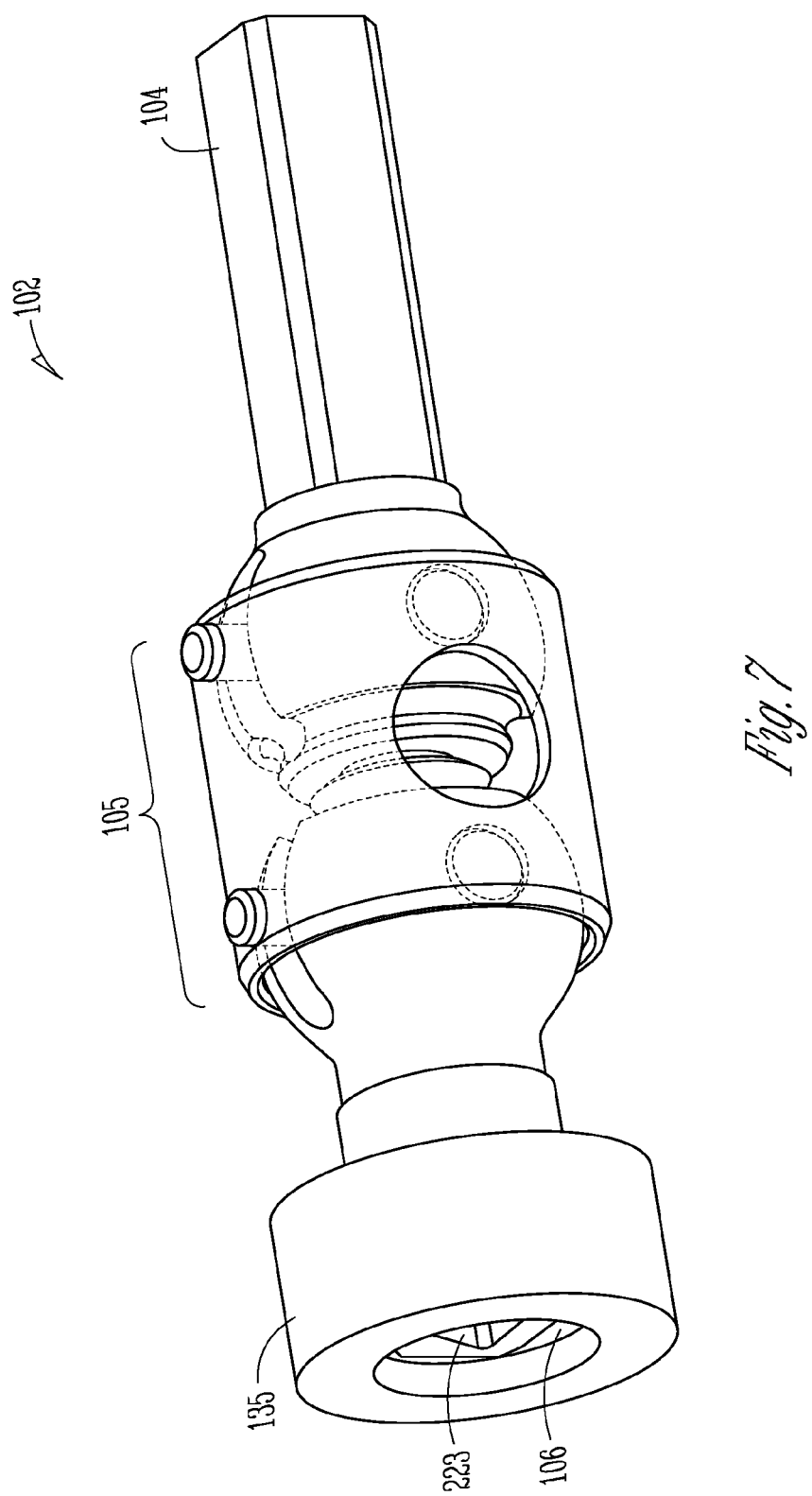
FIG. 7 is perspective view of a portion of a torque transmitting mechanism for transmitting torque through an angle, in accordance with some embodiments.

FIG. 7 is perspective view of a portion of a torque transmitting mechanism102 for transmitting torque through an angle, in accordance with some embodiments. The torque transmitting mechanism 102 includes cardan drive shaft 104 and a cardan driven shaft 106 and a double universal joint 105, also referred to herein as a cardan joint, in accordance with some embodiments. A cardan shaft is a shaft that has a universal joint at one or both ends enabling it to rotate freely when in varying angular relation to another shaft or shafts to which it is joined. A cardan joint is a universal joint in a shaft that enables the shaft to rotate together with another shaft to which it is joined when the two shafts are out of axial alignment. U.S. Pat. No. 8,852,174 (filed Nov. 12, 2010) issued to Burbank, which is incorporated herein in its entirety by this reference, discloses prior surgical tolls that include two degree of freedom wrists and double universal joints.

Figure 8:
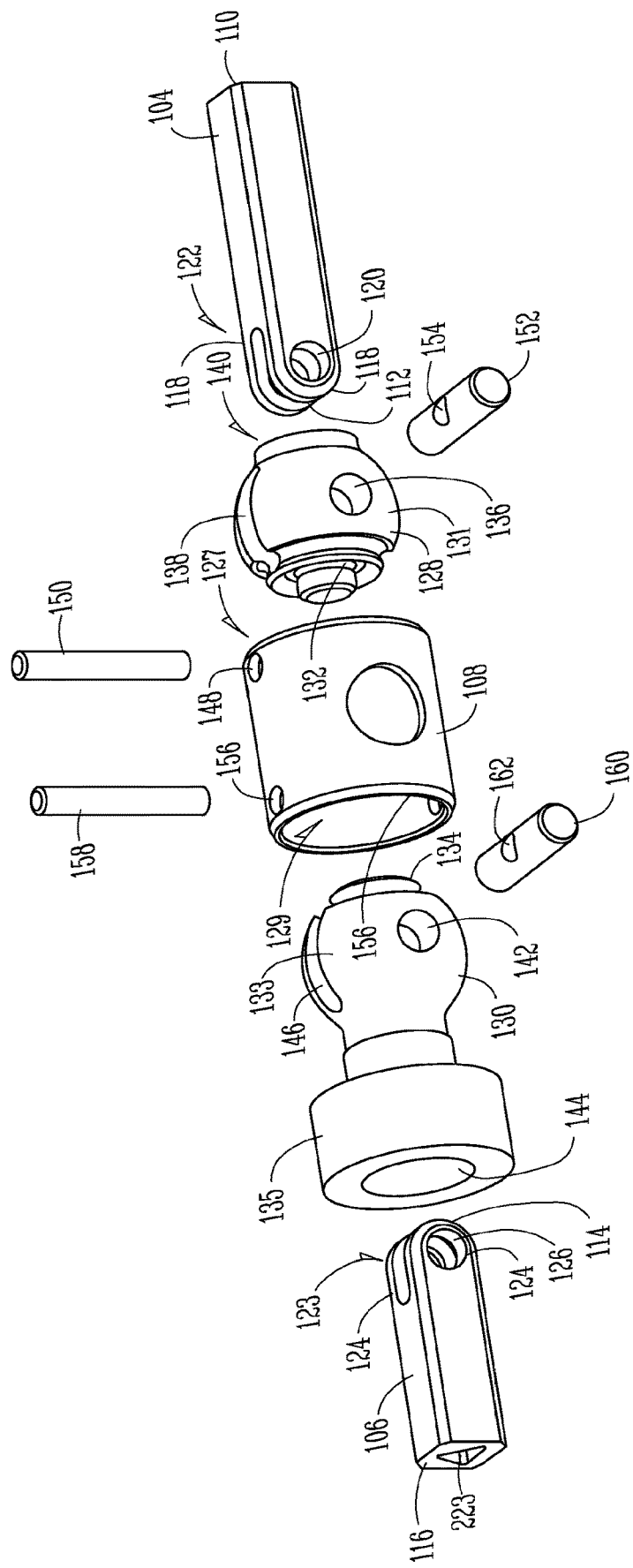
FIG. 8 is an exploded perspective view of the torque transmitting mechanism of FIG. 1 in accordance with some embodiments.

FIG. 8 is an exploded perspective view of the torque transmitting mechanism 102 of FIG. 7. The torque transmitting mechanism 102 includes a drive shaft 104, a driven shaft 106 and a metal coupling member 108 disposed between them. The drive shaft 104, the driven shaft 106, or both drive shaft 104 and driven shaft 106, may comprise metal. The drive shaft 104 includes a proximal end 110 and a distal end 112. The driven shaft 106 includes a proximal end 114 and a distal end 116. The distal end 112 of the drive shaft 104 includes opposed facing arms 118 with holes 120 that are aligned to define a drive axis clevis 122. The proximal end 114 of the driven shaft 106 includes opposed facing arms 124 with holes 126 that are aligned to define a drive axis clevis 123.

The metal coupling member 108 comprises a generally cylindrical sleeve structure that defines a proximal end opening 127 and a distal end opening 129. A drive shaft plastic bearing 128 having a partially spherical outer surface portion 131 is sized to fit within the proximal end opening 127 for smooth partial rotation therein. A driven shaft plastic bearing 130 having a partially spherical outer surface portion 133 is sized to fit within the distal end opening 130 for smooth partial rotation therein.

The drive shaft plastic bearing 128 defines a proximal plastic axial engagement structure 132 and the driven shaft plastic bearing 130 defines a complementary distal plastic axial engagement structure 134. The proximal plastic axial engagement structure 132 and the distal axial engagement structure 134 have complementary shapes that cooperate during axial rotation of the drive shaft 104 and the driven shaft 106 to tie the relative angular orientation between the drive shaft 104 and the coupling member 108 to the relative angular orientation between the driven shaft 106 and the coupling member 108. More particularly, the proximal plastic axial engagement structure 132 and the distal axial engagement structure 134 cooperate to constrain the coupling member 108 to be oriented at an equivalent relative angle to both the drive shaft 104 and the driven shaft 106, such that any rotational speed differences between the drive shaft 104 and the coupling member 108 are effectively canceled when the rotation of the coupling member 108 is transferred to the driven shaft 106, thereby substantially eliminating rotational speed differences between the drive shaft 104 and the driven shaft 106. A torque transmitting mechanism for transmitting torque through an angle while substantially eliminating rotational speed differences between a drive shaft 104 and a driven shaft 106 is commonly referred to as a constant velocity (CV) joint. In accordance with some embodiments, the proximal plastic axial engagement structure 132 includes a first plastic spherical gear structure and the distal axial engagement structure 134 includes a first plastic spherical gear structure.

The first drive shaft plastic bearing 128 defines a proximal transverse bore 136 extending through the partially spherical outer surface portion 131 transverse to the first plastic engagement structure 132. The first drive shaft plastic bearing 128 defines a proximal opening 140 sized to permit passage of the drive axis clevis 122 so as to align holes 120 with the proximal transverse bore 136. The first drive shaft plastic bearing 128 defines a proximal transverse slot 138 that extends through the partially spherical outer surface portion 131 at a right angle to the transverse bore 136. The proximal transverse slot 138 extends through a partial circumference of the first drive shaft plastic bearing 128 having an axis aligned with an axis of the proximal transverse bore 136.

The second drive shaft plastic bearing 130 defines a distal transverse bore 142 extending through the partially spherical outer surface portion 133 transverse to the second plastic engagement structure 130. The driven shaft plastic bearing 130 is secured to a distal hub 135 used to mount to the proximal portion of the end effector (described below). The driven shaft plastic bearing 130 is secured to a distal hub 135 define a distal opening 144 sized to permit passage of the driven axis clevis 123 so as to align holes 126 with the distal transverse bore 142. The second drive shaft plastic bearing 130 defines a distal transverse slot 146 that extends through the partially spherical outer surface portion 133 at a right angle to the distal transverse bore 146. The distal transverse slot 146 extends through a partial circumference of the second drive shaft plastic bearing 130 having an axis aligned with an axis of the distal transverse bore 142.

The metal coupling member 108 defines opposed diametrically aligned proximal holes 148 extending through it adjacent its proximal end opening 127. The first drive shaft plastic bearing 128 is inserted within the proximal end opening 127, with the proximal end holes 148 aligned with the proximal transverse slot 138. A proximal coupling pin 150 extends through the aligned proximal end holes 148 and the proximal transverse slot 138 and is matingly secured to opposed inner surfaces of the coupling member 108 to permit rotation of the first drive shaft plastic bearing 128 about an axis of the proximal coupling pin 150. A proximal cross pin 152 defines a proximal cross pin bore 154 that extends therethrough. The proximal cross pin 152 extends through the proximal transverse bore 136 and is secured therein to permit rotation of the first drive shaft plastic bearing 128 about the axis of the proximal cross pin 152. The proximal cross pin bore 154 is sized to permit passage of the proximal coupling pin 150, which extends through it and has opposed ends secured to diametrically opposed sides of the metal coupling member 108. Thus, the proximal coupling pin 150 and the proximal cross pin 152 maintain a perpendicular, cross, relationship with each other.

The metal coupling member 108 defines opposed diametrically aligned distal openings 156 extending through it adjacent its distal end opening 129. The second drive shaft plastic bearing 130 is inserted within the distal end opening 129, with the distal end holes 156 aligned with the distal transverse slot 146. A distal coupling pin 158 extends through the aligned proximal end openings 156 and the proximal transverse slot 146 and is matingly secured to opposed inner surfaces of the coupling member 108 to permit rotation of the second drive shaft plastic bearing 130 about an axis of the distal coupling pin 156. A distal cross pin 160 defines a distal cross pin bore 162 that extends therethrough. The distal cross pin 160 extends through the distal transverse bore 142 and is secured therein to permit rotation of the second drive shaft plastic bearing 130 about an axis of the distal cross pin 160. The distal cross pin bore 162 is sized to permit passage of the distal coupling pin 158, which extends through it and has opposed ends secured to diametrically opposed sides of the metal coupling member 108. Thus, the distal coupling pin 158 and the proximal cross pin 160 maintain a perpendicular, cross, relationship with each other.

Figure 9:
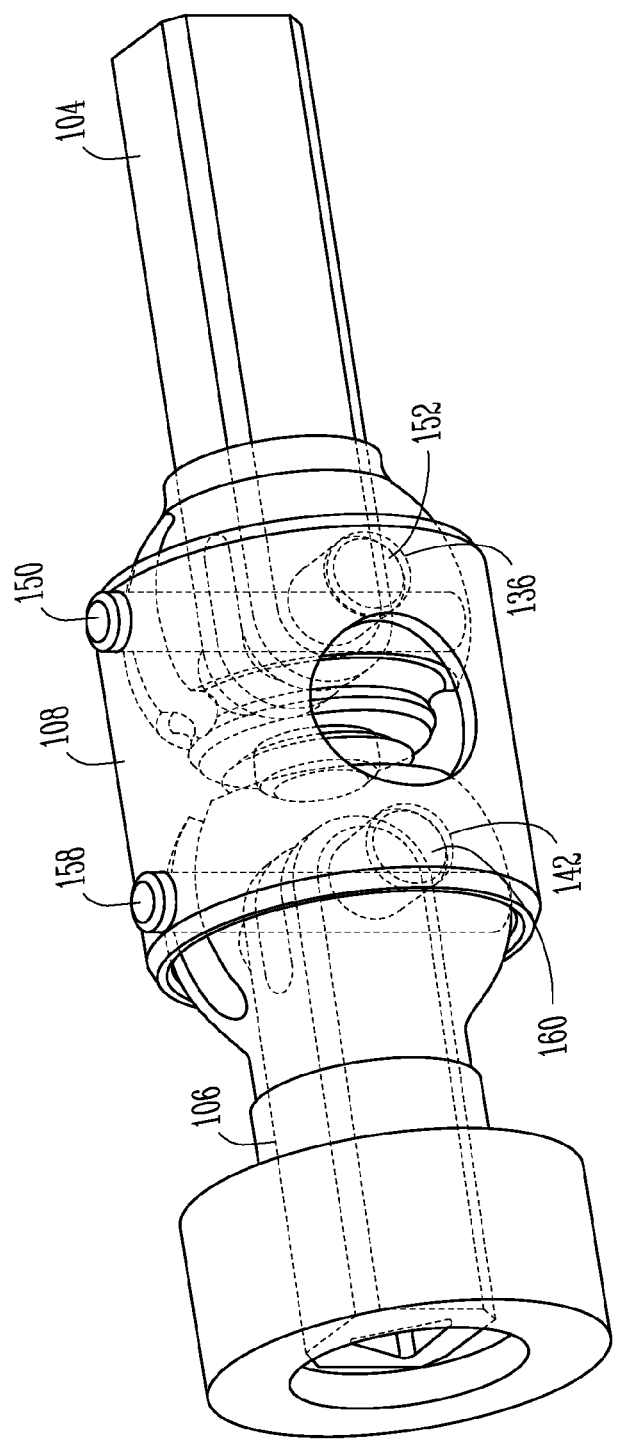
FIG. 9 is a perspective partially cut away view of the torque transmitting mechanism of FIGS. 7-8 shown as assembled in accordance with some embodiments.

FIG. 9 is a perspective partially cut away view of the torque transmitting mechanism of FIGS. 7-8 102 shown as assembled in accordance with some embodiments. The coupling member 108 is shown partially cut away to show the drive shaft plastic bearing 128 and the driven shaft plastic bearing 130 that are partially enclosed within it. A portion of the drive shaft 104 that is encompassed within the drive shaft plastic bearing 128 is illustrated using dashed lines. Similarly, a portion of the driven shaft 106 that is encompassed within the driven shaft plastic bearing 130 is illustrated using dashed lines. FIG. 9 illustrates the torque transmitting mechanism 102 in an inline configuration in which the drive shaft 104 and the driven shaft 106 are longitudinally aligned.

The proximal coupling pin 150, which passes through the proximal cross pin bore 154 formed in the proximal cross pin, is matingly secured within the proximal holes 148 formed on diametrically opposed sides of the coupling member 108 adjacent to its proximal opening 127. Likewise, the distal coupling pin 158, which passes through the distal cross pin bore 162 formed in the distal cross pin 160, is matingly secured within the proximal holes 156 formed on diametrically opposed sides of the coupling member 108 adjacent to its distal opening 129. Moreover, the proximal cross pin 152 is extends within and is rotatable relative to the holes 120 formed in the opposed facing arms 118 of the drive axis clevis 122 and extends within and is rotatable relative to the proximal transverse bore 136. Likewise, the distal cross pin 160 extends within and is rotatable relative to the holes 126 formed in the opposed facing arms 124 of the driven axis clevis 123 and extends within and is rotatable relative to the distal transverse bore 142.

Accordingly, the proximal cross pin 152 rotates about the drive shaft axis in unison with the drive shaft 104. Similarly, the driven axis rotates about the driven axis in unison with the distal cross pin 160.

The perpendicular cross mounting of the proximal coupling pin 150 to the proximal cross pin 152 imparts to the coupling pin 150, rotation forces about the drive shaft axis that are imparted to the cross pin 152 due to rotation of the drive shaft 104. Since the proximal coupling pin 150 and the distal coupling pin 160 each is matingly secured to the metal coupling structure 108, a rotational force imparted to the proximal coupling pin 150 is imparted through the coupling member 108 to the distal coupling pin 158. Moreover, the perpendicular cross mounting of the distal coupling pin 158 to the distal cross pin 160 imparts to the driven shaft 106, rotation forces about the driven shaft axis that have the same magnitude as and that are responsive to rotation forces imparted about the drive shaft axis of the drive shaft 104.

The first drive shaft plastic bearing 128 can move in two degrees of freedom (2-dof). Movement of the first drive shaft plastic bearing 128 in a first degree of freedom involves the first drive shaft plastic bearing 128 rotating about the axis of the proximal cross pin 152 with the proximal coupling pin 150, which is in a fixed position relative to the coupling member 108, sliding within the proximal transverse slot 138. Movement of the first drive shaft plastic bearing 128 in a second degree of freedom involves the bearing 128 about the proximal coupling pin 150, which is in a fixed position relative to the coupling member 108.

Likewise, the second drive shaft plastic bearing 130 can move in two degrees of freedom (2-dof). Movement of the second drive shaft plastic bearing 130 in a first degree of freedom involves the second drive shaft plastic bearing 130 rotating about the axis of the distal cross pin 160 with the distal coupling pin 158, which is in a fixed position relative to the coupling member 108, sliding within the distal transverse slot 146. Movement of the second drive shaft plastic bearing 130 in a second degree of freedom involves the bearing 130 rotating about the distal coupling pin 158, which is in a fixed position relative to the coupling member 108.

Figure 10A:
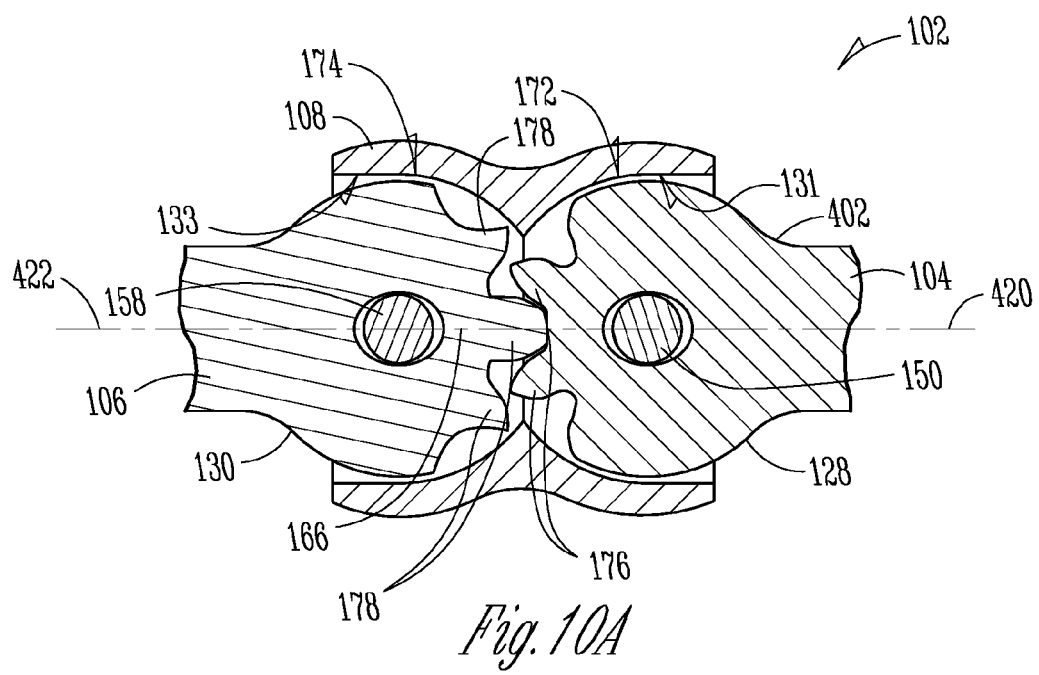
FIG. 10A is illustrative cross-sectional view of the torque transmitting mechanism of FIGS. 7-9 in an inline position in accordance with some embodiments.

FIG. 10A is illustrative cross-sectional view of the torque transmitting mechanism 102 of FIGS. 7-9 showing details of a drive shaft plastic bearing 128 outer spherical surface 131 interfacing with a first inner spherical surface 172 of the coupling member 108, and also showing details of the driven shaft plastic bearing 130 outer spherical surface 133 interfacing with a second inner spherical surface 174 of the coupling member 108. An advantage of using an outer spherical surface for plastic bearings is lower cost and accuracy of the components, since gear surfaces can be difficult to manufacture accurately from metal, which makes them very costly. With injection molding a more repeatably accurate part can be produced with much lower cost. Moreover, the plastic also can provide some lubrication. As discussed above, the constraint provided by the first coupling pin 150 axially and rotationally couples the drive shaft 104 and the drive shaft plastic bearing 128 mounted thereon, to the coupling member 108, and the constraint provided by the second coupling pin 158 axially and rotationally couples the driven shaft 106 and the driven shaft plastic bearing 130 mounted thereon to the coupling member 108. Additionally, the constraint provided by the interfacing spherical surfaces can further constrain the drive shaft 104 and the driven shaft 106 relative to the coupling member 108.

Figure 10B:
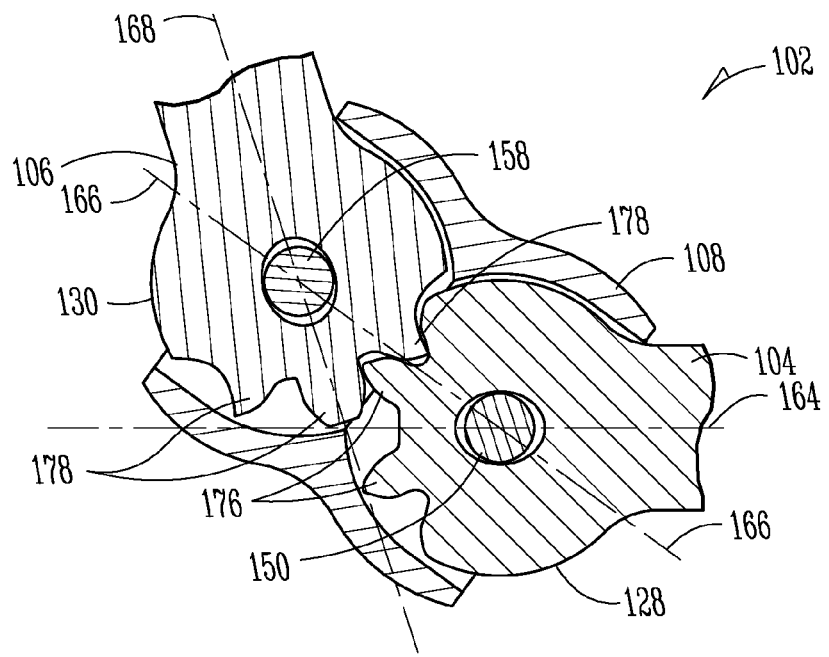
FIG. 10B is illustrative cross-sectional view of the torque transmitting mechanism of FIGS. 7-9 in an articulated position in accordance with some embodiments.

FIG. 10B is an illustrative cross-sectional view of the torque transmitting mechanism 102 of FIGS. 7-10A, illustrating engagement between gear teeth 176 drive shaft plastic bearing 128 and gear teeth 178 of the driven shaft plastic bearing 130 for an angled configuration, in accordance with some embodiments. The cross-section illustrated includes the drive axis 164, the driven axis 168, and the coupling member axis 166, and is taken along a view direction parallel to the axes of the first coupling pin 150 and the second coupling pin 158.

In the angled configuration illustrated in FIG. 10B, the driven axis of the driven shaft 106 deviates from the drive axis of the drive shaft 104 by 70 degrees. The constraint provided by engagement between the drive shaft gear teeth 176 of the drive shaft plastic bearing 128 and the gear teeth 178 of the driven shaft plastic bearing 130 results in the 70 degrees being equally distributed amongst a 35 degree deviation between the drive axis 164 and the coupling axis 166, and a 35 degree deviation between the coupling axis 166 and the driven axis 168. By constraining the coupling member 108 to be oriented at an equivalent relative angle to both the drive shaft 104 and the driven shaft 106, any rotational speed differences between the drive shaft and the coupling member are effectively canceled when the rotation of the coupling member 108 is transferred to the driven shaft 106, thereby substantially eliminating any rotational speed differences between the drive shaft 104 and the driven shaft 106.

In some embodiments, the gear teeth 176 of the drive shaft plastic bearing 128 and the gear teeth 178 of the driven shaft plastic bearing 130 are spherically oriented so as to provide the above described constraint between the drive shaft 104 and the driven shaft 106 for any angular orientation of the torque transmitting mechanism 102. For an angled configuration, rotation of the drive shaft 104 and a corresponding rotation of the driven shaft 106 causes different portions of the gear teeth 176 of the drive shaft plastic bearing 128 and the gear teeth 178 of the driven shaft plastic bearing 130 to be intersected by the coupling axis 108. The use of spherical gear teeth allows this movement of the shafts while still providing the angular constraint necessary to orient the coupling member relative to the drive shafts.

Figure 11:
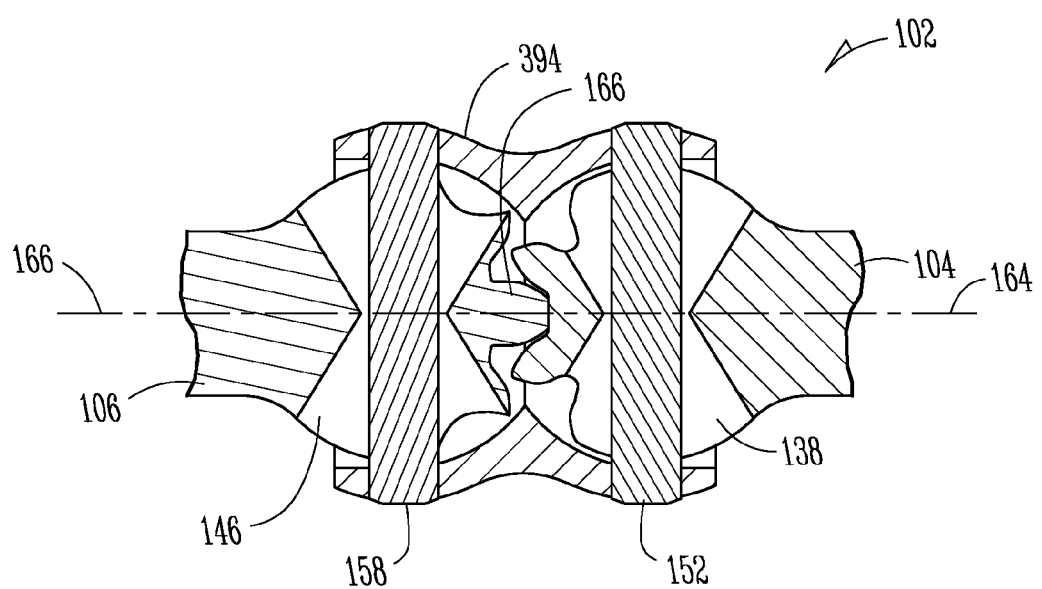
FIG. 11 is an illustrative cross-sectional view of the torque transmitting mechanism of FIGS. 7-10B, illustrating the configuration of the proximal and distal transverse slots in accordance with many embodiments.

FIG. 11 is an illustrative cross-sectional view of the torque transmitting mechanism 102 of FIGS. 7-10B, illustrating the configuration of the proximal transverse slot 138 and the similar distal transverse slot 146, in accordance with many embodiments. The proximal transverse slot 138 is configured to accommodate the first coupling pin 150 throughout a range of angles between a drive axis 164 and a coupling axis 166. Likewise, the distal transverse slot 146 is configured to accommodate the second coupling pin 158 throughout a range of angles between the driven axis 168 and the coupling axis 166. When the torque transmitting mechanism 102 is operated in an angled configuration, the position of the first coupling pin 150 within the proximal transverse slot 138 will undergo a single oscillation cycle for each 360 degree rotation of the drive shaft 104. Likewise, the position of the second coupling pin 158 within the distal transverse slot 146 will undergo a single oscillation cycle for each 360 degree rotation of the driven shaft 106.

Figure 12A:
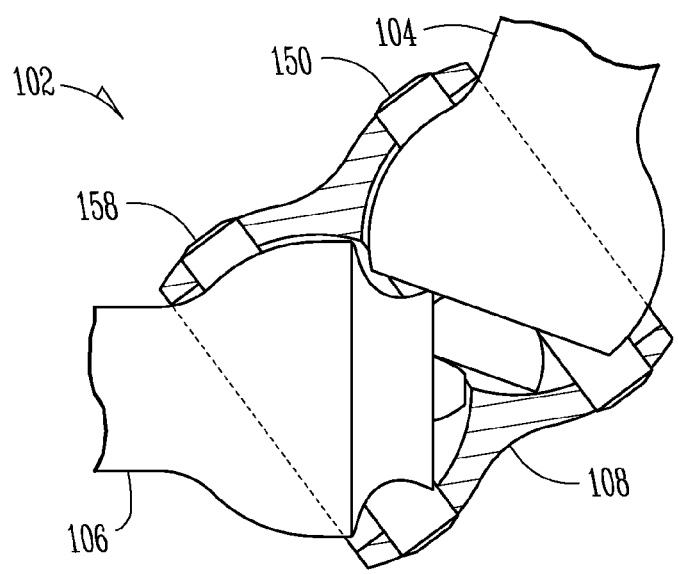
FIG. 12A is an illustrative side elevation view of a torque transmitting mechanism along a view direction normal to the axes of coupling pins in accordance with some embodiments.
Figure 12B:
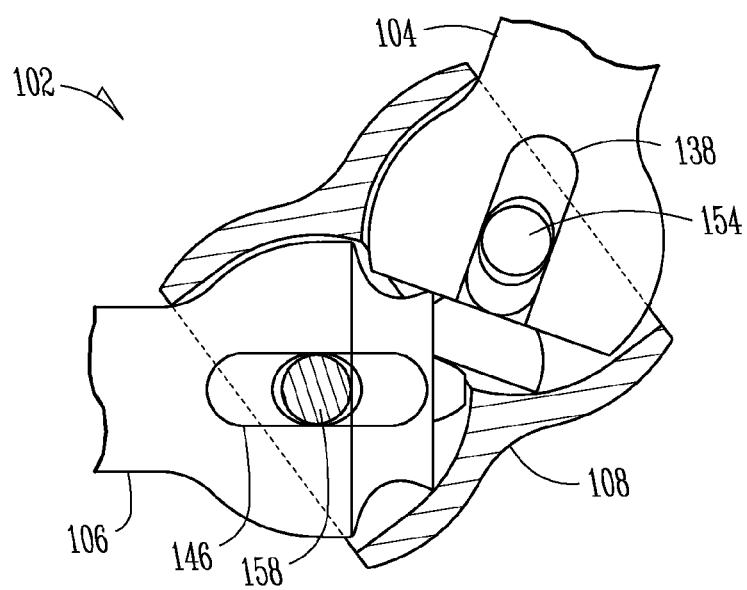
FIG. 12B is an illustrative side elevation view of a torque transmitting mechanism along a view direction parallel to the axes of coupling pins in accordance with some embodiments.

The oscillation of the metal coupling pins 150, 158 within the transverse slots 138, 146 can be described with reference to FIGS. 12A-12B. FIG. 12A is an illustrative side elevation view of the torque transmitting mechanism 102 along a view direction normal to the axes of the coupling pins 150, 158. FIG. 12B is an illustrative side elevation view of torque transmitting mechanism 102 along a view direction parallel to the axes of metal coupling pins 150, 158. In FIGS. 12A-12B, the coupling member 108 is transparent and indicated with dashed lines to illustrate interactions between mechanism components. In the position shown in FIG. 12A, to accommodate the angle between the drive shaft 104 and the coupling member 108, the first coupling pin 150 is canted within the proximal transverse slot 138 (this can be visualized by considering the slot shape illustrated in FIG. 11 in conjunction with the shaft angles illustrated in FIG. 12A). In FIG. 12B, the coupling member 108 has an angular orientation that is 90 degrees from the coupling member orientation of FIG. 12A, thereby aligning the metal coupling pins 150, 158 with the view direction. For the orientation shown in FIG. 12B, the metal coupling pins 150, 158 are not canted within the respective proximal and distal transverse slots 138, 146 (similar to FIG. 11). During a 360 degree revolution of the torque transmitting mechanism 102, the position of the metal coupling pins 150, 158 within the respective proximal and distal transverse slots 138, 146 will complete an oscillation cycle. As explained above, advantages of using plastic include reduced cost and repeatability of manufacturing. In addition, plastic can provide an interface having less friction. Furthermore, plastic can be more forgiving than metal if there is some small amount of interference. The use of plastic also could eliminate the need for lubrication.

Figure 13:
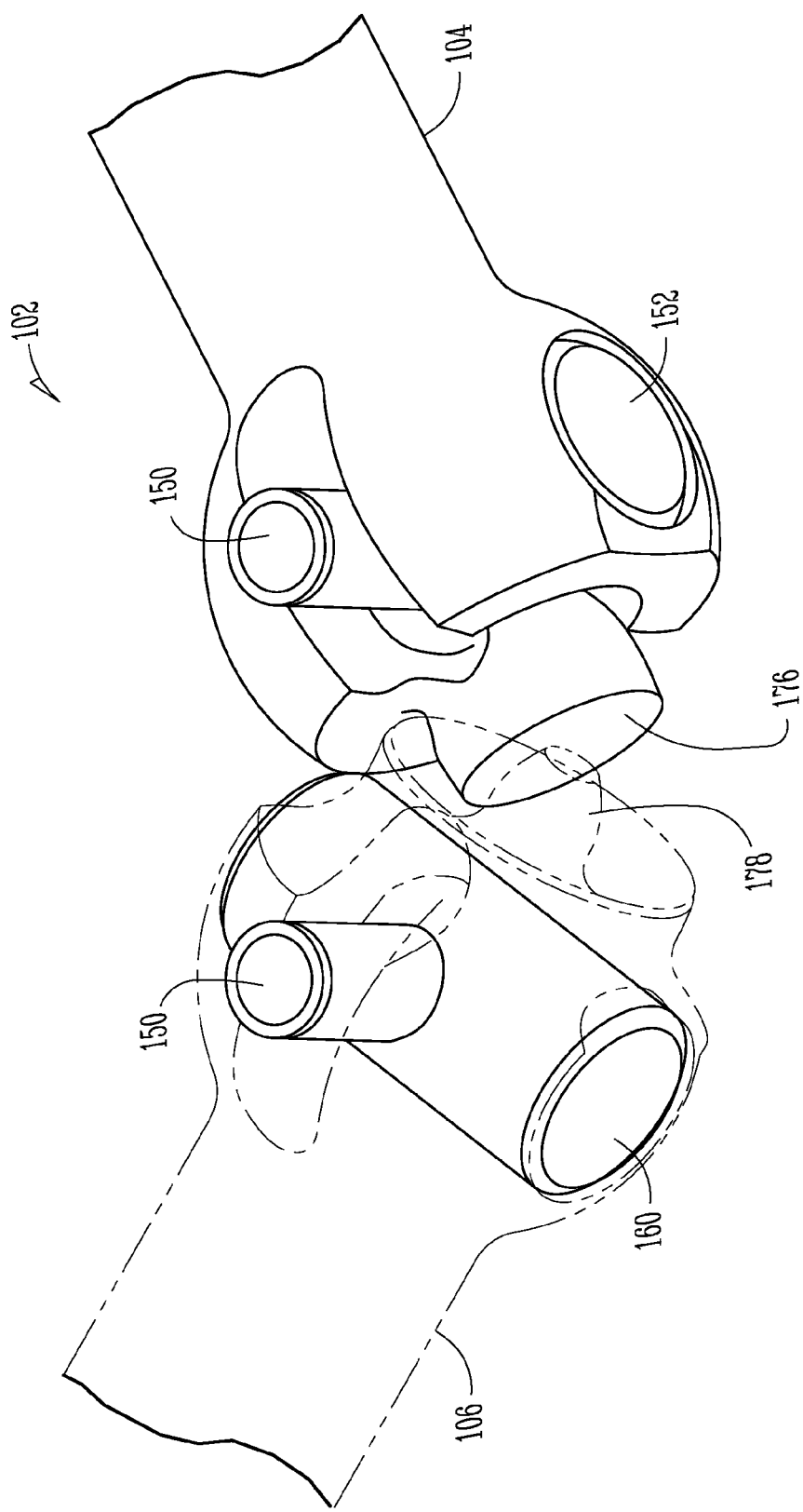
FIG. 13 is an illustrative drawing shows a portion of a torque transmitting mechanism with the coupling member removed and a "see through" driven shaft plastic bearing to show the cross mounting of a distal coupling pin to a distal cross pin in accordance with some embodiments.

FIG. 13 is an illustrative drawing shows a portion of the torque transmitting mechanism 102 with the coupling member 108 removed and a "see through" driven shaft plastic bearing 130 to better illustrate the cross mounting of the distal coupling pin 158 to the distal cross pin 160. The distal metal cross pin 160 is received within the distal transverse bore 142 of the driven shaft plastic bearing 130 and is rotatable within the distal transverse bore 142. The distal coupling pin 158 is received within the distal cross pin bore 162 of the distal metal cross pin 160. Relative rotation between the driven shaft 106 and the coupling member 108 about the centerline of the coupling pin 400 occurs via rotation of the distal coupling pin 158 relative to the coupling member 108 and/or rotation of the distal coupling pin 158 relative to the driven shaft metal cross pin 160 and within the distal transverse slot 146. Similarly, the proximal metal cross pin 152 is received within the proximal cross pin bore 136 of the drive shaft plastic bearing 128 and it is rotatable within the proximal transverse bore 136. The proximal coupling pin 150 is received within proximal cross pin bore 154 of the proximal metal cross pin 152. Relative rotation between the drive shaft 104 and the coupling member 108 about the centerline of the proximal coupling pin 150 occurs via rotation of the proximal coupling pin 150 relative to the coupling member 108 and/or rotation of the coupling pin 150 relative to the proximal cross pin 152 and within the proximal transverse slot 138. It will be appreciated that rotational load forces imparted during operation due to changes in shaft misalignment of the drive shaft 104 and the driven shaft 106 advantageously are supported using the metal coupling pins 150, 158 and metal cross pins 152, 160. Thus, the spherical surfaces of the plastic bearing components 128, 130 are not exposed to rotational load forces imparted due to misalignment of the drive shaft 104 and the driven shaft 106.

Figure 14A:
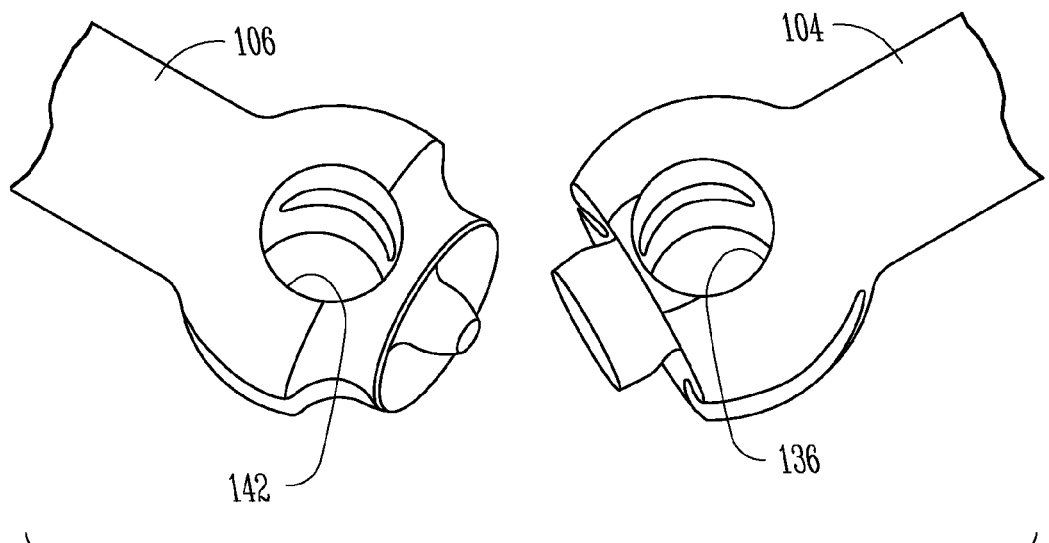
FIG. 14A is an illustrative perspective view showing details of proximal and distal cross pin bores of respective drive shaft plastic bearing and driven shaft plastic bearing in accordance with some embodiments.
Figure 14B:
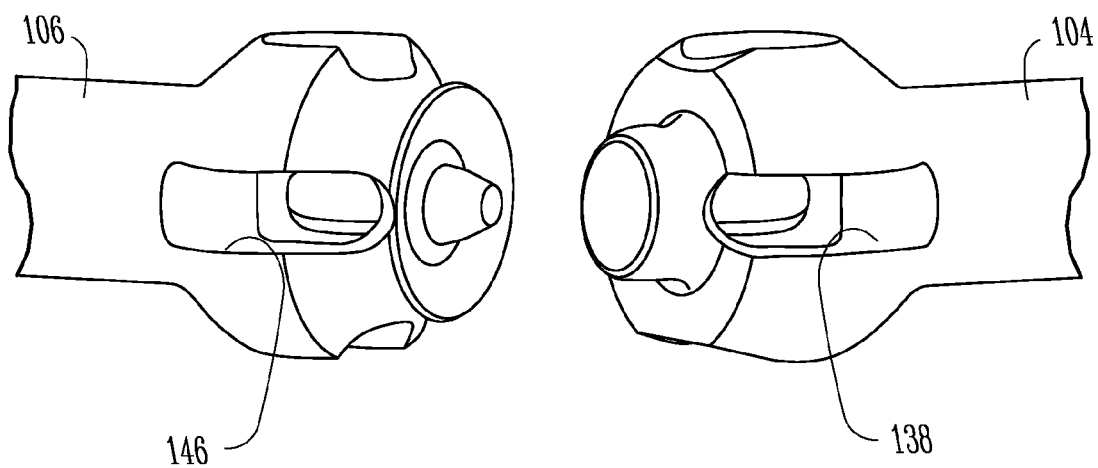
FIG. 14B is an illustrative perspective view showing details of proximal transverse slot and the distal transverse slot of the respective drive shaft plastic bearing and driven shaft plastic bearing in accordance with some embodiments.

FIG. 14A is an illustrative perspective view showing details of the proximal and distal cross pin bores 136, 142 of the respective drive shaft plastic bearing 128 and driven shaft plastic bearing 130 in accordance with some embodiments. FIG. 14B is an illustrative perspective view showing details of the proximal transverse slot 138 and the distal transverse slot 146 of the respective drive shaft plastic bearing 128 and driven shaft plastic bearing 130 in accordance with some embodiments. In accordance with some embodiments, high-strength material is used to produce components that are subject to load forces imparted due to misalignment of the drive shaft 104 and the driven shaft 106 during use. The high strength materials include metal, such as steel or stainless steel, of an appropriate type and strength for the expected loading. The high strength components can be machined or MIM. Materials for 'plastic' can be PPA with Glass or Carbon, PEI (Ultem) with Glass or Carbon, PEEK with glass or carbon fill, PPSU (Radel) with Glass or Carbon fill, for example. The plastics could also have silicone or PTFE filler to help with lubricity. The plastic parts can be injection molded. During assembly, the plastic parts slip over the metal pins and are trapped within the larger diameter pins. The option to MIM the metal components and injection mold the spherical interface components can makes for an affordable option for a cardan in for single patient use devices. The plastic portion can be self-lubricating and reduce friction at the rotation interfaces. A possible tradeoff is strength at the spherical interface.

FIG. 15 is an illustrative perspective drawing, with a partial cutaway, of a surgical tool assembly 200 in accordance with some embodiments. The tool assembly 200 includes a proximal actuation assembly 202, a main shaft 206, a two degree of freedom (2-dof) wrist 208, shown in partial cutaway, and an end effector 210. The end effector 210 includes a first articulable jaw 214 rotatably secured to a base 212, a stationary second jaw 216 detachably secured to the base 212 and a 2-dof wrist 208 operatively coupled between the main shaft 206 and the base 212. The end effector base 212 includes a pivot member 217 about which a proximal end of the first jaw 214 pivots to achieve opening and closing movement of the first jaw 214 relative to the second jaw 216. In some embodiments, the pivot member includes a pivot pin 217 that defines a pivot axis 213 about which the first jaw 214 pivots and that is secured between the end effector base 212 and a proximal end of the first jaw 214. A proximal end of the first jaw 214 pivots about the pivot axis 213 to achieve opening and closing movement of the first jaw 214 relative to the second jaw 216. In some embodiments, the actuation assembly 202 is operatively coupled with the wrist 208 so as to selectively reorient the end effector 210 relative to the main shaft 206 in two dimensions, and is operatively coupled with the end effector 210 so as to actuate one or more end effector features, such as the first articulable jaw 214, relative to the end effector base 212. A variety of actuation components can be used to couple the actuation assembly 202 with the wrist 208 and with the end effector 210, for example, control cables, cable/hypotube combinations, drive shafts, pull rods, and push rods. In many embodiments, the actuation components are routed between the actuation assembly 202 and the wrist 208 and the end effector 210 through a bore of the main shaft 206. The end effector 210 shown in FIG. 15 includes a surgical stapler in which the second detachable stationary second jaw 216 includes an elongated stapler cartridge 218, and in which an articulable first jaw 214 includes an anvil 220 against which staples are deformed to staple together tissue disposed between the first and second jaws 214, 216.

FIG. 16 is an illustrative perspective view, with a partial cutaway, of the end effector 210 of FIG. 15 with an empty second jaw 216 from which the stapler cartridge is removed. More particularly, the empty second jaw 216 includes a stapler cartridge support channel structure 221 that includes sidewalls 225 and an outer facing bottom wall 224 that are sized to receive the stapler cartridge 218. As explained below, the support channel bottom wall 224, which acts as a second jaw cam surface, defines a central second longitudinal cam slot 255 that runs most of the length of the bottom wall 224. An elongated rotary drive screw 222, which includes a distal end 222-2 and a proximal end 222-1, extends longitudinally along the length of the second jaw 216. The proximal end of the drive screw 222 is rotatably supported within the end effector base 212. The distal end 222-2 of the drive screw 222 is received within and rotatably supported by an annular bearing 228, which is secured to an upstanding base 230 such that the drive screw runs down the center of the support channel 221 between the upstanding walls 222 and above the bottom wall 224.

FIG. 17 is an illustrative exploded view of a detachable stationary second jaw 216 in accordance with some embodiments. The second jaw 216 includes the support channel structure 221, which includes a proximal end 221-1 and a distal end 221-2. The support channel 221 includes the sidewalls 225 and the bottom wall 224, which defines the second elongated longitudinal slot 232, only a small distal portion of which is visible. The elongated cartridge 218 includes a proximal end 218-1 and a distal end 218-2. The cartridge includes cartridge outer sidewalls 234 and an upper surface 236. The upper surface 236 faces the anvil 220 of the first jaw, which acts as an anvil, when the second jaw is mounted to the end effector base 212. The upper surface 236 of the cartridge 218 defines a central first longitudinal cartridge slot 238 that extends through the cartridge 218 and that is aligned with the second longitudinal cam slot 255 when the cartridge 218 is disposed within the support channel structure 221. The cartridge upper surface portion includes inner opposed facing sidewalls 238-1, 238-2 that define the cartridge slot 238 and act as a cam surfaces to guide a drive member 250, as described more fully below. The upper surface 236 also defines multiple rows of longitudinally spaced staple retention slots 240 that extend longitudinally along one side of the first cartridge slot 238 and defines multiple rows of longitudinally spaced staple retention slots 240 that extend longitudinally along an opposite side of the first cartridge slot 238. Each staple retention slot 240 is sized to receive a fastener 242 and a staple pusher 244. A pusher shuttle 246 includes a plurality of inclined upstanding cam wedges 246 and a knife edge 248 upstanding between and proximal to the cam wedges 246. The cartridge 218 defines multiple longitudinal slots (not shown) in its underside along which the cam wedges 246 can slide with the knife upstanding from and sliding within the first cartridge slot 238. Alternatively, in accordance with some embodiments, a knife (not shown) can be secured to the drive member 250 described below.

During operation of surgical stapler end effector 210, pusher shuttle 246 translates through the longitudinal pusher slots 239-1, 239-2, formed in an underside of the cartridge 218 to advance the cam wedges 246 into sequential contact with pushers 244 within the longitudinally spaced retention slots 240, to cause pushers 244 to translate vertically within retention slots 240, and to urge fasteners 242 from retention slots 240 into the staple deforming cavities (not shown) formed within the anvil 220 of the first jaw 214. As the pusher shuttle 246 translates longitudinally, it pushes up fasteners 242, which are deformation against the anvil 220. Meanwhile, the knife edge 248 upstands through the first cartridge slot 238 and cuts tissue between tissue regions stapled through action of the cam wedges 246, fasteners 242 and the anvil 220. U.S. Pat. No. 8,991,678 (filed Oct. 26, 2012) issued to Wellman et al., which is incorporated herein in its entirety by this reference, discloses a surgical stapler cartridge and its operation.

Figure 18:
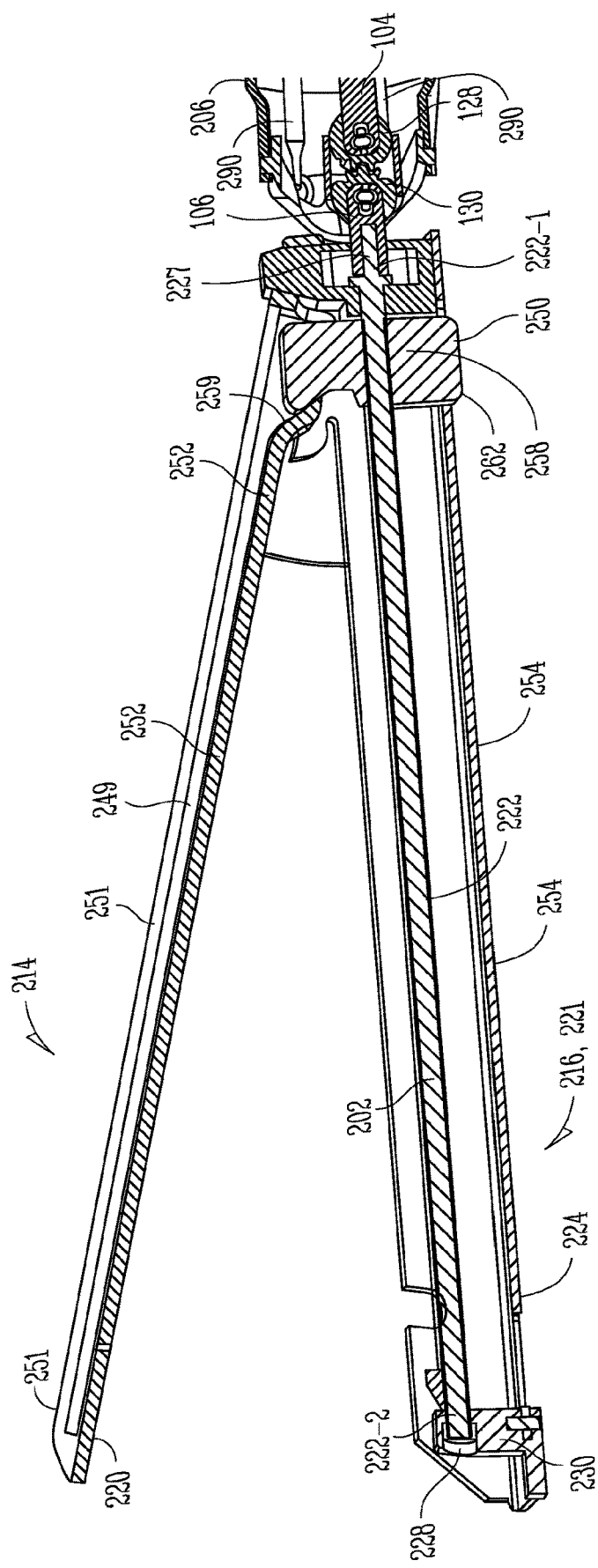
FIG. 18 is an illustrative cross sectional view of the end effector of FIGS. 15-17 in accordance with some embodiments.

FIG. 18 is an illustrative cross sectional view of the end effector 210 of FIGS. 15-17 in accordance with some embodiments. Like the view in FIG. 16, the cartridge 218 is removed leaving the second jaw 216 as primarily consisting of the empty support channel structure 221. The main shaft 206 encloses the distal drive shaft 104, which extends through the center of the main shaft 206 between the proximal actuation assembly 202 and the drive shaft plastic bearing 128. The proximal driven shaft 106 extends between the driven shaft plastic bearing 130 and the proximal end 222-1 of the rotary drive screw 222. Referring back to FIGS. 7-8, it can be seen that a distal end 116 of the driven shaft 106 defines a female coupler 223 contoured to interfit with a complementary male coupler 227 at the distal end 222-2 of the drive screw so that the driven shaft 106 and the rotary drive screw 222 rotate in unison. The driven shaft 106 houses additional control components such as steering (hypo)tubes which are not shown in order to simplify the drawings. A screw driven drive member 250 is mounted to the end effector 210 between the first jaw and the second jaw. The drive member 250 defines a threaded bore through which the drive screw 222 is threaded. The drive member 250 is configured so that rotation of the drive screw in a first rotational direction within the threaded bore causes the drive member 250 to move in a longitudinal path defined by the rotary drive screw 222 in a direction in toward the drive screw distal end distal end 222-2. Conversely, rotation of the rotary drive screw 222 in a second rotational direction within the threaded bore, opposite to the first rotational direction, causes the drive member 250 to move in a longitudinal path defined by the drive screw 222 in a direction in toward the drive screw proximal end distal end 222-1.

The first jaw 214 includes the anvil 220, an outer top cover 251 that overlays a back side of the anvil 220. A first cam surface 249, which includes a longitudinally extending first jaw rotation cam surface 259 and a longitudinally extending first jaw clamping cam surface 252, is disposed between the external cover 251 and the anvil 220. The first cam surface is described more fully with reference to FIG. 19B and FIGS. 22A-22F. The second jaw 216 defines a longitudinally extending second cam surface 254. The first jaw rotation cam surface 259 cooperates with the driver member 250, which acts as a cam follower driven by the screw drive 222, to rotate the articulable first jaw 214 between open and closed positions. As explained below with reference to FIG. 24B, a spring is used to keep the jaws open prior to gripping and clamping. With the first jaw 214 in the closed position, the first jaw clamping cam surface 252 and second cam surface 254 are longitudinally aligned and can cooperate with the driver member 250, which acts as a cam follower driven by the screw drive 222, to securely hold anatomical tissue between the first and second jaws 214, 216 to achieve tissue gripping and tissue clamping.

Figure 19A:
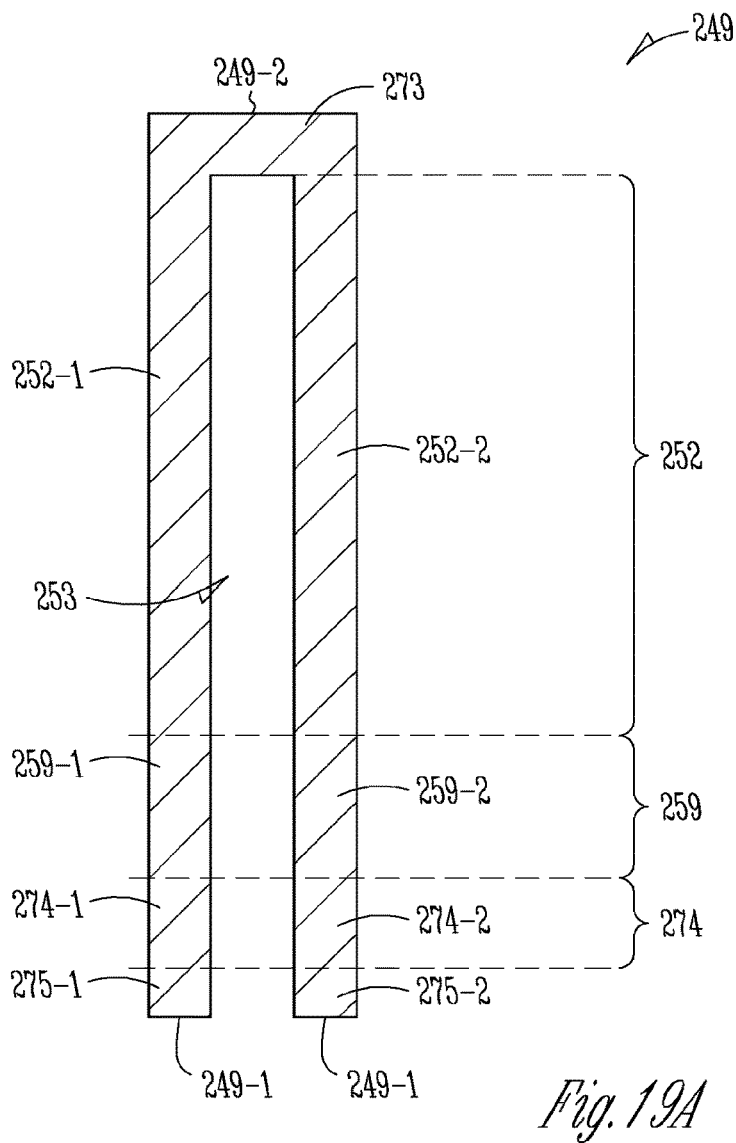
FIG. 19A is a top elevation view of the first cam surface in accordance with some embodiments.
Figure 19B:
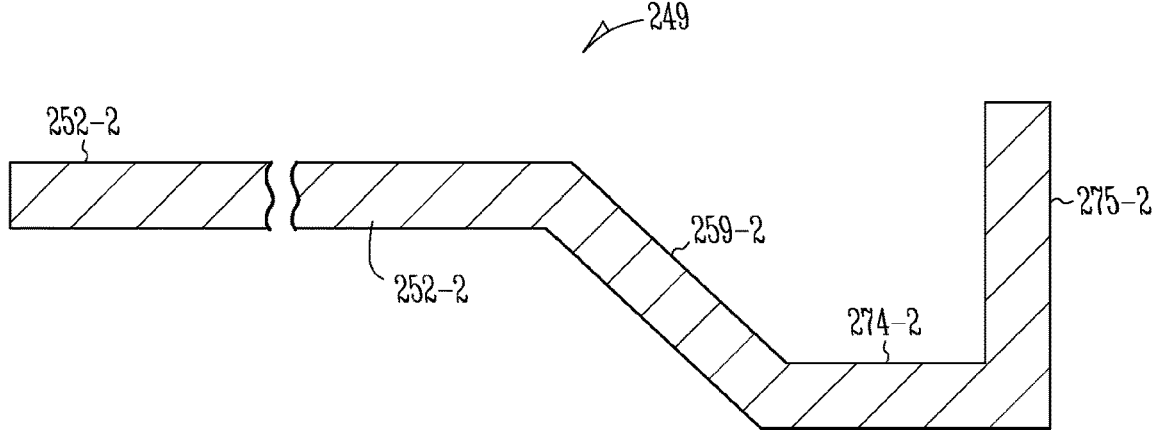
FIG. 19B is a cross-section view showing edges of one side of the first cam surface in accordance with some embodiments.

FIG. 19A is a top elevation view of the first cam surface 249 in accordance with some embodiments. FIG. 19B is a cross-section view showing edges of one side of the first cam surface 249 in accordance with some embodiments. As explained above, the first cam surface 249 is securely mounted within the first jaw 214 between the anvil 220. and the external top cover 251. The first cam surface 249 includes a proximal end 249-1 and a distal end 249-2 having multiple functional segments between them: a rotation cam segment 259, a clamping cam segment 252, a distal cross-segment 273, a proximal bridging segment 274 and a proximal base segment 275.

The rotation cam segment 259 comprises a first elongated cam edge 259-1 and a parallel second elongated edge portion 259-2 (also referred to herein as a third pair of lateral side edges 259-1, 259-2), which are laterally spaced apart and which act as a proximal portion of the first cam surface 249. A first jaw clamping cam segment 252 comprises a third elongated cam edge 252-1 and a parallel fourth elongated cam edge 252-2 (also referred to herein as a first pair of lateral side edges 252-1, 252-2), which acts as a distal cam portion of the first cam surface 249. The first and third elongated cam edges 259-1, 252-1 are joined integrally so as to together define a first continuous edge. The second and fourth elongated cam edges 259-2, 252-2 are joined integrally so as to together define a second continuous edge. The first continuous edge comprising cam edges 259-1, 252-1 and the second continuous edge comprising cam edges 259-2, 252-2 together define a first elongated cam follower slot 253 between them. The first and third cam edges 259-1, 252-1 and the second and fourth cam edges 259-2, 252-2 are offset at an angle from each other.

The distal cross-segment 273 connects the distal ends of the third and fourth edges 252-1, 252-2 and is secured to a distal portion of the top cover 251. The proximal base segment 275 includes parallel edges 275-1, 275-2 that are upstand substantially transverse to the third and fourth cam edges 252-1, 252-2 and that are secured to a proximal end portion of the top cover 251. The proximal bridging segment 274 includes parallel edges 274-1, 274-2 that respectively integrally interconnect the first cam edge 259-1 with one of the base edges 275-1 and interconnect the second cam edge 259-2 with the other of the base edges 275-1.

Figure 20:
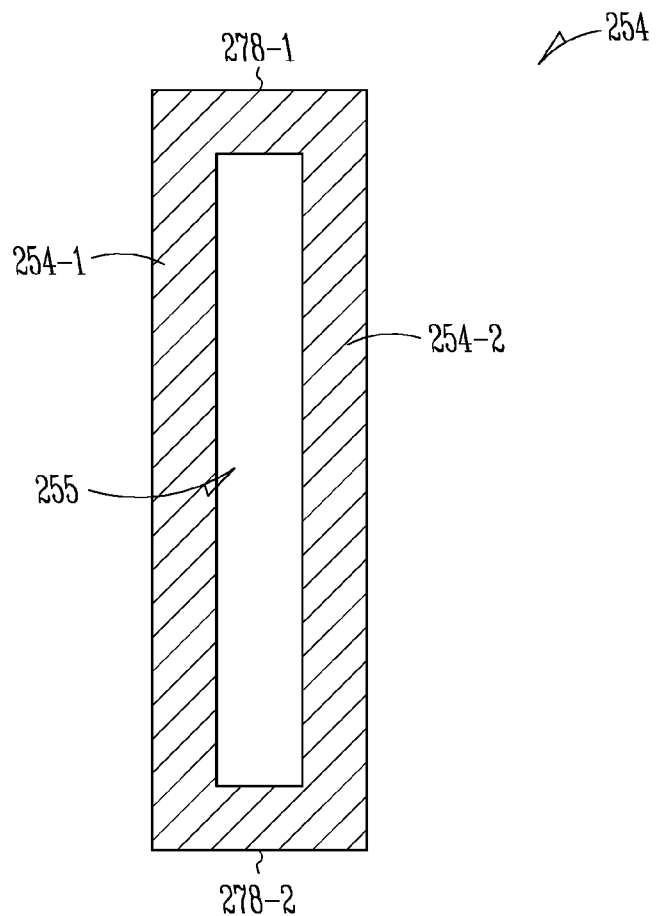
FIG. 20 is an illustrative bottom elevation view of the longitudinally extending second cam surface in accordance with some embodiments.

FIG. 20 is an illustrative bottom elevation view of the longitudinally extending second cam surface 254 in accordance with some embodiments. The second cam surface 254 is formed in the bottom wall 224 of the stapler cartridge support channel structure 221. The second cam surface 254 includes fifth and sixth elongated cam edges 254-1, 254-2 (also referred to as a second pair of lateral side edges 254-1, 254-2), which are laterally spaced apart. The fifth and sixth elongated cam edges 254-1, 254-2 together define the second elongated cam follower slot 255 between them. Proximal and distal cross members 278-1 and 278-2 interconnect the fifth and sixth edges portions.

Figure 21:
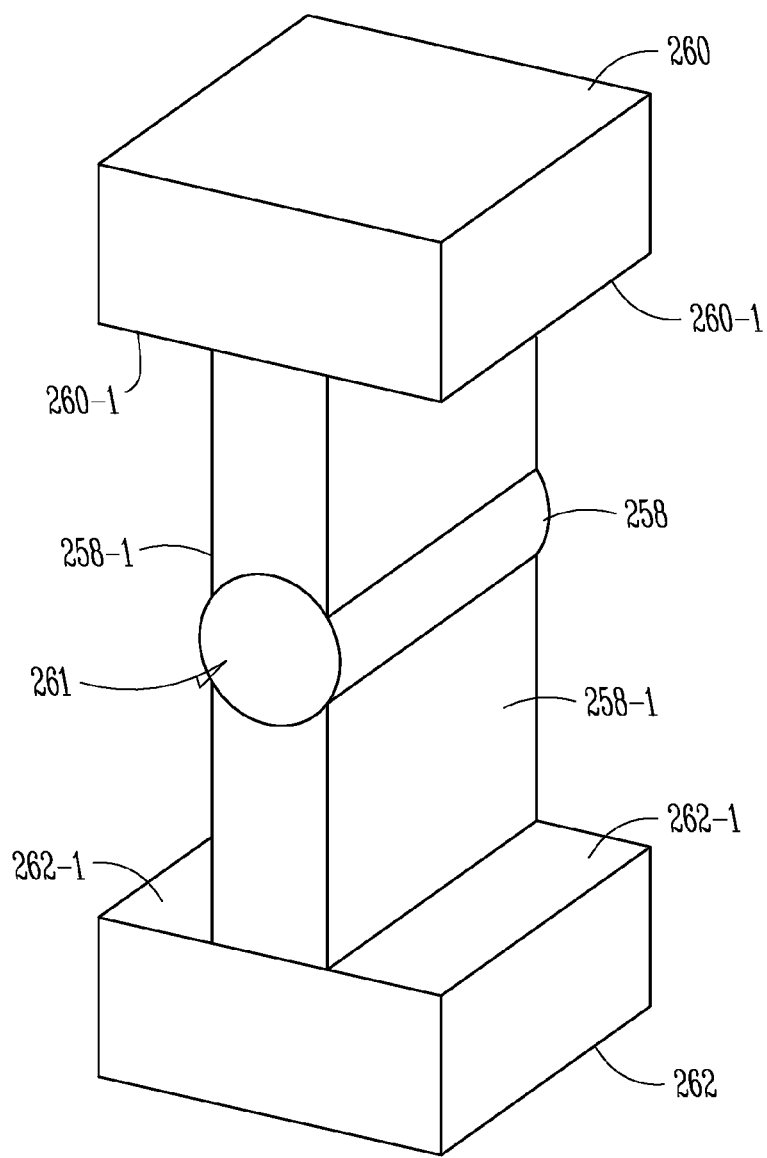
FIG. 21 is an illustrative perspective view of the drive member in accordance with some embodiments.

FIG. 21 is an illustrative perspective view of the drive member 250 in accordance with some embodiments. The drive member 250 has an I-beam contour that includes a cross-beam portion 258, a first transverse beam portion 260 secured to a first end of the cross-beam portion 258, and a second transverse beam 262 secured to a second end of the cross-beam 258 portion. The cross-beam portion 258 defines a threaded bore 261 that extends through it that is sized and contoured to engage a drive screw (not shown). The first and second transverse beam portions 260, 262 extend from the cross-beam 258 in a direction perpendicular to an axis of the threaded bore 261. In operation, the cross-beam portion 258 acts as a cartridge slot cam follower. The cross-beam portion 258 is sized to slidably fit simultaneously within the first cam follower slot 253 and the second elongated cam follower slot 255. The first transverse beam portion 260 defines a first inward facing surface 260-1 that acts as a first jaw cam follower. The second transverse beam 262 defines a second inward facing surface 260-2 that acts as a second jaw cam follower.

FIGS. 22A-22F are schematic cross-sectional side views representing stages in the articulation of the first jaw 214 as the drive member 250 is moved in a linear motion longitudinally from a proximal starting position toward a distal end of the end effector 210 and interacts with the rotation cam 259 (also referred to herein as the third pair of lateral side edges 259-1, 259-2) and the first jaw clamping cam 252 (also referred to herein as the first pair of lateral side edges 252-1, 252-2) of the first cam surface 249 along the way, in accordance with some embodiments. Certain components of the end effector 210 are omitted to simplify the drawings. Moreover, in this cross-section side view, only the second side edges 259-2, the fourth cam edge 252-2, one parallel edge 274-2 and one base edge 275-2 are shown. In this description, the linear position of the drive member 250 is expressed in terms of an $X_N$ positions along an X axis collinear with the axis of the drive screw 222. A fastener 282 secures the first cam surface 249 to the first arm 214 (indicated by dashed lines). The first arm 214 is mounted to a pivot pin 217 secured to the end effector base 212 (not shown) so as to be rotatable about an axis of the pivot pin 217 relative to the base 212 and to the second jaw 216 (not shown), which is attached to the base 212 during operation. The drive member 250 is mounted upon the drive screw 222. As most clearly shown in FIGS. 16-17, the drive screw 222 extends longitudinally (along the X axis) within the cartridge support channel structure 221 for substantially its entire length. In operation, the drive screw 222 rotatably extends through a longitudinal cavity (not shown) formed within the cartridge 218 beneath the rows of retention slots 240. Forward rotation of the drive screw 222 causes the drive member 250 to move linearly along the drive screw toward the drive screw distal end 222-1, which is disposed near a distal end of the second jaw 216.

Figure 22A:
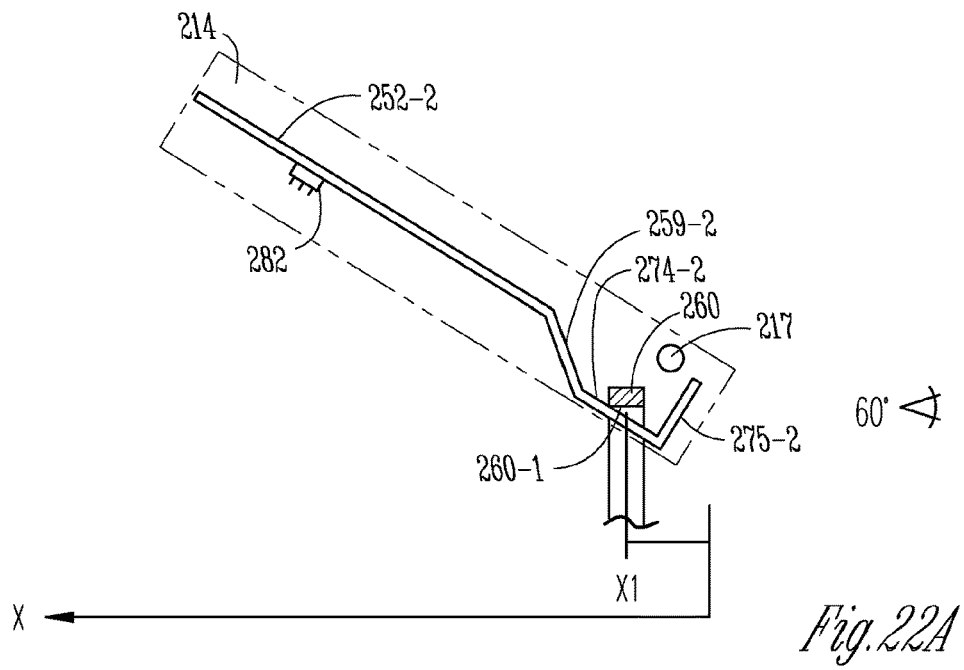
FIGS. 22A-22F are schematic cross-sectional views representing stages in the articulation of the first jaw as the drive member is moved in a linear motion longitudinally toward a distal end of the end effector and interacts with the first cam surface in accordance with some embodiments.

FIG. 22A shows the first arm 214 fully open inclined at an angle of 60 degrees relative to a longitudinal axis of the second jaw 216 and with the drive member 250 located at starting linear position $X_1$. It will be appreciated that different stated angles and different $X_N$ positions are approximations and examples used for illustrative purposes. More specifically, the drive member 250 is disposed with its cross-beam portion 258 between the parallel edges 274-1, 274-2 of the bridging segment 274 and with its first transverse beam portion 260 spaced apart in a proximal direction from the first and second cam edges (the third pair of lateral side edges) 259-1, 259-2 of the rotation cam 259.

Figure 22B:
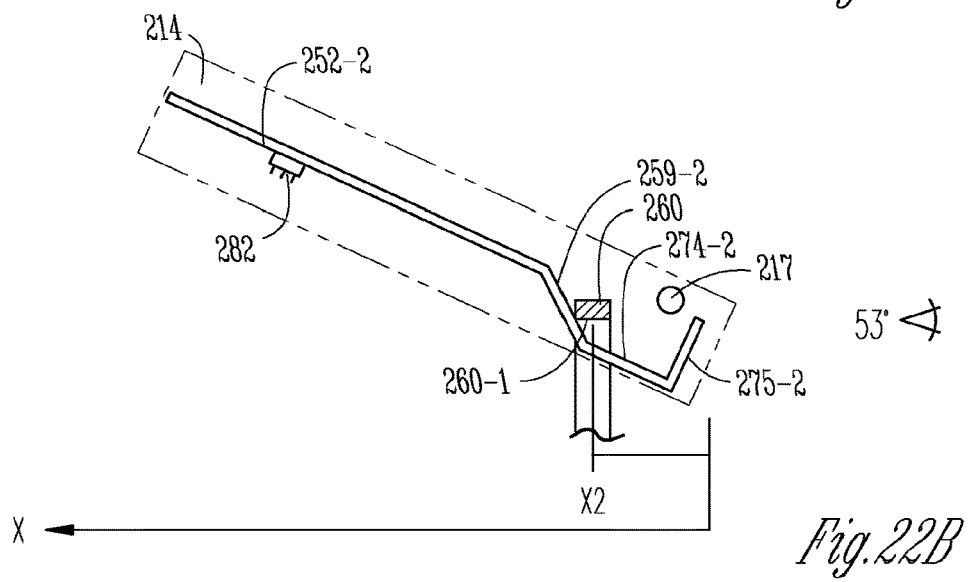

FIG. 22B shows the first arm 214 partially open inclined at an angle of 52 degrees relative to the longitudinal axis of the second jaw 216 and with the drive member 250 located at linear position $X_2$. The drive member 250 is disposed with its cross-beam portion 258 partially between the a portion of the parallel first and second cam edges (the third pair of lateral side edges 259-1, 259-2) and between a portion of the parallel edges 274-1, 274-2 of the bridging segment 274 and with its first transverse beam portion 260 interacting as a cam follower with the first and second cam edges 259-1, 259-2 of the rotation cam 259. The interaction between the first transverse beam portion 260 first and second cam edges 259-1, 259-2 during linear x-direction motion of the drive member 250 from $X_1$ to $X_2$ has caused the first arm 214 to rotate from a 60 degree angle to a 52 degree angle.

Figure 22C:
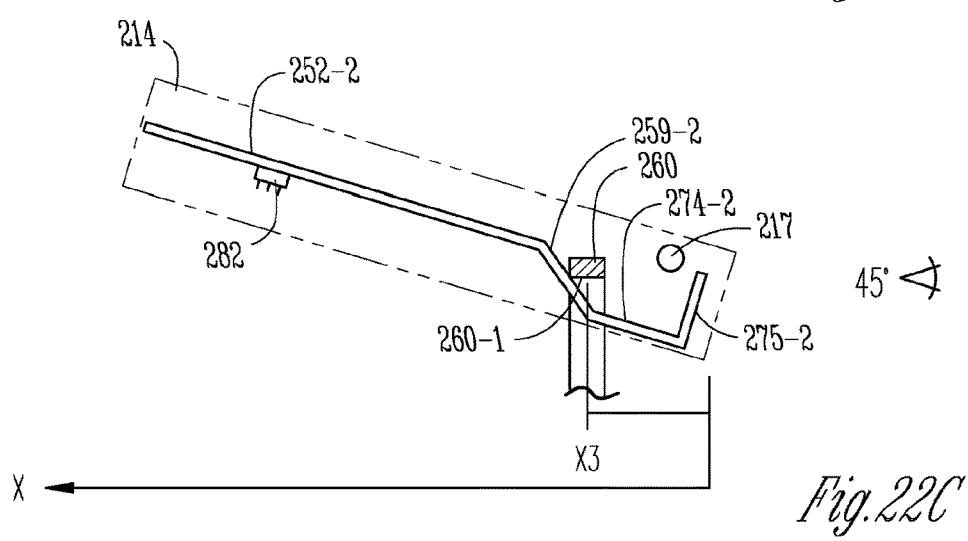

FIG. 22C shows the first arm 214 partially open inclined at an angle of 45 degrees relative to the longitudinal axis of the second jaw 216 and with the drive member 250 located at linear position $X_3$. The drive members 250 is disposed with its cross-beam portion 258 fully between the parallel first and second cam edges (the third pair of lateral side edges) 259-1, 259-2 of the rotation cam and with its first transverse beam portion 260 interacting as a cam follower with the first and second cam edges 259-1, 259-2 of the rotation cam 259. The interaction between the first transverse beam portion 260 first and second cam edges 259-1, 259-2 during linear x-direction motion of the drive member 250 from $X_2$ to $X_3$ has caused the first arm 214 to rotate from a 52 degree angle to a 45 degree angle.

Figure 22D:
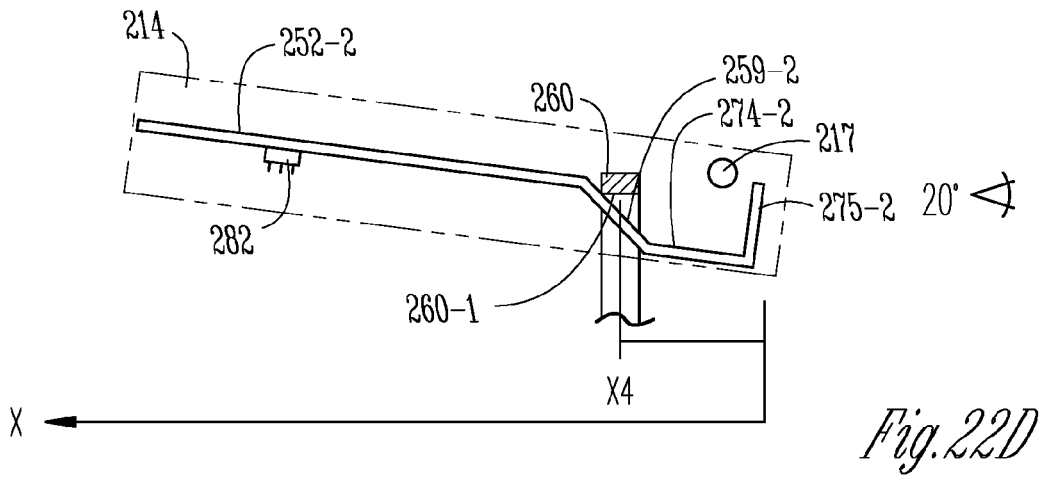

FIG. 22D shows the first arm 214 partially open inclined at an angle of 20 degrees relative to the longitudinal axis of the second jaw 216 and with the drive member 250 located at linear position $X_4$. The drive members 250 is disposed with its cross-beam portion 258 fully between the parallel first and second cam edges (the third pair of lateral side edges) 259-1, 259-2 of the rotation cam and with its first transverse beam portion 260 interacting as a cam follower with the first and second cam edges 259-1, 259-2 of the rotation cam 259. The interaction between the first transverse beam portion 260 first and second cam edges 259-1, 259-2 during linear x-direction movement of the drive member 250 from $X_3$ to $X_4$ has caused the first arm 214 to rotate from a 45 degree angle to a 20 degree angle.

Figure 22E:
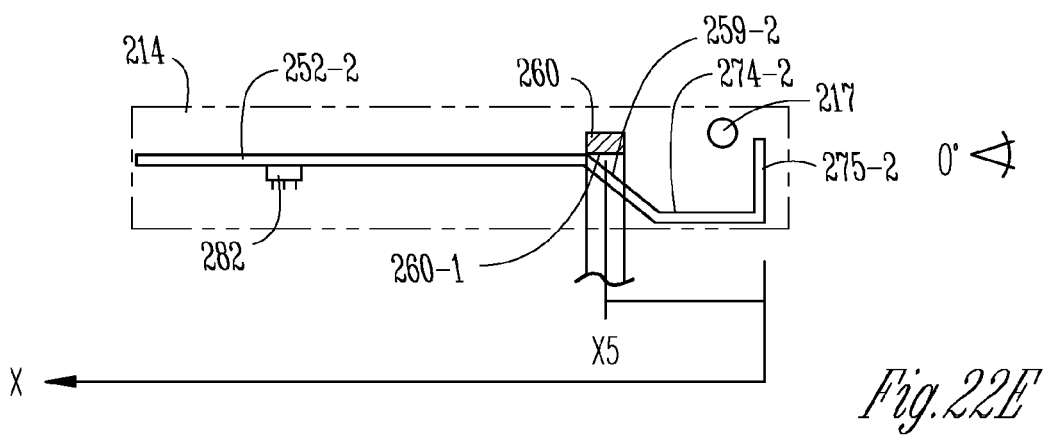

FIG. 22E shows the first arm 214 closed inclined at an angle of 0 degrees relative to the longitudinal axis of the second jaw 216 and with the drive member 250 located at linear position X. The drive members 250 is disposed with its cross-beam portion 258 still fully between the parallel first and second cam edges (the third pair of lateral side edges) 259-1, 259-2 of the rotation cam but with its first transverse beam portion 260 now interacting as a cam follower with the third and fourth cam edges (the first pair of lateral side edges) 252-1, 252-2 of the first jaw clamping cam 252. The interaction between the first transverse beam portion 260 first and second cam edges 259-1, 259-2 during linear x-direction movement of drive member 250 from $X_4$ to $X_5$ has caused the first arm 214 to rotate from a 20 degree angle to a 0 degree angle.

In accordance with some embodiments, the first cam surface 249 is configured such that the first transverse beam portion 260 transitions from interacting with the first and second cam edges (the third pair of lateral side edges) 259-1, 259-2 of the rotation cam to interacting with the third and fourth cam edges (the first pair of lateral side edges) 252-1, 252-2 of the first jaw clamping cam 252 as the linear motion of the drive member 250 causes the first arm 214 to reach a 0 degree angle, parallel with the second jaw 216. In accordance with some embodiments, there is a prescribed spacing that the I-beam maintains between the anvil and cartridge. The distance may be adjusted based upon by cartridge size (e.g., staple length). To achieve this each reload size has a different overall height to make the appropriate gape between anvil and cartridge. The I-beam is sized and dimensioned to maintain this distance.

Figure 22F:
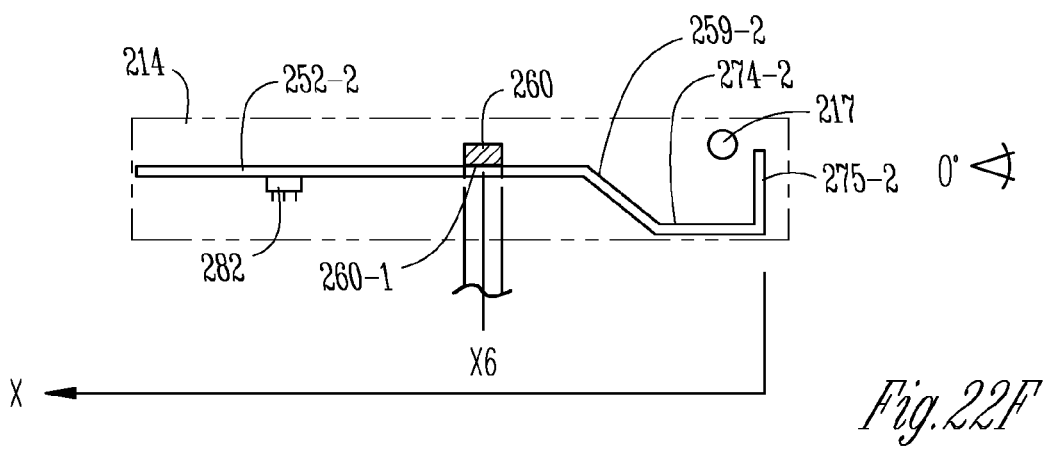

FIG. 22F shows the first arm 214 closed inclined at an angle of 0 degrees relative to the longitudinal axis of the second jaw 216 and with the drive member 250 located at linear position $X_6$. The drive members 250 is disposed with its cross-beam portion 258 fully between the parallel third and fourth cam edges (the first pair of lateral side edges) 252-1, 252-2 of the first jaw clamping cam 252 and with its first transverse beam portion 260 interacting with the third and fourth cam edges 252-1, 252-2 of the first jaw clamping cam 252. The linear motion of the drive member 250 from $X_5$ to $X_6$ has caused the first arm 214 but the rotational angle of the first arm 214 has remained at 0 degree angle, parallel to the second arm 216.

Figure 23A:
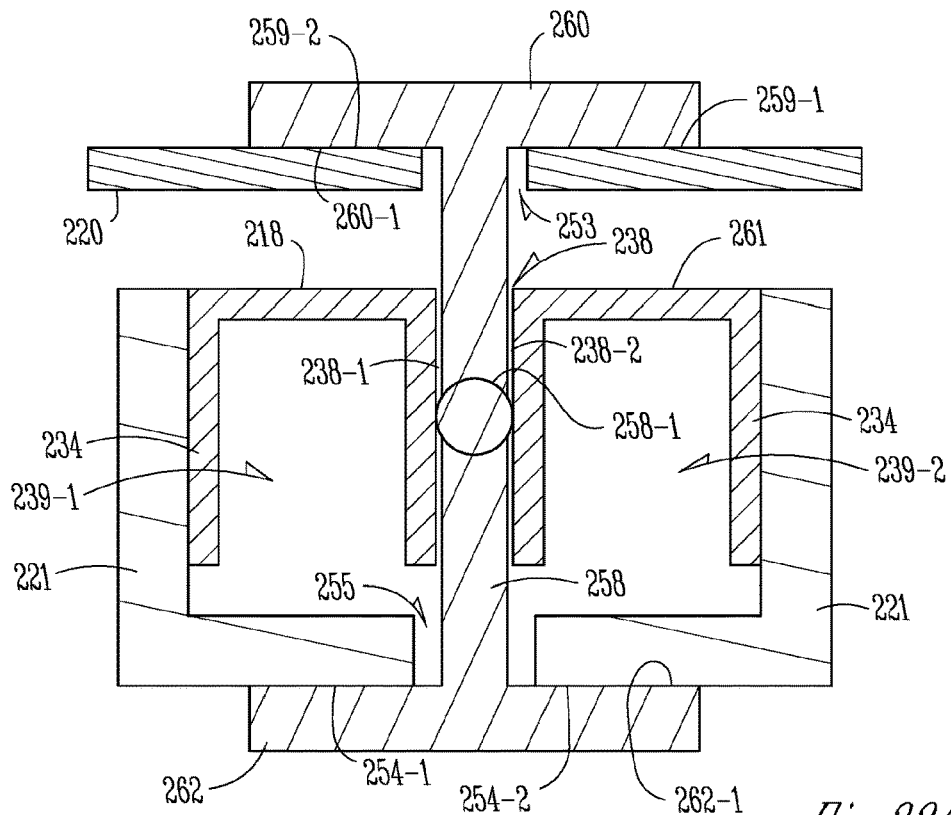
FIG. 23A shows the cross-sectional view without the pusher shuttle shown within the cartridge in accordance with some embodiments.
Figure 23B:
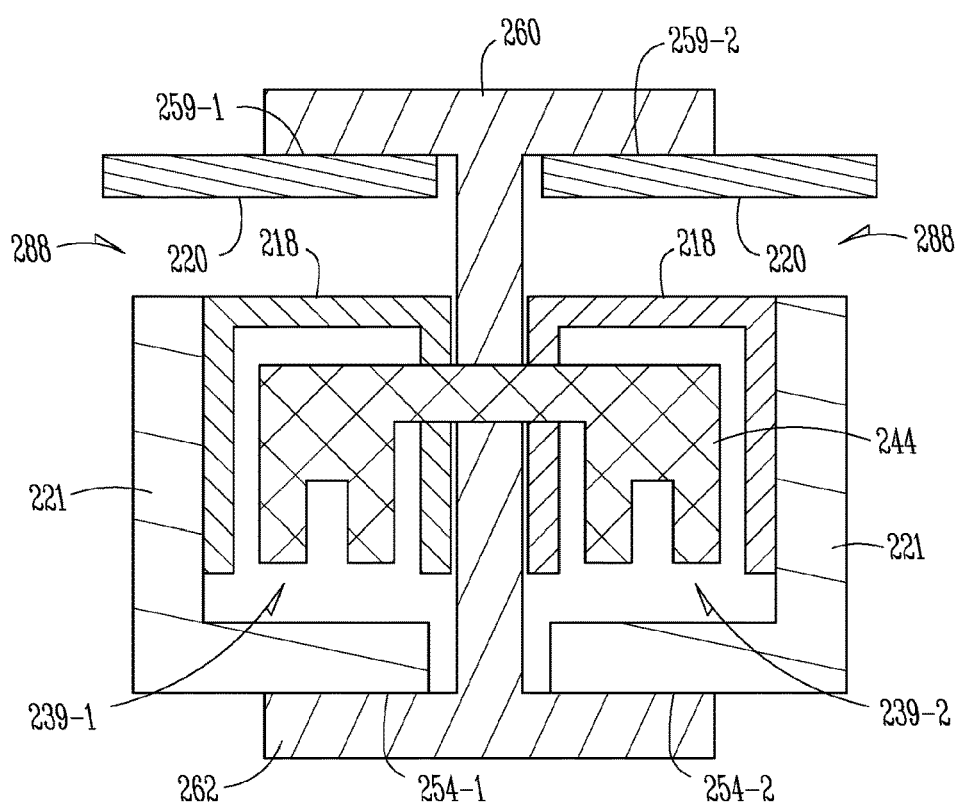
FIG. 23B shows the cross-sectional view with the pusher shuttle shown within the cartridge in accordance with some embodiments.

FIGS. 23A-23B are schematic cross sectional views of the first and second jaws in a closed position in a proximal direction along the drive screw axis in accordance with some embodiments. FIG. 23A shows the cross-sectional view without the pusher shuttle 244 shown within the cartridge 218. FIG. 23B shows the cross-sectional view with the pusher shuttle 244 shown within the cartridge 218. Certain components of the jaws 214, 216 are omitted to simplify the drawings.

FIG. 23A shows the drive member 250 disposed so that the first inward facing surface 260-1 of the first transverse beam 260 urges the respective third and fourth cam edges 252-1, 252-2 toward the fifth and sixth cam edges 254-1, 254-2 and so that conversely, the second inward facing surface 262-1 of the second transverse beam 262 urges the respective fifth and sixth cam edges 254-1, 254-2 toward the third and fourth cam edges 252-1, 252-2. The cam follower surfaces 258-1 of cross-beam portion 258 interact with opposed cartridge inner sidewall cam surfaces 238-1, 238-2 of the cartridge slot 238 to guide the drive member 250 along the length of the cartridge 218. The cartridge outer sidewalls 234 and the cartridge inner sidewalls 234 define first and second elongated pusher channels 239-1, 239-2 that are laterally spaced apart on opposite sides of the cartridge slot 238 and that extend substantially along the length of the cartridge 218.

FIG. 23B shows the illustrative cross-section distal end view of FIG. 23B with the addition of the pusher shuttle 244 disposed within the pusher channels 239-1, 239-2. The drive member 250 drives the pusher shuttle 244 in front of it in a longitudinal direction from a proximal end toward distal ends of the cartridge 218 that is mounted within the second jaw 216. It is noted that there is a gap 288 between the anvil surface 220 and the cartridge 218 in which tissue can be captured.

FIGS. 24A-30 are illustrative cross-sectional drawings of a portion of the end effector 210 of FIGS. 15-18 showing the longitudinal movement of the drive member 250 and corresponding motion of the first and second jaws 214, 216 in response to rotation of the rotatable screw drive 222 in accordance with some embodiments. As shown in FIG. 15, the articulable first jaw 214 is pivotally mounted on first and second pivot pins 217 (only one shown) to allow it its proximal end to pivot so as to rotatably move its anvil surface 220 toward or way from the cartridge 218 disposed within the cartridge support channel structure 221 of the second detachable jaw 216. It is noted that the pivot pins are not visible in the illustrative drawings of FIGS. 24A-30.

Figure 24A:
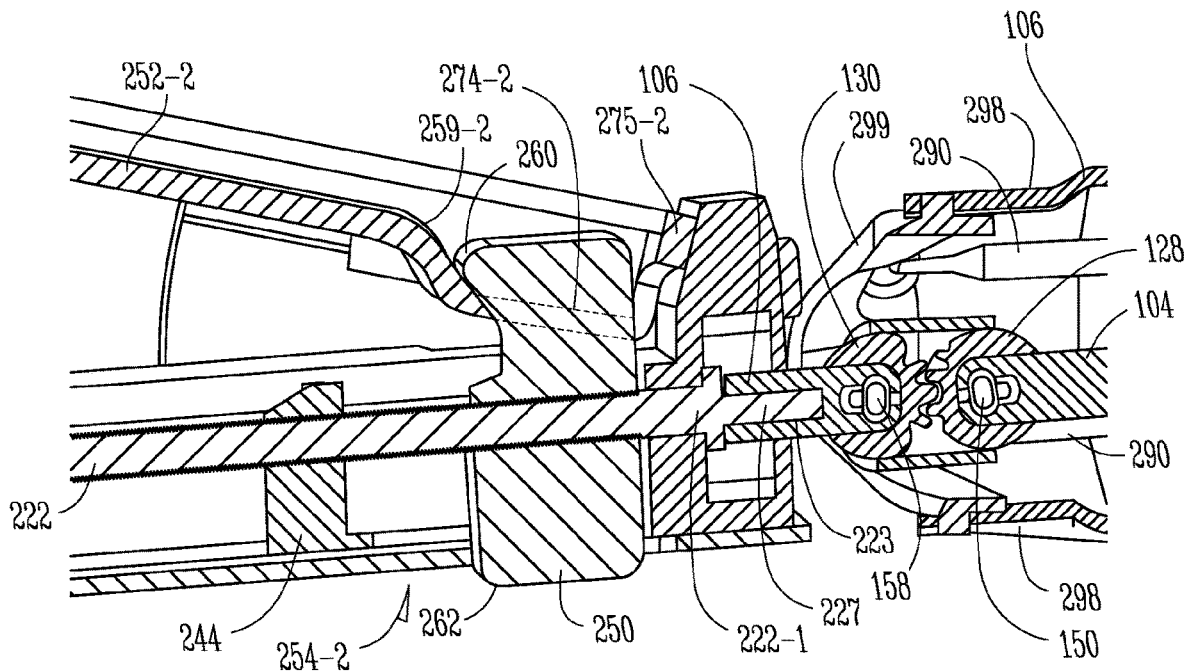
FIG. 24A is an illustrative cross-sectional view of a portion of the end effector of showing the first jaw in an open position and the drive member in a starting position in accordance with some embodiments.
Figure 24B:
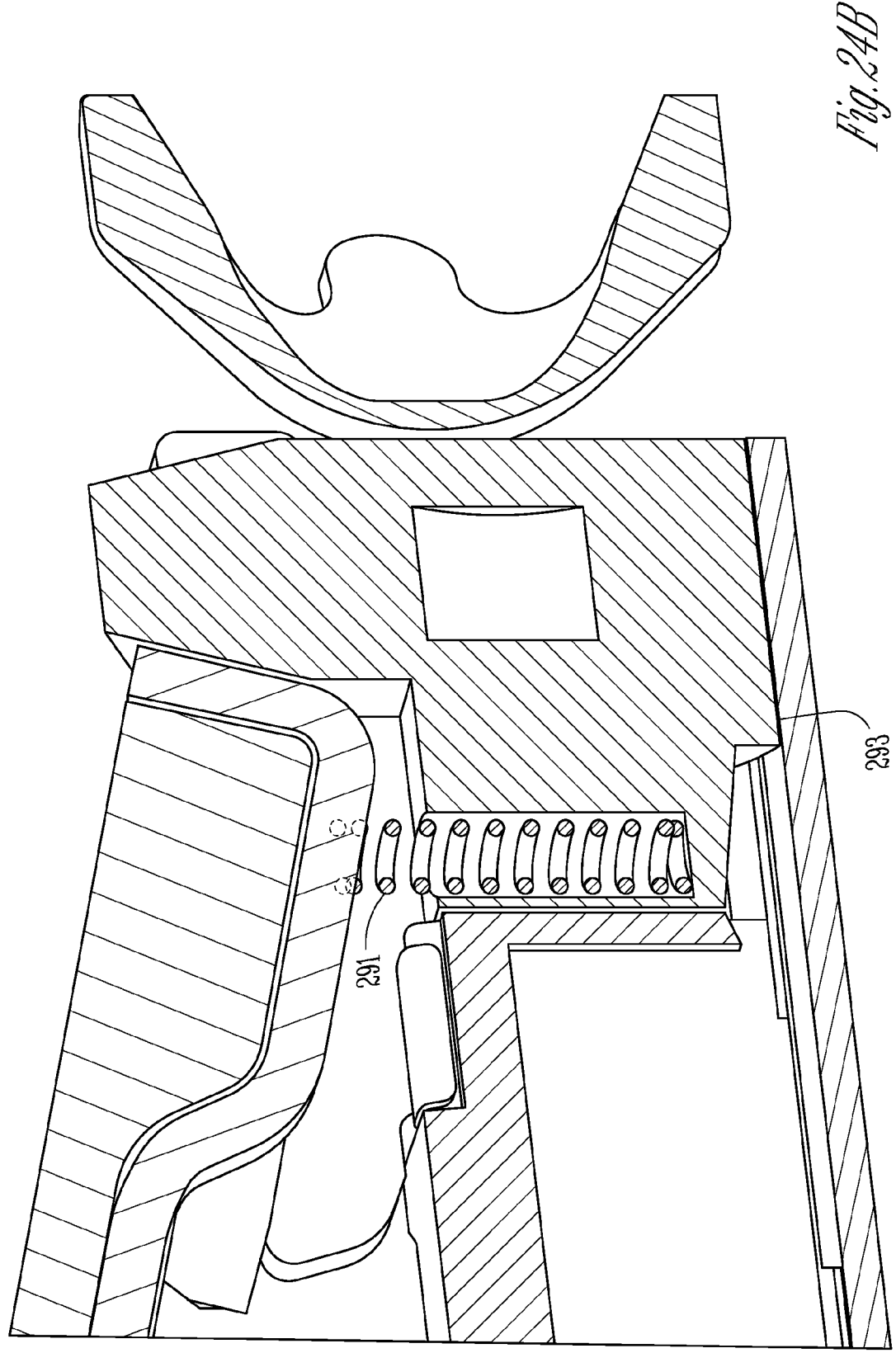
FIG. 24B is an illustrative cross-sectional view of a portion of the view of FIG. 24A showing a spring used to keep the jaws open prior to gripping and clamping operations in accordance with some embodiments.

FIG. 24A is an illustrative cross-sectional view of a portion of the end effector 210 of showing the first jaw 214 in an open position and the drive member 250 in a starting position in accordance with some embodiments. The view in FIG. 24A corresponds to the schematic view shown in FIG. 22A. FIG. 24B is an illustrative cross-sectional view of a portion of the view of FIG. 24A, enlarged to show a spring 291 seated in a recess disposed to urge the first jaw 214 away from the second jaw 216 to keep the jaws in an open position open prior to gripping and clamping operations in accordance with some embodiments. With the first jaw 214 is in an open position, a surgeon can maneuver the end effector 210 so as to position it to encompass anatomical tissue structures that is to be stapled between the first and second jaws 214, 216. An open first jaw 214 is the default position in accordance with some embodiments. The drive member 250 is disposed in a starting position adjacent proximal ends of the first and second jaws 214, 216 and adjacent the proximal end 222-1 of the screw drive 222. The drive member 250 is longitudinally spaced apart from the pusher shuttle 244 with the pusher shuttle 244 positioned at a more distal location within the cartridge 218. The drive member first transverse beam 260 is disengaged from both the rotation cam surface 259 and from the first jaw clamping cam surface 252 first jaw flat cam surface 252. It will be appreciated that in these cross-section views, only portions of the second rotation cam edge 259-2 and a portion of the fourth clamping cam edge 252-2 are shown.

With the detachable second jaw 216 is attached, a male coupler 227 formed at the proximal end 222-1 of the rotatable screw drive 222, is inserted into and engages the female coupler 223 located at the distal end 116 of the driven shaft 106. It will be appreciated that a rotation force can be applied to the drive shaft 104, which is mounted within the main shaft 206, and that rotational force is transferred through the torque transmitting mechanism 102 to the driven shaft 106, which is mounted within the end effector 210, and that force also can be transferred to the drives the screw drive 222, which extends longitudinally within the cartridge 218 mounted in the second jaw. Hypotubes 290 that can be used to achieve two degree of freedom movement of the end effector 210 also are shown housed within the main shaft.

Figure 25:
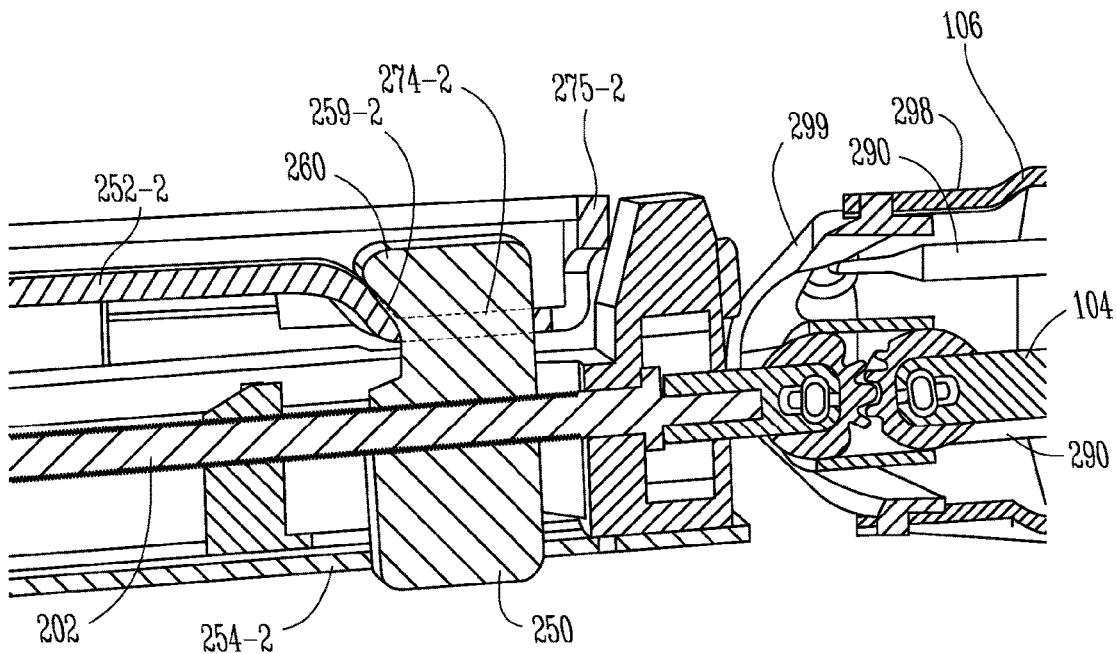
FIG. 25 is an illustrative cross-sectional view of a portion of the end effector showing the first jaw and the drive member in grip positions in accordance with some embodiments.

FIG. 25 is an illustrative cross-sectional view of a portion of the end effector 210 showing the first jaw 214 and the drive member 250 in grip positions in accordance with some embodiments. The view in FIG. 25 corresponds to the schematic view shown in FIG. 22E. FIGS. 22B-22E illustrate the transition of the first jaw 214 between the starting position shown in FIG. 24A and the grip position in FIG. 25. During the transition, the screw drive 222 drives the drive member 250 to advance distally longitudinally along the axis of the screw drive 222 so that the first transverse beam 260 interacts with the second rotation cam edge 259-2 to cause the first arm to rotate from the start position to the grip position. The pusher shuttle 244 defines a bore through which the screw drive 222 passes without affecting its longitudinal position.

In the grip position, the drive member 250 is disposed longitudinally spaced apart from the pusher shuttle 244 with the pusher shuttle 244 positioned at a more distal location within the cartridge 218. Thus, the drive member 250 has not yet caused movement of the pusher shuttle 244 and no staples have been discharged. The first transverse beam 260 is engaged with the fourth clamping cam edge 252-2 and the second transverse beam 262 is engaged with the sixth clamping edge 254-2. The first and second transverse beams 260, 262, thereby cooperate to exert inward force on the second and fourth clamping edges 252-2, 254-2 so as to urge the first and second jaws 214, 216 into a closed position that allows a sufficient gap between them accommodate tissue gripped between them.

Once the first jaw 214 is in the grip position, a surgeon then may take some time to assess whether or not to staple the tissue captured within the jaws. In accordance with some embodiments, the surgeon can selectively actuate the screw drive 222 to move the driver member 250 back to the starting position to re-open the jaws and maneuver the jaws to capture a different portion of tissue. Thus, a surgeon can selectively grip and release tissue portions in search for the optimal tissue site that he wants to have between gripped between the jaws for insertion of staples.

Figure 26:
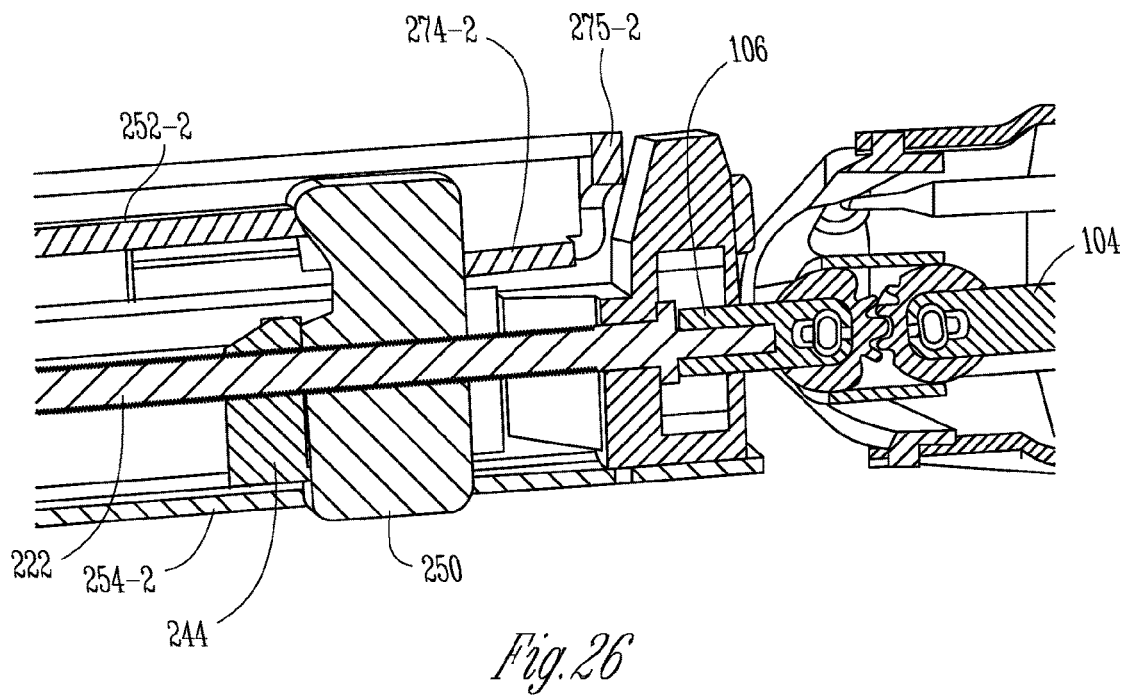
FIG. 26 is an illustrative cross-sectional view of a portion of the end effector showing the first jaw and the drive member in a first clamp positions in accordance with some embodiments.

FIG. 26 is an illustrative cross-sectional view of a portion of the end effector 210 showing the first jaw 214 and the drive member 250 in a first clamp positions in accordance with some embodiments. The view in FIG. 26 corresponds generally to the schematic view shown in FIG. 22F. During a transition from the grip position to the first clamp position, the screw drive 222 drives the drive member 250 to advance distally longitudinally along the axis of the screw drive 222 to a position that is longitudinally closer to the pusher shuttle 244 but that does not in contact with the pusher shuttle 244. Thus, no staples are pushed by the pusher shuttle 244 in response to the transition from the grip position to the first clamp position. In the first clamp position, like the grip position, the first and second transverse beams 260, 262 cooperate to exert inward force on the second and fourth clamping edges 252-2, 254-2 so as to urge the first and second jaws 214, 216 into a closed position that allows a sufficient gap between them accommodate tissue gripped between them. In accordance with some embodiments, tissue pressure imparted by the jaws can be determined indirectly based upon system torque on the lead screw. This can be determined during grip or during clamp.

Figure 27:
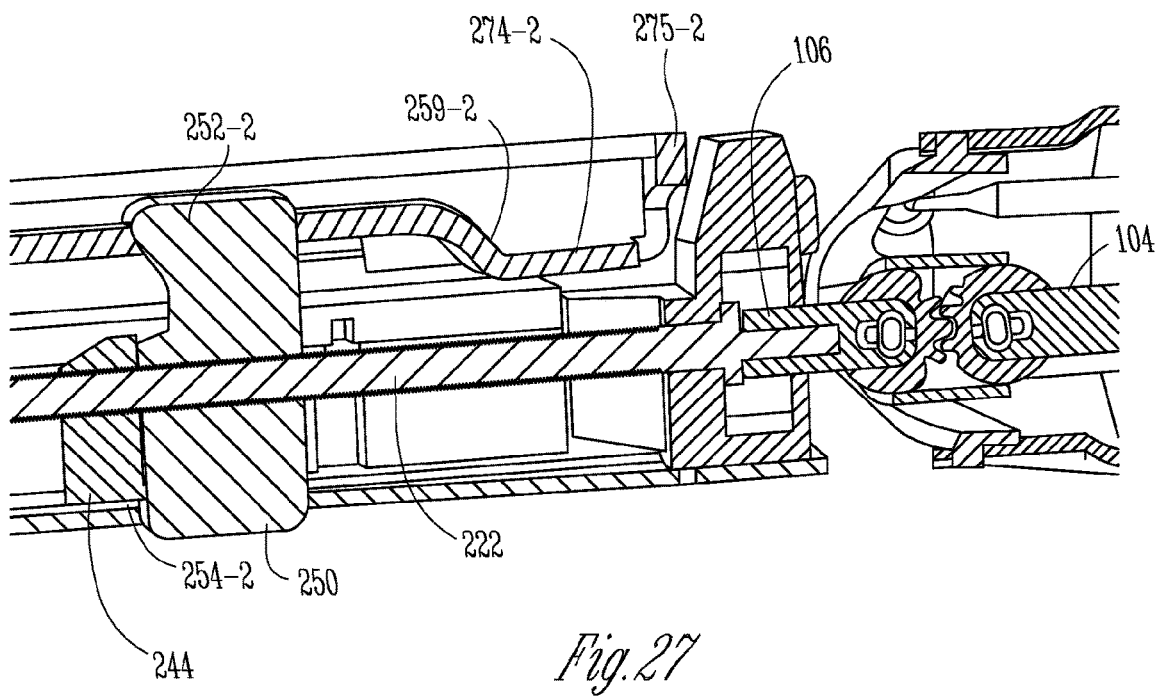
FIG. 27 is an illustrative cross-sectional view of a portion of the end effector showing the first jaw and the drive member in a staple pushing positions in accordance with some embodiments.

FIG. 27 is an illustrative cross-sectional view of a portion of the end effector 210 showing the first jaw 214 and the drive member 250 in a staple pushing positions in accordance with some embodiments. The view in FIG. 27 also corresponds generally to the schematic view shown in FIG. 22F. During a transition from the first clamp position to the to the staple pushing position, the screw drive 222 drives the drive member 250 to advance distally longitudinally along the axis of the screw drive 222 to a position in which it abuts against and imparts motion to the pusher shuttle 244 causing the pusher shuttle 244 to push staples through tissue and to cause their deformation against the anvil 202 as described above with reference to FIG. 17. In the staple pushing position, the first and second transverse beams 260, 262 cooperate to exert inward force on the second and fourth clamping edges 252-2, 254-2 so as to urge the first and second jaws 214, 216 into a closed position that allows a sufficient gap between them accommodate tissue gripped between them. It will be appreciated, therefore, that the pushing position constitutes a second clamping position similar to the first clamping position.

Figure 28:
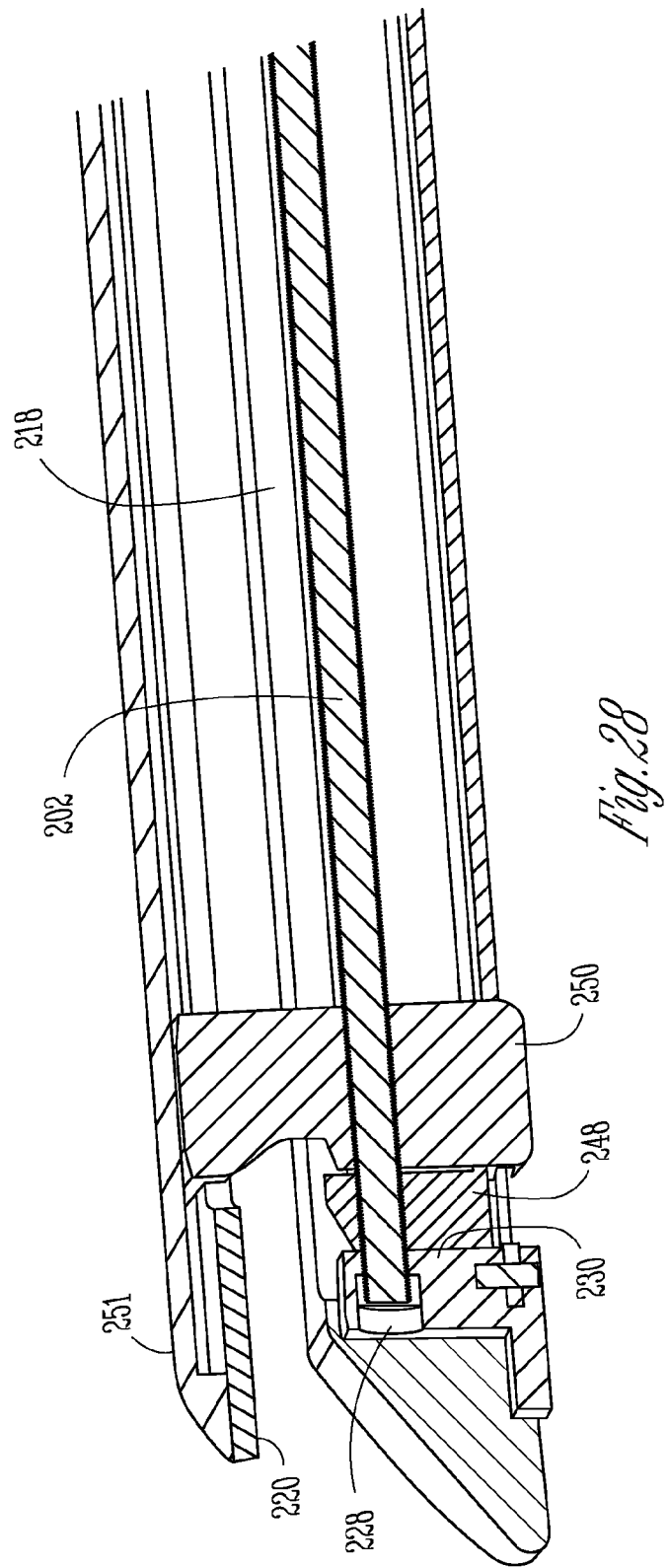
FIG. 28 is an illustrative cross-sectional view of a portion of the end effector showing the first jaw and the drive member in a stapler fully fired position in accordance with some embodiments.

FIG. 28 is an illustrative cross-sectional view of a portion of the end effector 210 showing the first jaw 214 and the drive member 250 in a stapler fully fired position in accordance with some embodiments. The pusher shuttle 244 abuts against the upstanding base 230 supporting the annular bearing 228 in which a distal end 222-2 of the drive screw 222 rotates. During a transition from the staple pushing position of FIG. 27 to the to the stapler fully fired position of FIG. 28, the screw drive 222 drives the drive member 250 and the pusher shuttle 244, which abuts against it, to traverse distally longitudinally along the entire remaining axis of the screw drive 222 causing the pusher shuttle 244 to push staples through tissue and to cause their deformation against the anvil 202 during the traversal. During the traversal, the first and second transverse beams 260, 262 cooperate to exert inward force on the second and fourth clamping edges 252-2, 254-2 as described above. The distal base 230 acts as a stop surface at the end of the traversal.

Figure 29:
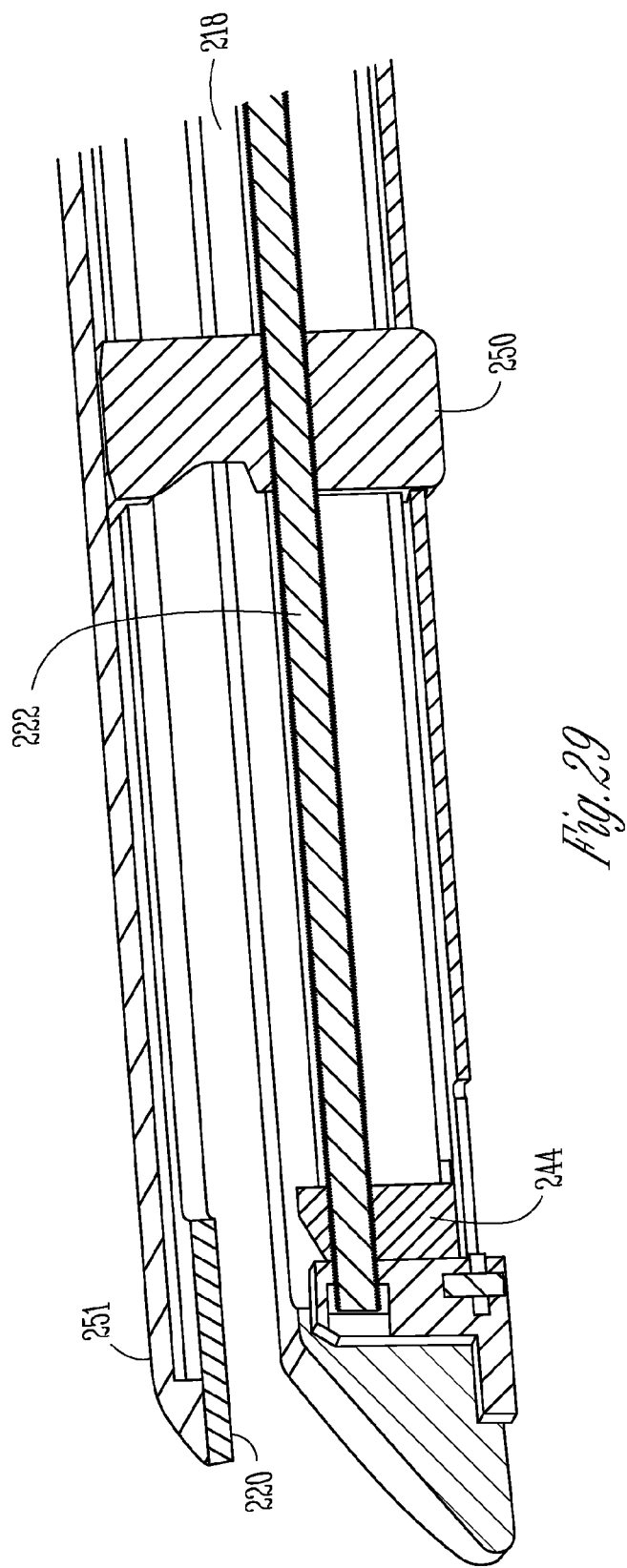
FIG. 29 is an illustrative cross-sectional view of a portion of the end effector showing the first jaw and the drive member during return of the drive member to the start position in accordance with some embodiments.

FIG. 29 is an illustrative cross-sectional view of a portion of the end effector 210 showing the first jaw 214 and the drive member 250 during return of the drive member 250 to the start position in accordance with some embodiments. After all of the staples have been pushed out and the pusher shuttle 244 has reached the distal base 230, the drive screw rotation is reversed so as to move the drive member 250 longitudinally in a proximal direction back to the start position. During the reverse traversal, the first and second transverse beams 260, 262 cooperate to exert inward force on the second and fourth clamping edges 252-2, 254-2 as described above.

Figure 30:
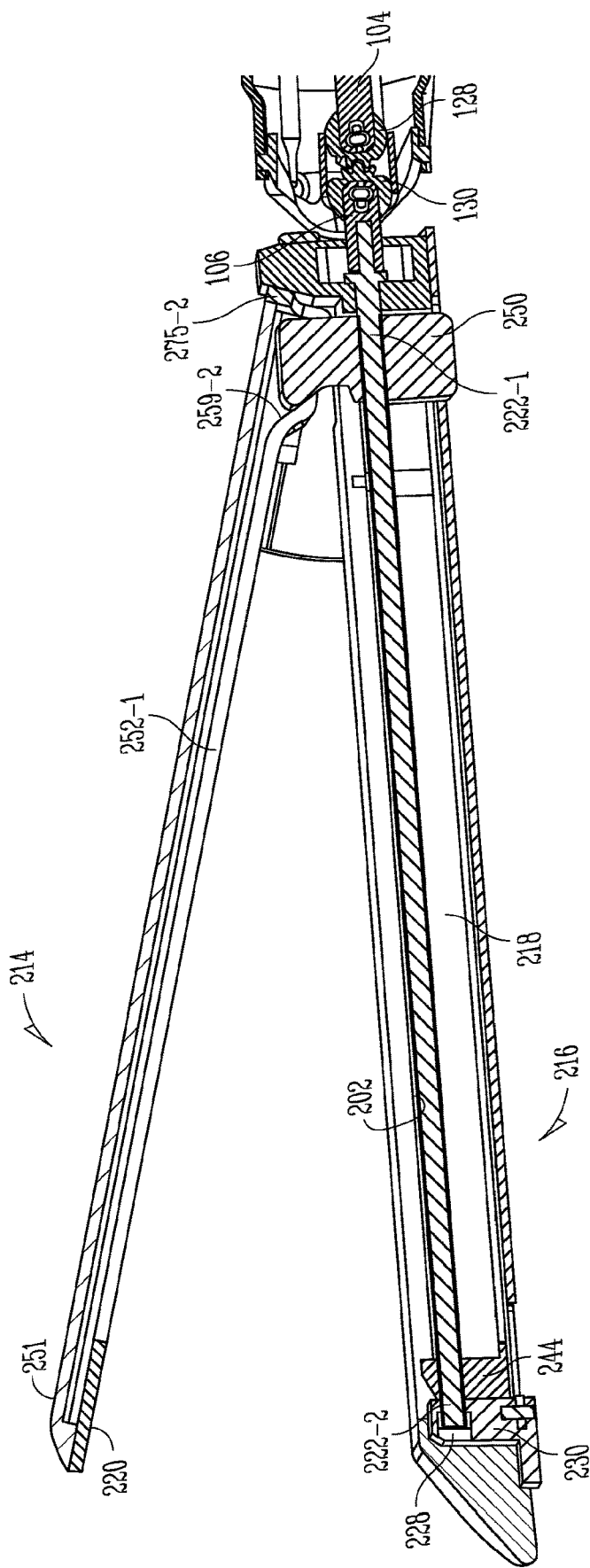
FIG. 30 is an illustrative cross-sectional view of a portion of the end effector showing the first jaw and the drive member in a complete configuration with the drive member back in the to the start position in accordance with some embodiments.

FIG. 30 is an illustrative cross-sectional view of a portion of the end effector 210 showing the first jaw 214 and the drive member 250 in a complete configuration with the drive member 250 back in the to the start position in accordance with some embodiments. The drive member first transverse beam 260 is disengaged from both the rotation cam surface 259 and from the first jaw clamping cam surface 252 first jaw flat cam surface 252. In accordance with some embodiments, a spring (not shown) can be used to re-open the jaws. causes the first jaw 214 to move to an open position. The pusher shuttle 244 has been left behind in abutment against the distal base 230.

Figure 31:
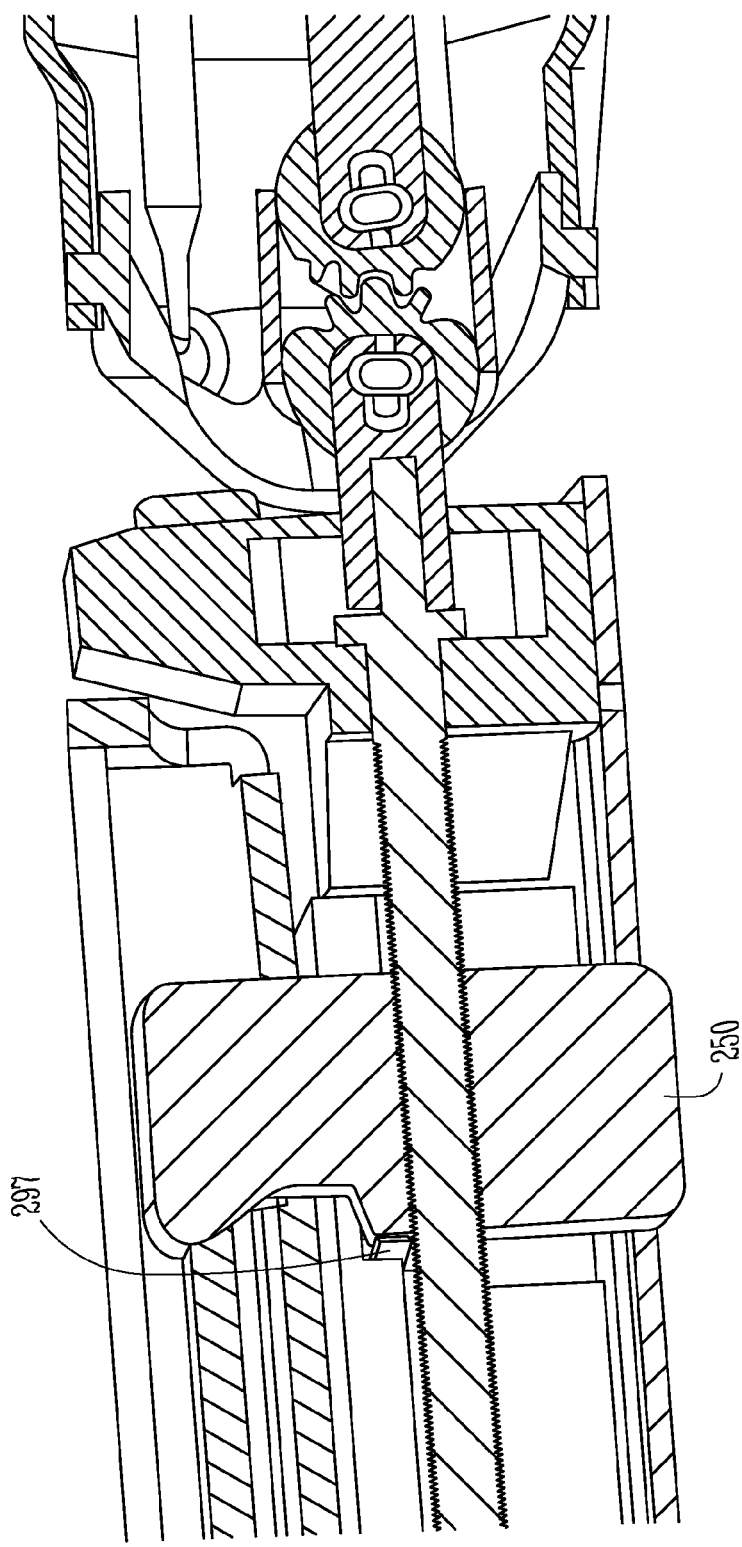
FIG. 31 is an illustrative drawing showing a lockout mechanism in accordance with some embodiments.

FIG. 31 is an illustrative drawing showing a lockout mechanism in accordance with some embodiments. The lockout mechanism comprises a lockout spring 297 that flexes in a proximal direction but does not flex in the distal direction The spring 297 is initially biased due to interaction with the drive member 250 so as to be recessed against a lateral side of the second jaw 216 when a reload cartridge 218 is installed. During firing of staples, the drive member 250 is driven toward the distal end of the cartridge 218 to discharge the staples. Since the lockout spring 297 is initially recessed against the lateral side of the second jaw 216, it does not block passage of the drive member 250 during its initial drive toward the distal end of the second jaw 216. When the drive member 250 member is returned to its initial position, the spring 297 flexes proximally against the lateral side of the second jaw 216, allowing the drive member 216 to pass over it. Once the drive member passes over the spring 297, the spring snaps out preventing the drive member 250 from advancing again toward the distal end of the second jaw 216.

FIGS. 32A-32B are illustrative drawings showing details of the two degree of freedom wrist 208 of the end effector 210 with the torque transmitting mechanism 102 in an inline position (FIG. 32A) and in a articulated position (FIG. 32B) in accordance with some embodiments. The drive shaft 104 extends through the center of the driven shaft 106 and engages with the coupling member 108 and the drive shaft plastic bearing 128 as described above. First arms 294 depend proximally from opposite sides of the base 212 of the end effector 210. Each arm defines a pair of islets 295. Hypotubes 290 extend longitudinally within the main shaft 206 about the drive axis and define hooks 296 at their proximal ends that engage the islets 295. Second arms 298 extend distally from the main shaft offset ninety degrees form the first arms to define a clevis. The first and second arms 294, 298 enable a pitch and yaw pivot, which allows the assembly to act as a wrist 208 with two degrees of freedom while maintaining the center hollow for the cardan. In operation, and arms 294 enable yaw (up and down movement from the perspective of the drawing), and arms 298 enable pitch (left to right movement from the perspective of the drawing), Operation of the wrist 292 will be understood from U.S. Pat. No. 8,852,174, which is incorporated by reference above.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

What is claimed is:

1. A universal double joint comprising:
   a drive rotatable bearing having a first surface and comprising a proximal transverse bore;
   a proximal cross pin configured to receive an imparted drive force and to impart the imparted drive force to the drive rotatable bearing, wherein the proximal cross pin extends within the proximal transverse bore such that the drive rotatable bearing is rotatably mounted thereon;
   a drive shaft configured to receive the imparted force and including a drive clevis;
   a driven rotatable bearing having a second spherical surface and comprising a distal transverse bore;
   a distal metal cross pin configured to receive the imparted drive force and to impart the imparted drive force to the driven rotatable bearing, wherein the distal cross pin extends within the distal transverse bore such that the driven rotatable bearing is rotatably mounted thereon; and
   a driven shaft including a driven clevis.

2. The universal double joint of claim 1,
   wherein the drive rotatable bearing includes a first axial engagement structure;
   wherein the driven rotatable bearing includes a second axial engagement structure; and
   wherein the first and second axial engagement structures are configured to engage each other.

3. The universal double joint of claim 2,
   wherein the first axial engagement structure includes a first spherical gear structure; and
   wherein the second axial engagement structure includes a second spherical gear structure.

4. A surgical stapling instrument comprising the universal double joint of claim 1.

5. A universal double joint comprising:
   a sleeve member defining a proximal end opening and a distal end opening;
   a drive rotatable bearing including a first partially spherical outer surface portion sized to fit within the proximal end opening for smooth partial rotation therein and including a first axial engagement structure and a proximal transverse bore;
   a proximal cross pin configured to receive an imparted drive force and to impart the imparted drive force to the sleeve member, and to the drive rotatable bearing, wherein the proximal cross pin extends within the proximal transverse bore such that the drive rotatable bearing is rotatably mounted thereon;
   a drive shaft configured to receive the imparted force and including a drive clevis;
   a driven rotatable bearing formed of a plastic material and including a partially second spherical outer surface portion sized to fit within the distal end opening for smooth partial rotation therein and including a second engagement structure and a distal transverse bore;
   a distal cross pin configured to receive the imparted drive force and to impart the imparted drive force to the sleeve member and to the driven rotatable bearing, wherein the distal cross pin extends within the distal transverse bore such that the driven rotatable bearing is rotatably mounted thereon; and a driven shaft including a driven clevis;
wherein the first and second axial engagement structures are configured to engage each other.

6. The universal double joint of claim 5,
wherein the first axial engagement structure includes a first gear teeth; and
wherein the second axial engagement structure includes second gear teeth.

7. The universal double joint of claim 5,
wherein the first axial engagement structure includes a first spherical gear structure; and
wherein the second axial engagement structure includes a second spherical gear structure.

8. The universal double joint of claim 5,
wherein the drive rotatable bearing is formed of injection molded plastic material; and
wherein the driven rotatable bearing is formed of injection molded plastic material.

9. The universal double joint of claim 5,
wherein the first axial engagement structure includes a first gear teeth;
wherein the second axial engagement structure includes second gear teeth;
wherein the drive rotatable bearing is formed of injection molded plastic material; and
wherein the driven rotatable bearing is formed of injection molded plastic material.

10. The universal double joint of claim 5,
wherein the first axial engagement structure includes a first spherical gear structure;
wherein the second axial engagement structure includes a second gear structure;
wherein the drive rotatable bearing is formed of injection molded plastic material; and
wherein the driven rotatable bearing is formed of injection molded plastic material.

11. The universal double joint of claim 5,
wherein the proximal cross pin is configured to receive the imparted drive force from the drive shaft and to impart the imparted drive force to the sleeve member, and to the drive rotatable bearing; and
wherein the distal pin cross is configured to receive the imparted drive force from the drive shaft and to impart the imparted drive force to the sleeve member, to the driven rotatable bearing and to the driven shaft.

12. The universal double joint of claim 11,
wherein the first axial engagement structure includes a first gear teeth;
wherein the second axial engagement structure includes second gear teeth;
wherein the first gear teeth and the second gear teeth are spherically oriented to eliminate rotational speed differences between the drive shaft and the driven shaft.

13. The universal double joint of claim 5
wherein the proximal cross pin defines a proximal cross pin bore;
wherein the distal cross pin defines a distal cross pin bore; further including:
wherein the proximal cross pin is mounted between opposed arms of a proximal clevis;
wherein the distal cross pin is mounted between opposed arms of the distal clevis;
wherein the drive rotatable bearing is mounted for rotation about the proximal cross pin; and
wherein the driven rotatable bearing is mounted for rotation about the distal cross pin;
a proximal metal coupling pin extending through the proximal cross pin bore and having opposite ends abutting the sleeve member adjacent to the proximal opening; and
a distal metal coupling pin extending through the distal cross pin bore and having opposite ends abutting the sleeve member adjacent to the distal opening.

14. The universal double joint of claim 13,
wherein the drive rotatable bearing defines a slot sized to permit passage of the proximal metal coupling pin during rotation of the drive rotatable bearing about the proximal cross pin;
wherein the driven rotatable bearing defines a slot sized to permit passage of the distal metal coupling pin during rotation of the driven rotatable bearing about the distal metal cross pin.

15. A universal double joint comprising:
a first rotatable bearing having a first surface;
a proximal cross pin configured to receive an imparted drive force and to impart the imparted drive force to the first rotatable bearing;
a first shaft configured to receive the imparted force and including a first clevis;
a second rotatable bearing having a second surface;
a distal cross pin configured to receive the imparted drive force and to impart the imparted drive force to the second rotatable bearing, wherein the distal cross pin is mounted between opposed arms of the second clevis and the first rotatable bearing is mounted for rotation about the proximal cross pin; and
a second shaft including a second clevis.

16. The universal double joint of claim 15,
wherein the proximal cross pin defines a proximal cross pin bore; and
wherein the distal cross pin defines a distal cross pin bore.

17. The universal double joint of claim 15, wherein the first and second rotatable bearings comprise plastic and the proximal and distal cross pins comprise metal.

18. A surgical stapling instrument comprising the universal double joint of claim 15.

* * * * *